United States Patent
Truchon et al.

(10) Patent No.: US 8,518,964 B2
(45) Date of Patent: Aug. 27, 2013

(54) TRICYCLIC COMPOUNDS USEFUL AS INHIBITORS OF KINASES

(75) Inventors: Jean-Francois Truchon, Saint-Laurent (CA); Nicolas Lachance, Pierrefonds (CA); Cheuk Lau, L'Ile Bizard (CA); Yves Leblanc, Kirkland (CA); Christophe Mellon, L'Ile Bizard (CA); Patrick Roy, Dollard des Ormeaux (CA); Elise Isabel, Pointe-Claire (CA); Ryan D Otte, Newton Centre, MA (US); Jonathan R Young, Southborough, MA (US)

(73) Assignees: Merck Sharp & Dohme Corp., Rahway, NJ (US); Merck Canada Inc., Quebec (CA)

( * ) Notice: Subject to any disclaimer, the term of this patent is extended or adjusted under 35 U.S.C. 154(b) by 1052 days.

(21) Appl. No.: 12/085,331

(22) PCT Filed: Nov. 17, 2006

(86) PCT No.: PCT/US2006/044527
§ 371 (c)(1),
(2), (4) Date: May 21, 2008

(87) PCT Pub. No.: WO2007/061764
PCT Pub. Date: May 31, 2007

(65) Prior Publication Data
US 2010/0048551 A1    Feb. 25, 2010

(51) Int. Cl.
*A61K 31/437* (2006.01)
*A61K 31/444* (2006.01)

(52) U.S. Cl.
USPC ............... 514/292; 514/291; 546/80; 546/87

(58) Field of Classification Search
USPC .............. 514/232.8, 278, 291, 292; 544/126; 546/17, 80, 87
See application file for complete search history.

(56) References Cited

U.S. PATENT DOCUMENTS

| | | | |
|---|---|---|---|
| 4,241,064 A | 12/1980 | Matsumura et al. | |
| 6,462,036 B1 | 10/2002 | Doyle et al. | |
| 6,627,637 B2 | 9/2003 | Ritzeler et al. | |
| 7,259,161 B2 * | 8/2007 | Bethiel et al. ............. | 514/230.5 |

FOREIGN PATENT DOCUMENTS

| | | |
|---|---|---|
| EP | 1134221 | 9/2001 |
| WO | WO2004092167 | 10/2004 |

OTHER PUBLICATIONS

Suzuku, H et al., J. Chem. Soc., Perkin Trans, vol. 1, pp. 1717-1723 (1999), "Synthetic studies on indoles and related compounds. Part 46. First total synthesis of 4,8-dioxygenated beta-carboline alkaloids".

* cited by examiner

*Primary Examiner* — Renee Claytor
*Assistant Examiner* — Sahar Javanmard
(74) *Attorney, Agent, or Firm* — Laura M. Ginkel; David A. Muthard

(57) ABSTRACT

The present invention provides inhibitors of kinases, specifically IκB kinases, JAK1, JAK2, JAK3 and TYK2. The invention also provides for compositions comprising such inhibitory compounds and methods of inhibiting said kinase activity by administering the compound to a patient in need of treatment for myeloproliferative disorders, cancer or NF-κB-mediated diseases.

3 Claims, No Drawings

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Completely synthetic peptide

<400> SEQUENCE: 1

Asp Arg His Asp Ser Gly Leu Asp Ser Met Lys Asp Glu
1               5                   10

<210> SEQ ID NO 2
<211> LENGTH: 23
<212> TYPE: PRT
<213> ORGANISM: Artificial Sequence
<220> FEATURE:
<223> OTHER INFORMATION: Completely synthetic peptide

<400> SEQUENCE: 2

Lys Lys Lys Lys Glu Arg Leu Leu Asp Asp Arg His Asp Ser Gly Leu
1               5                   10                  15

Asp Ser Met Lys Asp Glu Glu
            20

<210> SEQ ID NO 3
```

```
<211> LENGTH: 15
<212> TYPE: PRT
<213> ORGANISM: Artificial Sequence
<220> FEATURE:
<223> OTHER INFORMATION: Completely synthetic peptide

<400> SEQUENCE: 3

Glu Gln Glu Asp Glu Pro Glu Gly Asp Tyr Phe Glu Trp Leu Glu
1               5                   10                  15
```

TRICYCLIC COMPOUNDS USEFUL AS INHIBITORS OF KINASES

PRIORITY CLAIM

This application is a §371 National Stage Application of PCT/US2006/044527, filed on Nov. 17, 2006, which claims priority from U.S. Provisional Application Ser. No. 60/738,905, filed on Nov. 22, 2005.

BACKGROUND OF THE INVENTION

Nuclear factor of κB (NF-κB) is a family of ubiquitously expressed transcription factors that are rapidly activated in response to several biological stimuli including inflammatory cytokines, bacterial and viral infections and other extracellular signals. NF-κB and related family members are involved in the regulation of more than 50 genes relating to immune and inflammatory responses ((Barnes P J, Karin M (1997) N Engl J Med 336, 1066-1071) and (Baeuerle P A, Baichwal V R (1997) Adv Immunol 65, 111-137)). Activation of NF-κB is regulated by an inhibitor of κB kinase (IKK) complex. Pro-inflammatory signals activate the IKK complex via a cascade of protein phosphorylations that result in increased catalytic activity; the complex in turn phosphorylates the NF-κB-bound IκB. Phosphorylation of IκB facilitates its ubiquitination and subsequent degradation by the proteasome. Freed from IκB, the active NF-κB is able to translocate to the nucleus where it binds in a selective manner to preferred gene-specific enhancer sequences and drives the transcription of a number of genes (Reviewed by Ghosh and Karin in Cell (2002) 109: S81-S96).

Phosphorylation of IκB by the IKK complex that influences cytoplasmic to nuclear translocation of NF-κB is therefore a key regulatory step in the signal transduction pathway. The IKK complex consists of two IκB kinases, IKKα (IKK1), IKKβ (IKK2), and a scaffolding protein, IKKγ (NEMO) which has no known catalytic activity. IKKα and IKKβ phosphorylate IκBs on specific serine residues to initiate protein degradation. On IκBα, phosphorylation occurs on two serine residues: Ser32 and Ser36. Studies with IκBα mutants that cannot be phosphorylated on these serine residues show they block NF-κB activation by acting as dominant-negative derivatives. Mutants of IKKα and IKKβ that act as dominant-negative derivatives also block the activation of NF-κB in cells. Thus, inhibitors of IκB kinases that prevent IκB phosphorylation would similarly block NF-κB activation and a number of such inhibitors have now been described (recently reviewed by Karin, Yamamoto and Wang in Nature Reviews (2004) 3: 17-26). Such inhibitors would be useful for treating inflammatory disorders mediated through NF-κB-dependent gene transcription.

Among the genes driven by NF-κB are several that encode for proteins that are implicated in inflammation such as cytokines TNFα, IL-1β, IL-6, IL-8; adhesion molecules such as ICAM-1, v-CAM-1, E-selectin; and enzymes such as iNOS, cPLA$_2$ and Cox-2 (Reviewed by Pahl in Oncogene (1999) 49: 6853-6866). Normally, the inflammatory process is a localized response to tissue injury or infection that leads to recruitment of blood cells and accumulation of fluid at the site of injury that ultimately results in healing. In certain instances, however, over-activity or dysfunction of the normal inflammatory response leads to exacerbation and causes harm that results in diseased states. NF-κB has been shown to be activated in a number of inflammatory diseases. As NF-κB drives the expression of a number of key molecules implicated in inflammation and immune response, inhibition of its activation under such diseased states would block the underlying inflammation and prevent, halt or reverse the disease. This broad anti-inflammatory activity of NF-κB would be advantageous over current treatment options such as NSAIDs that treat the symptoms but not the underlying causes of the disease. NF-κB has been reported to be a key link between inflammation and cancer (reviewed by Li et al., in Trends in Immunology (2005) 26, 318-325; Greten and Karin (2004) 206, 193-199). NF-κB drives several genes that promote cell survival such as c-IAP-1, c-IAP-2, Bcl-XL and p53 and a number of genes that promote proliferation such as cyclin-D1 and c-myc. The transcription factor has been reported to be constitutively activated in a number of cancers including breast, prostate and melanoma. Activation of other pathways that have been implicated in cancer such as HER2, IGF-1, Ras and Akt has also been reported to result in NF-κB activation. Furthermore, anti-neoplastic agents have been demonstrated to result in the activation of NF-κB. Thus, inhibiting NF-κB would have significant advantages over current treatment options in cancer therapy as a chemopreventive, chemosensitizer, and a therapeutic agent in cancers including cancer of the breast, prostate and skin.

The JANUS (JAKs) family of proteins are comprised of 7 homology domains including 2 kinase domains; a catalytic (JH1) and a pseudo kinase domain (JH2) that is devoid of catalytic activity. Currently, there are four known mammalian JAK family members: JAK1, JAK2, JAK3 and TYK2. JAK1, JAK2 and TYK2 are ubiquitously expressed whereas JAK3 is expressed in the myeloid and lymphoid lineages. The JAK family members are non-receptor tyrosine kinases that associate with many cell surface receptors such as hematopoietin cytokines, receptor tyrosine kinases and GPCR's (see Table 1) which regulate diverse cell processes including migration, proliferation, differentiation, and survival. Binding of the ligand to their respective extracellular receptor leads to the recruitment of a JAK protein and subsequent phosphorylation of both the receptor and the JAK protein. The STATs (known as signal transducers and activators of transcription protein), which are the main downstream effectors of JAK, are recruited by pJAK leading to the phosphorylation and dimerization of the STAT proteins which subsequently translocate to the nucleus and drive gene transcription.

TABLE 1

| Ligands | JAK Kinases | Stats |
|---|---|---|
| IFN family | | |
| IFN-α,β,γ,limitin | TYK2, JAK1 | STAT1, STAT2 (STAT3, STAT 4, STAT 5) |
| IFN-χ | JAK1, JAK2 | STAT1 (STAT5) |
| IL-10 | TYK2, JAK1 | STAT3 |
| IL-19 | undefined | undefined |
| IL-20 | undefined | STAT3 |
| IL-22 | undefined | STAT3, STAT5 |
| Gp130 family | | |
| IL-6 | JAK1, JAK2 | STAT3, STAT1 |
| IL-11 | JAK1 | STAT3, STAT1 |
| OSM | JAK1, JAK2 | STAT3, STAT1 |
| LIF | JAK1, JAK2 | STAT3, STAT1 |
| CNTF | JAK1, JAK2 | STAT3, STAT1 |
| NNT-1/BSF-3 | JAK1, JAK2 | STAT3, STAT1 |
| G-CSF | JAK1, JAK2 | STAT3 |
| CT-1 | JAK1, JAK2 | STAT3 |
| Leptin | JAK2 | STAT4 |
| IL-12 | TYK2, JAK2 | STAT4 |
| IL-23 | undefined | STAT4 |

TABLE 1-continued

| Ligands | JAK Kinases | Stats |
| --- | --- | --- |
| χC family | | |
| IL-2 | JAK1, JAK3 | STAT5, STAT3 |
| IL-7 | JAK1, JAK3 | STAT5, STAT3 |
| TSLP | undefined | STAT5 |
| IL-9 | JAK1, JAK3 | STAT5, STAT3 |
| IL-15 | JAK1, JAK3 | STAT5, STAT3 |
| IL-21 | JAK1, JAK3 | STAT5, STAT3, STAT1 |
| IL-4 | JAK1, JAK3 | STAT6 |
| IL-13 | JAK1 | STAT6, STAT3 |
| IL-3 family | | |
| IL-3 | JAK2 | STAT5 |
| IL-5 | JAK2 | STAT5 |
| GM-CSF | JAK2 | STAT5 |
| Single chain family | | |
| EPO | JAK2 | STAT5 |
| GH | JAK2 | STAT5, STAT3 |
| PRL | JAK2 | STAT5 |
| TPO | JAK2 | STAT5 |
| Receptor tyrosine kinases | | |
| EGF | JAK1, JAK2 | STAT1, STAT3, STAT5 |
| PDGF | JAK1, JAK2 | STAT1, STAT3 |
| CSF-1 | TYK2, JAK1 | STAT1, STAT3, STAT5 |
| HGF | undefined | |
| G-protein coupled receptors | | |
| AT1 | JAK2 | STAT1, STAT2 |

JAK1−/− mice were found to be developmentally similar to the JAK1+/+ although they weighed 40% less than the wild-type and failed to nurse at birth. These pups were not viable and died within 24 hours of birth (Meraz et al Cell, 1998, 373-383). JAK1 deficiency led to reduced number of thymocytes, pre-B cells and mature T and B lymphocytes. TYK2 (−/−) mice, on the other hand, are viable, demonstrating subtle defects in their response to IFN-α/β and IL-10 and profound defects to the response of IL-12 and LPS.

The breast cancer susceptibility protein (BRCA1) acts as a tumor suppressor and contributes to cell proliferation, cycle regulation, as well as DNA damage and repair. BRCA1 (−/−) mice develop normally but die by 7.5 days post embryo suggesting a key role of BRCA1 for development. Mice in which the BRCA1 protein was overexpressed led to inhibition of cell growth and sensitized cells to cytotoxic reagents. In the human proSTATe cancer cell line Du-145 (Gao FEBS Letters 2001, 488, 179-184), enhanced expression of BRCA1 was found to correlate with constitutive activation of STAT3 as well as activation of JAK1 and JAK2. Moreover, antisense oligonucleotides selective for STAT3 led to significant inhibition of cell proliferation and apoptosis in Du-145 cells. This data supports the potential utility of JAK1 and JAK2 inhibitors in the treatment of proSTATe cancer.

Campbell et al (Journal of Biological Chemistry 1997, 272, 2591-2594) as reported that STAT3 is constitutively activated v-Src transformed cells. To test whether STAT3 activation resulted via signaling through the JAK-STAT pathway, three fibroblast cell lines (NIH3T3, Balb/c, and 3Y1) were transformed with v-Src. The level of JAK1 phosphorylation in NIH3T3 cells was markedly increased in cells overexpressed with v-Src or mutant c-Src (Y527F) compared to those in the less transforming c-Src. This result correlated with increased JAK1 enzymatic activity. Similar results were observed with JAK2 albeit to a lesser extent. These results are consistent with constitutive activation of JAK1 and possibly JAK2 which contribute to the hyperactivation of STAT3 in Src-transformed cells.

Asthma is a disease that is increasing in prevalence and results in "airway obstruction, airway hyperresponsiveness, and airway inflammation and remodeling" (Pernis The Journal of Clinical Investigation 2002, 109, 1279-1283). A common cause is the inappropriate immune responses to environmental antigens usually involving CD4+ T helper cells (TH2) which are triggered from cytokines IL-4, IL-5, IL-6, IL-10, and IL-13 which signal through JAK1/JAK3-STAT6 pathway. Th1 cells are thought to be involved with the "delayed-type hypersensitivity responses" which secrete IL-2, IFN-γ, and TNF-β and signal through the JAK2/TYK2-STAT4 pathway. STAT6 (−/−) mice were protected from AHR when challenged with environmental antigens and showed no increase in IgE levels or the quantity of mucous containing cells.

Studies have disclosed an association between an activating JAK2 mutation (JAK2V617F) and myeloproliferative disorders (Gilliland Cancer Cell 2005). The myeloproliferative disorders, a subgroup of myeloid malignancies, are clonal stem cell diseases characterized by an expansion of morphologically mature granulocyte, erythroid, megakaryocyte, or monocyte lineage cells. Myeloproliferative disorders (MPD) include polycythemia vera (PV), essential thrombocythemia (ET), myeloid metaplasia with myelofibrosis (MMM), chronic myelogenous leukemia (CML), chronic myelomonocytic leukemia (CMML), hypereosinophilic syndrome (HES), juvenile myelomonocytic leukemia (JMML) and systemic mast cell disease (SMCD). It has been suggested that abnormalities in signal transduction mechanisms, including constitutive activation of protein tyrosine kinases, initiate MPD.

JAK3 associates with the common gamma chain of the extracellular receptors for the following interleukins: IL-2, IL4, IL-7, IL-9 and IL-15. A JAK3 deficiency is associated with an immune compromised (SCID) phenotype in both rodents and humans. The SCID phenotype of JAK3−/− mammals and the lymphoid cell specific expression of JAK3 are two favorable attributes of a target for an immune suppressant. Data suggests that inhibitors of JAK3 could impede T-cell activation and prevent rejection of grafts following transplant surgery, or to provide therapeutic benefit to patients suffering autoimmune disorders.

SUMMARY OF THE INVENTION

The present invention provides compounds of Formula I

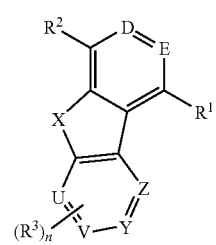

which are inhibitors of kinases, specifically IκB kinases (and block NF-κB activation) and, JAK1, JAK2, JAK3 and TYK2. The invention also provides for compositions comprising such inhibitory compounds and methods of inhibiting kinase activity by administering the compound to a patient in need of treatment for myeloproliferative disorders, cancer or NF-κB-mediated diseases. One embodiment of the invention is illustrated by a compound of formula I, and the pharmaceutically acceptable salts and stereoisomers thereof.

DETAILED DESCRIPTION OF THE INVENTION

In one aspect, the present invention provides compounds of Formula I

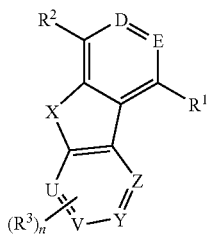

wherein D is CH or N;
E is CH or N;
X is $CH_2$, $NR^4$, O or S;
U is CH or N;
V is CH or N;
Y is CH or N;
Z is CH or N;
$R^1$ is $NR^5R^6$, $CR^5R^6R^7$, $SR^5$ or $OR^5$;
$R^2$ is (C=O)OH, (C=O)$NH_2$, (C=O)$NHR^4$ or heterocyclyl;
$R^3$ is
  (a) hydrogen;
  (b) $C_{1-6}$ alkyl, which is optionally substituted with halo, hydroxyl, amino, phenyl, heterocyclyl, $C_{1-6}$ alkyl or $R^{10}$;
  (c) $C_{2-6}$ alkenyl, which is optionally substituted with halo, hydroxyl, amino, phenyl, heterocyclyl, $C_{1-6}$ alkyl or $R^4$;
  (d) $C_{3-10}$ cycloalkyl, which is optionally substituted with $C_{1-6}$ alkyl, $OR^4$, $NR^8R^4$, phenyl (which is optionally substituted with $C_{1-6}$ alkyl, $OR^4$ or $NR^8R^4$), halo, $R^{10}$ or heterocyclyl;
  (e) —(CO)$R^8$;
  (f) —(CO)—$NR^8R^9$;
  (g) $C_{4-10}$ heterocyclyl, which is optionally substituted on either the carbon or the heteroatom with $C_{1-6}$ alkyl, halo, $R^{10}$, $OR^4$, $NR^8R^4$, phenyl (which is optionally substituted with $C_{1-6}$ alkyl, $OR^4$ or $NR^8R^4$), —(CO)$R^8$ or —(CO)—$NR^8R^9$;
  (h) $OR^4$;
  (i) $NR^8R^4$;
  (j) halo;
  (k) Aryl, which is optionally substituted with one or more groups selected from $C_{1-6}$ alkyl (which is optionally substituted with one to three halo), halo or $R^{10}$;
  (l) Heteroaryl, which is optionally substituted with one or more groups selected from $C_{1-6}$ alkyl (which is optionally substituted with one to three halo), halo or $R^{10}$;
  (m) O-aryl, which is optionally substituted with one or more groups selected from $C_{1-6}$ alkyl, halo or $R^{10}$;
  (n) O—$C_{1-6}$ alkyl, which is optionally substituted with $C_{1-6}$ alky, halo or $R^{10}$; or
  (o) L-A-$R^{10}$;
$R^4$ is
  (a) hydrogen;
  (b) $C_{1-6}$ alkyl, which is optionally substituted with halo, hydroxyl, amino, aryl or heterocyclyl;
  (c) $C_{3-10}$ cycloalkyl, which is optionally substituted with $C_{1-6}$ alkyl, $OR^{11}$, $NR^8R^{11}$, phenyl (which is optionally substituted with $C_{1-6}$ alkyl, $OR^{11}$ or $NR^8R^{11}$), heterocyclyl, aryl or heteroaryl;
  (d) —(CO)$R^8$;
  (e) —(CO)—$NR^8R^9$;
  (f) $C_{4-10}$ heterocyclyl, which is optionally substituted on either the carbon or the heteroatom with $C_{1-6}$ alkyl, $OR^{11}$, $NR^8R^{11}$, phenyl (which is optionally substituted with $C_{1-6}$ alkyl, $OR^{11}$ or $NR^8R^{11}$), heterocyclyl, —(CO)$R^8$ or —(CO)—$NR^8R^9$;
  (g) $OR^{11}$;
  (h) $NR^8R^{11}$;
  (i) Aryl, which is optionally substituted with one to five halo or $R^{10}$;
  (j) Heteroaryl (wherein the heteroaryl has 5 or 6 members in which 1, 2 3 or 4 of the atoms is a heteroatom selected from N, S and O), which is optionally substituted with one to five halo or $R^{10}$;
$R^5$ is
  (a) hydrogen;
  (b) $C_{1-8}$ alkyl, which is optionally substituted with halo, hydroxyl, amino, aryl, cycloalkyl or heterocyclyl;
  (c) $C_{3-10}$ cycloalkyl, which is optionally substituted with $C_{1-6}$ alkyl, ($C_{1-6}$ alkyl)aryl, ($C_{1-6}$ alkyl)$OR^9$, $OR^4$, $NR^8R^4$, phenyl (which is optionally substituted with $C_{1-6}$ alkyl, $OR^4$, $NR^8R^4$, heterocyclyl, —(CO)$R^8$ or —(CO)—$NR^8R^9$);
  (d) —(CO)$R^8$;
  (e) —(CO)—$NR^8R^9$;
  (f) $C_{1-6}$ alkyl(C=O)$NR^8CR^9$(C=O)$NR^8R^9$;
  (g) $C_{4-10}$ heterocyclyl which is optionally substituted on either the carbon or the heteroatom with one to three substituents selected from $C_{1-6}$ alkyl, halo, $OR^4$, $NR^8R^4$, —(CO)$R^8$, (CO)—$NR^8R^9$ or phenyl (which is optionally substituted with $C_{1-6}$ alkyl, $OR^4$, $NR^8R^4$, heterocyclyl, —(CO)$R^8$ or —(CO)—$NR^8R^9$);
$R^6$ is
  (a) hydrogen;
  (b) $C_{1-8}$ alkyl, which is optionally substituted with halo, hydroxyl, amino, aryl, cycloalkyl or heterocyclyl;
  (c) $C_{3-10}$ cycloalkyl, which is optionally substituted with $C_{1-6}$ alkyl, ($C_{1-6}$ alkyl)aryl, ($C_{1-6}$ alkyl)$OR^9$, $OR^4$, $NR^8R^4$, phenyl (which is optionally substituted with $C_{1-6}$ alkyl, $OR^4$, $NR^8R^4$, heterocyclyl, —(CO)$R^8$ or —(CO)—$NR^8R^9$;
  (d) —(CO)$R^8$;
  (e) —(CO)—$NR^8R^9$;
  (f) $C_{1-6}$ alkyl(C=O)$NR^8CR^9$(C=O)$NR^8R^9$;
  (g) $C_{4-10}$ heterocyclyl which is optionally substituted on either the carbon or the heteroatom with one to three substituents selected from $C_{1-6}$ alkyl, halo, $OR^4$, $NR^8R^4$, —(CO)$R^8$, (CO)—$NR^8R^9$ or phenyl (which is optionally substituted with $C_{1-6}$ alkyl, $OR^4$, $NR^8R^4$, heterocyclyl, —(CO)$R^8$ or —(CO)—$NR^8R^9$);
$R^7$ is
  (a) hydrogen;
  (b) $C_{1-6}$ alkyl, which is optionally substituted with halo, hydroxyl, amino, phenyl or heterocyclyl;
  (c) $C_{3-10}$ cycloalkyl, which is optionally substituted with $C_{1-6}$ alkyl, $OR^4$, $NR^8R^4$, phenyl (which is optionally substituted with $C_{1-6}$ alkyl, $OR^4$, $NR^8R^4$, heterocyclyl, —(CO)$R^8$ or —(CO)—$NR^8R^9$);
  (d) $C_{4-10}$ heterocyclyl which is optionally substituted on either the carbon or the heteroatom with $C_{1-6}$ alkyl, $OR^4$, $NR^8R^4$, phenyl (which is optionally substituted with $C_{1-6}$ alkyl, $OR^4$, $NR^8R^4$, heterocyclyl, —(CO)$R^8$ or —(CO)—$NR^8R^9$);

Or $R^5$ and $R^6$, together with the atoms between them, can form a three to ten membered heterocyclic or heteroaryl ring which is optionally substituted with $C_{1-6}$ alkyl, ($C_{1-6}$ alkyl)aryl, ($C_{1-6}$ alkenyl)aryl, ($C_{1-6}$ alkyl)$OR^9$, $OR^4$, $NR^8R^4$, phenyl (which is optionally substituted with $C_{1-6}$ alkyl, $OR^4$, $NR^8R^4$, heterocyclyl, —(CO)$R^8$ or —(CO)—$NR^8R^9$), —(CO)$R^8$; —(CO)—$NR^8R^9$, or heterocyclyl;

$R^8$ is hydrogen or $C_{1-6}$ alkyl, —(CO)$R^{11}$, —(CO)N$(R^{11})_2$;

$R^9$ is hydrogen or $C_{1-6}$ alkyl;

$R^{10}$ is:
(a) hydrogen;
(b) $CO_2R^{11}$;
(c) $C(O)R^{11}$;
(d) $NHR^{11}$;
(e) $NR^{11}R^{12}$;
(f) $NHS(O)_2R^{11}$;
(g) $NHC(O)R^{11}$;
(h) $NHC(O)OR^{11}$;
(i) NH—C=(NH)$NH_2$;
(j) $NHC(O)NH_2$;
(k) $NHC(O)NHR^{11}$;
(l) $NHC(O)NR^{11}R^{12}$;
(m) $NC_{3-6}$cycloalkyl;
(n) $C(O)NHR^{11}$;
(o) $C(O)NR^{11}R^{12}$;
(p) $SO_2NHR^{11}$;
(q) $SO_2NHC(O)R^{12}$; or
(r) $SO_2R^{11}$;

$R^{11}$ is selected from the group consisting of:
(a) hydrogen,
(b) $C_{3-6}$cycloalkyl, which is optionally substituted with aryl, heteroaryl or one to five halo;
(c) $C_{1-6}$alkyl, which is optionally substituted with aryl, heteroaryl, or one to five halo;
(d) Aryl, which is optionally substituted with one to five halo;
(e) Heteroaryl (wherein the heteroaryl has 5 or 6 members in which 1, 2 3 or 4 of the atoms is a heteroatom selected from N, S and O), which is optionally substituted with one to five halo;

$R^{12}$ is selected from the group consisting of:
(a) hydrogen,
(b) $C_{1-6}$alkyl, which is optionally substituted with aryl, heteroaryl or one to five halo;
(c) $C_{3-6}$cycloalkyl, which is optionally substituted with aryl, heteroaryl or one to five halo;
(d) Aryl, which is optionally substituted with one to five halo;
(e) Heteroaryl (wherein the heteroaryl has 5 or 6 members in which 1, 2 3 or 4 of the atoms is a heteroatom selected from N, S and O), which is optionally substituted with one to five halo;

A is absent or is selected from the group consisting of: aryl or heteroaryl (wherein the heteroaryl is a monocyclic ring of 5 or 6 atoms or a bicyclic ring of 9 or 10 atoms in which 1, 2, 3 or 4 of the atoms is a heteroatom selected from N, S and O), wherein said aryl or heteroaryl is optionally substituted with one or more substituents selected from halo, $C_{1-3}$alkyl, —C(O)OH, $CF_3$, —$SO_2C_{1-3}$alkyl, $SO_2NC_{1-3}$alkyl, $SO_2NHC(O)$—$C_{1-3}$alkyl or $N(CH_3)_2$;

L is absent or is selected from the group consisting of: —$(CH_2)_k$—W—, —Z—$(CH_2)_k$—, —C≡C—, —$C_{1-6}$alkyl-, —$C_{3-6}$cycloalkyl- and —$C_{2-5}$alkene-, wherein the alkene is optionally substituted with one or more groups selected from $C_{1-6}$alkyl or $C_{1-6}$cycloalkyl;

W is selected from the group consisting of: O, NH, $NC_{1-6}$alkyl and $S(O)_m$, with the proviso that when W is O, $S(O)_m$, NH or $NC_{1-6}$alkyl and simultaneously A is absent then $R^{10}$ is $CO_2R^{11}$, $COR^{11}$, $CONHR^{11}$ or $CONR^{11}R^{12}$;

k=0, 1, 2, 3, 4 or 5;
m=0, 1 or 2;
n=0, 1, 2 or 3;
or a pharmaceutically acceptable salt or stereoisomer thereof.

In a class of the invention, the present invention provides compounds of Formula II:

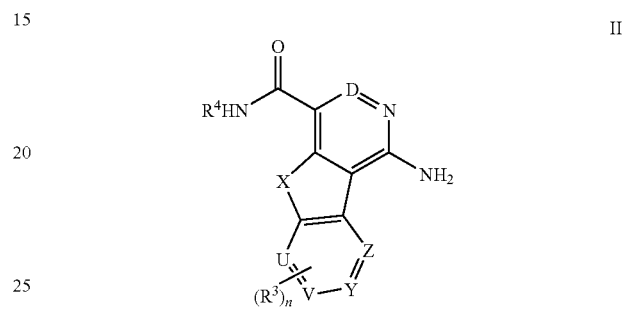

II

Wherein $R^3$ is:
(a) hydrogen,
(b) halo,
(c) $CF_3$,
(d) $C_{1-6}$alkyl, which is optionally substituted with one or more groups selected from $C_{1-6}$ alkyl, halo or $R^{10}$;
(e) $C_{3-6}$cycloalkyl, which is optionally substituted with one or more groups selected from $C_{1-6}$ alkyl, halo or $R^{10}$;
(f) Aryl, which is optionally substituted with one or more groups selected from $C_{1-6}$ alkyl, halo or $R^{10}$;
(g) $C_{4-10}$ heterocyclyl, which is optionally substituted on either the carbon or the heteroatom with $C_{1-6}$ alkyl, halo or $R^{10}$;
(h) L-A-$R^{10}$,
(i) —$OC_{1-6}$alkyl, which is optionally substituted with one or more groups selected from $C_{1-6}$ alkyl, halo or $R^{10}$;
(j) —OAryl, which is optionally substituted with one or more groups selected from $C_{1-6}$ alkyl, halo or $R^{10}$;

$R^4$ is:
(a) hydrogen,
(b) $C_{1-6}$alkyl, which is optionally substituted with aryl or heteroaryl,
(c) $C_{3-6}$cycloalkyl, which is optionally substituted with aryl or heteroaryl,
(d) Aryl, which is optionally substituted with one to five halo or $R^{10}$; or
(e) Heteroaryl (wherein the heteroaryl has 5 or 6 members in which 1, 2 3 or 4 of the atoms is a heteroatom selected from N, S and O), which is optionally substituted with one to five halo or $R^{10}$;

$R^{10}$ is hydrogen or is selected from the group consisting of:
(a) hydrogen;
(b) $C_2R^{11}$;
(c) $C(O)R^{11}$;
(d) $NHR^{11}$;
(e) $NR^{11}R^{12}$;
(f) $NHS(O)_2R^{11}$;
(g) $NHC(O)R^{11}$;
(h) $NHC(O)OR^{11}$;
(i) NH—C=(NH)$NH_2$;

(j) NHC(O)NH$_2$;
(k) NHC(O)NHR$^{11}$;
(l) NHC(O)NR$^{11}$R$^{12}$;
(m) N C$_{3-6}$cycloalkyl;
(n) C(O)NHR$^{11}$;
(o) C(O)NR$^{11}$R$^{12}$;
(p) SO$_2$NHR$^{11}$;
(q) SO$_2$NHC(O)R$^{12}$;

R$^{11}$ is selected from the group consisting of:
  (a) hydrogen;
  (b) C$_{3-6}$cycloalkyl, which is optionally substituted with aryl, heteroaryl, or one to five halo;
  (c) C$_{1-6}$alkyl, which is optionally substituted with aryl, heteroaryl, or one to five halo;
  (d) Aryl, which is optionally substituted with one to five halo; or
  (e) Heteroaryl (wherein the heteroaryl has 5 or 6 members in which 1, 2 3 or 4 of the atoms is a heteroatom selected from N, S and O), which is optionally substituted with one to five halo;

R$^{12}$ is selected from the group consisting of:
  (a) hydrogen,
  (b) C$_{1-6}$alkyl, which is optionally substituted with aryl, hetetoaryl or one to five halo;
  (c) C$_{3-6}$cycloalkyl, which is optionally substituted with aryl, heteroaryl or one to five halo;
  (d) Aryl, which is optionally substituted with one to five halo;
  (e) Heteroaryl (wherein the heteroaryl has 5 or 6 members in which 1, 2 3 or 4 of the atoms is a heteroatom selected from N, S and O), which is optionally substituted with one to five halo;

A is absent or is selected from the group consisting of: a aryl or heteroaryl, wherein the heteroaryl is a ring of 5 or 6 atoms a monocyclic ring of 5 or 6 atoms or a bicyclic ring of 9 or 10 atoms in which 1, 2, 3 or 4 of the atoms is a heteroatom selected from N, S and O, wherein the aryl or heteroaryl is optionally substituted with one or more substituents selected from halo, C$_{1-3}$alkyl, —C(O)OH, CF$_3$, —SO$_2$C$_{1-3}$alkyl, SO$_2$NC$_{1-3}$alkyl, SO$_2$NHC(O)—C$_{1-3}$alkyl and N(CH$_3$)$_2$;

L is absent or is selected from the group consisting of: —(CH$_2$)$_k$—W—, —W—(CH$_2$)$_k$—, —C≡C—, —C$_{1-6}$alkyl-, —C$_{3-6}$cycloalkyl-, —C$_{2-5}$alkene-, wherein the alkene is optionally substituted with one or more substituent group selected from C$_{1-6}$alkyl and C$_{1-6}$cycloalkyl;

X is selected from the group consisting of: O, NH, NC$_{1-6}$alkyl and S;

D is selected from CH and N;

W is selected from the group consisting of: O, NH, NC$_{1-6}$alkyl and S(O)$_m$, with the proviso that when W is O, S(O)$_m$, NH or NC$_{1-6}$alkyl and simultaneously A is absent then R$^{10}$ is CO$_2$R$^{11}$, COR$^{11}$, CONHR$^{11}$ or CONR$^{11}$R$^{12}$;

U is CH or N;
V is CH or N;
Y is CH or N;
Z is CH or N;
k=0, 1, 2, 3, 4 or 5;
m=0, 1 or 2;
n=0, 1, 2 or 3;
or a pharmaceutically acceptable salt or stereoisomer thereof.

In a class of the invention, U is CH; V is CH; Y is CH; and Z is CH.
In a class of the invention, X is NR$^4$ or S.
In a class of the invention, R$^1$ is NR$^5$R$^6$.

Reference to the preferred embodiments set forth above is meant to include all combinations of particular and preferred groups unless stated otherwise.

Specific embodiments of the present invention include, but are not limited to:
1-Amino-8-chloro[1]benzothieno[3,2-c]pyridine-4-carboxamide;
1-Amino-8-phenyl[1]benzothieno[3,2-c]pyridine-4-carboxamide;
1-Amino-6-chloro[1]benzothieno[3,2-c]pyridine-4-carboxamide;
1-Amino-6-phenyl[1]benzothieno[3,2-c]pyridine-4-carboxamide;
1-Amino-7-(trifluoromethyl)-5H-pyrido[4,3-b]indole-4-carboxamide;
1-Amino-8-fluoro-5H-pyrido[4,3-b]indole-4-carboxamide;
8-Fluoro-1-(methylamino)-5H-pyrido[4,3-b]indole-4-carboxamide;
1-(Butylamino)-8-fluoro-5H-pyrido[4,3-b]indole-4-carboxamide;
8-Fluoro-1-(1'H,3H-spiro[2-benzofuran-1,4'-piperidin]-1'-yl)-5H-pyrido[4,3-b]indole-4-carboxamide;
8-fluoro-1-pyrrolidin-1-yl-5H-pyrido[4,3-b]indole-4-carboxamide;
1-(ethylamino)-8-fluoro-5H-pyrido[4,3-b]indole-4-carboxamide;
8-fluoro-1-(propylamino)-5H-pyrido[4,3-b]indole-4-carboxamide;
8-fluoro-1-piperidin-1-yl-5H-pyrido[4,3-b]indole-4-carboxamide;
8-fluoro-1-morpholin-4-yl-5H-pyrido[4,3-b]indole-4-carboxamide;
8-fluoro-1-(methylamino)-5H-pyrido[4,3-b]indole-4-carboxamide;
1-(cyclohexylamino)-8-fluoro-5H-pyrido[4,3-b]indole-4-carboxamide;
1-(benzylamino)-8-fluoro-5H-pyrido[4,3-b]indole-4-carboxamide;
8-fluoro-1-(isobutylamino)-5H-pyrido[4,3-b]indole-4-carboxamide;
8-fluoro-1-(isopropylamino)-5H-pyrido[4,3-b]indole-4-carboxamide;
1-[(cyclohexylmethyl)amino]-8-fluoro-5H-pyrido[4,3-b]indole-4-carboxamide;
1-(butylamino)-8-fluoro-5H-pyrido[4,3-b]indole-4-carboxamide;
8-fluoro-1-(pentylamino)-5H-pyrido[4,3-b]indole-4-carboxamide;
1-(butylamino)-8-fluoro-5H-pyrido[4,3-b]indole-4-carboxamide;
1-(cyclopentylamino)-8-fluoro-5H-pyrido[4,3-b]indole-4-carboxamide;
1-(cyclopentylamino)-8-fluoro-5H-pyrido[4,3-b]indole-4-carboxamide;
1-(cyclooctylamino)-8-fluoro-5H-pyrido[4,3-b]indole-4-carboxamide;
8-fluoro-1-[(4-methylcyclohexyl)amino]-5H-pyrido[4,3-b]indole-4-carboxamide;
8-fluoro-1-[(2-hydroxycyclohexyl)amino]-5H-pyrido[4,3-b]indole-4-carboxamide;
8-fluoro-1-[(2-methylcyclohexyl)amino]-5H-pyrido[4,3-b]indole-4-carboxamide;
8-fluoro-1-[(trans-4-hydroxycyclohexyl)amino]-5H-pyrido[4,3-b]indole-4-carboxamide;
8-fluoro-1-(tetrahydro-2H-pyran-4-ylamino)-5H-pyrido[4,3-b]indole-4-carboxamide;

8-fluoro-1-(heptylamino)-5H-pyrido[4,3-b]indole-4-carboxamide;
8-fluoro-1-[(1,2,2-trimethylpropyl)amino]-5H-pyrido[4,3-b]indole-4-carboxamide;
8-fluoro-1-(hexylamino)-5H-pyrido[4,3-b]indole-4-carboxamide;
8-fluoro-1-(octylamino)-5H-pyrido[4,3-b]indole-4-carboxamide;
1-(2,2-dimethylmorpholin-4-yl)-8-fluoro-5H-pyrido[4,3-b]indole-4-carboxamide;
1-(3,3-difluoropyrrolidin-1-yl)-8-fluoro-5H-pyrido[4,3-b]indole-4-carboxamide;
1-(3,3-difluoropiperidin-1-yl)-8-fluoro-5H-pyrido[4,3-b]indole-4-carboxamide;
8-fluoro-1-(4-hydroxypiperidin-1-yl)-5H-pyrido[4,3-b]indole-4-carboxamide;
ethyl 4-{[4-(aminocarbonyl)-8-fluoro-5H-pyrido[4,3-b]indol-1-yl]amino}piperidine-1-carboxylate;
1-[(1-benzylpiperidin-4-yl)amino]-8-fluoro-5H-pyrido[4,3-b]indole-4-carboxamide;
8-fluoro-1-[3-(hydroxymethyl)piperidin-1-yl]-5H-pyrido[4,3-b]indole-4-carboxamide;
8-fluoro-1-(4-phenyl-3,6-dihydropyridin-1(2H)-yl)-5H-pyrido[4,3-b]indole-4-carboxamide;
1-(4-benzyl-4-hydroxypiperidin-1-yl)-8-fluoro-5H-pyrido[4,3-b]indole-4-carboxamide;
1-(4-benzyl-3,6-dihydropyridin-1(2H)-yl)-8-fluoro-5H-pyrido[4,3-b]indole-4-carboxamide;
1-(4-benzylidenepiperidin-1-yl)-8-fluoro-5H-pyrido[4,3-b]indole-4-carboxamide;
8-fluoro-1-(4-phenylpiperidin-1-yl)-5H-pyrido[4,3-b]indole-4-carboxamide;
8-fluoro-1-(3-hydroxypiperidin-1-yl)-5H-pyrido[4,3-b]indole-4-carboxamide;
8-fluoro-1-(2-phenylpiperidin-1-yl)-5H-pyrido[4,3-b]indole-4-carboxamide;
8-fluoro-1-{[(1S,2R)-2-(methoxymethyl)cyclopentyl]amino}-5H-pyrido[4,3-b]indole-4-carboxamide;
8-fluoro-1-{[(1R)-1,2,2-trimethylpropyl]amino}-5H-pyrido[4,3-b]indole-4-carboxamide;
8-fluoro-1-{[(1S)-1,2,2-trimethylpropyl]amino}-5H-pyrido[4,3-b]indole-4-carboxamide;
N-[4-(aminocarbonyl)-8-fluoro-5H-pyrido[4,3-b]indol-1-yl]-3-methyl-D-valyl-N,3-dimethylvalinamide;
N-[4-(aminocarbonyl)-8-fluoro-5H-pyrido[4,3-b]indol-1-yl]-3-methyl-L-valyl-N,3-dimethylvalinamide;
1-(bicyclo[2.2.1]hept-2-ylamino)-8-fluoro-5H-pyrido[4,3-b]indole-4-carboxamide;
1-{[(1R)-1-cyclohexylethyl]amino}-8-fluoro-5H-pyrido[4,3-b]indole-4-carboxamide;
8-fluoro-1-(3-phenylpiperidin-1-yl)-5H-pyrido[4,3-b]indole-4-carboxamide;
8-fluoro-1-(3-phenylpiperidin-1-yl)-5H-pyrido[4,3-b]indole-4-carboxamide;
8-fluoro-1-[(1-hydroxypropyl)amino]-5H-pyrido[4,3-b]indole-4-carboxamide;
8-fluoro-1-(1'H,3H-spiro[2-benzofuran-1,4'-piperidin]-1'-yl)-5H-pyrido[4,3-b]indole-4-carboxamide;
1-Amino-5H-pyrido[4,3-b]indole-4-carboxamide;
1-Amino-8-bromo-5H-pyrido[4,3-b]indole-4-carboxamide;
1-Amino-7-bromo[1]benzothieno[3,2-c]pyridine-4-carboxamide;
1-Amino-7-[4-(methylsulfonyl)phenyl][1]benzothieno[3,2-c]pyridine-4-carboxamide;
1-Amino-7-[4-(trifluoromethyl)phenyl][1]benzothieno[3,2-c]pyridine-4-carboxamide;
1-Amino[1]benzothieno[3,2-c]pyridine-4,7-dicarboxamide;
1-Amino-7-[(E)-2-(4-fluorophenyl)vinyl][1]benzothieno[3,2-c]pyridine-4-carboxamide;
1-Amino-7-[3-(trifluoromethyl)phenyl][1]benzothieno[3,2-c]pyridine-4-carboxamide;
1-Amino-7-(3-isopropylphenyl)[1]benzothieno[3,2-c]pyridine-4-carboxamide;
1-Amino-7-pyridin-3-yl[1]benzothieno[3,2-c]pyridine-4-carboxamide;
1-Amino-7-phenyl[1]benzothieno[3,2-c]pyridine-4-carboxamide;
1-Amino-7-{4-[(dimethylamino)methyl]phenyl}[1]benzothieno[3,2-c]pyridine-4-carboxamide;
Methyl 1-amino-4-(aminocarbonyl)[1]benzothieno[3,2-c]pyridine-7-carboxylate;
1-Amino-4-(aminocarbonyl)[1]benzothieno[3,2-c]pyridine-7-carboxylic acid;
1-Amino-7-(trifluoromethyl)[1]benzothieno[3,2-c]pyridine-4-carboxamide;
1-Amino-6-chloro-5H-pyrido[4,3-b]indole-4-carboxamide;
1-Amino-5-methyl-7-(trifluoromethyl)-5H-pyrido[4,3-b]indole-4-carboxamide;
1-Amino-7-chloro-5H-pyrido[4,3-b]indole-4-carboxamide;
1-Amino-7-pyridin-3-yl-5-H-pyrido[4,3-b]indole-4-carboxamide;

or a pharmaceutically acceptable salt or stereoisomer thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

In addition, the compounds disclosed herein may exist as tautomers and both tautomeric forms are intended to be encompassed by the scope of the invention, even though only one tautomeric structure is depicted. Imidazoles exist as a mixture of 1H/2H tautomers. The tautomeric forms of the imidazole moiety are also within the scope of the instant invention.

When any variable (e.g. $R^3$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to four substituents, and the more preferred embodiment will have from zero to three substituents.

As used herein, "alkyl" is intended to include both branched and straight-chain saturated aliphatic hydrocarbon groups having the specified number of carbon atoms. For example, $C_1$-$C_{10}$, as in "($C_1$-$C_{10}$)alkyl" is defined to include groups having 1, 2, 3, 4, 5, 6, 7, 8, 9 or 10 carbons in a linear or branched arrangement. For example, "($C_1$-$C_{10}$)alkyl" specifically includes methyl, ethyl, n-propyl, i-propyl, n-butyl, t-butyl, i-butyl, pentyl, hexyl, heptyl, octyl, nonyl, decyl, and so on.

The term "cycloalkyl" means a monocyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on.

The term "haloalkyl" means an alkyl radical as defined above, unless otherwise specified, that is substituted with one to five, preferably one to three halogen. Representative examples include, but are not limited to trifluoromethyl, dichloroethyl, and the like.

"Alkoxy" represents either a cyclic or non-cyclic alkyl group of indicated number of carbon atoms attached through an oxygen bridge. "Alkoxy" therefore encompasses the definitions of alkyl and cycloalkyl above.

In certain instances, substituents may be defined with a range of carbons that includes zero, such as ($C_0$-$C_6$)alkyl-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydro-naphthyl, indanyl and biphenyl. In cases where the aryl substituent is bicyclic and one ring is non-aromatic, it is understood that attachment is via the aromatic ring.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively. Such heteroaryl moieties for substituent Q include but are not limited to: 2-benzimidazolyl, 2-quinolinyl, 3-quinolinyl, 4-quinolinyl, 1-isoquinolinyl, 3-isoquinolinyl and 4-isoquinolinyl.

The term "heterocycle" or "heterocyclyl" as used herein is intended to mean a 3- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzoimidazolonyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As appreciated by those of skill in the art, "halo" or "halogen" as used herein is intended to include chloro (Cl), fluoro (F), bromo (Br) and iodo (I).

Included in the instant invention is the free form of compounds of the instant invention, as well as the pharmaceutically acceptable salts and stereoisomers thereof. Some of the isolated specific compounds exemplified herein are the protonated salts of amine compounds. The term "free form" refers to the amine compounds in non-salt form. The encompassed pharmaceutically acceptable salts not only include the isolated salts exemplified for the specific compounds described herein, but also all the typical pharmaceutically acceptable salts of the free form of compounds of the instant invention. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

Thus, pharmaceutically acceptable salts of the compounds of this invention include the conventional non-toxic salts of the compounds of this invention as formed by reacting a basic instant compound with an inorganic or organic acid. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic (TFA) and the like.

When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Utility

Compounds described in this invention are inhibitors of kinases, specifically IκB kinases, JAK1, JAK2, JAK3 and TYK2.

Compounds described in this invention are inhibitors of IKKα and IKKβ that prevent the activation of NF-κB. The ability of the compounds described in this invention to inhibit the activity of IκB kinases and prevent activation of NF-κB makes them useful for preventing, halting and reversing undesirable symptoms caused by NF-κB activation in a *mammalian*, especially human subject. The inhibition of NF-κB activation indicates that the compounds and pharmaceutical compositions thereof are useful to treat, prevent, or ameliorate in mammals and especially humans: respiratory conditions, inflammatory conditions, metabolic conditions, allergic conditions, neurodegenerative conditions, neoplastic conditions, cardiovascular conditions as well as immune and autoimmune diseases.

Broad evidence is available that suggests a central role of NF-κB in many inflammatory disorders including airway inflammation and asthma ((Yang L et al., J Exp Med 188 (1998), 1739-1750), (Hart L A et al. Am J Respir Crit Care Med 158 (1998), 1585-1592), (Stacey M A et al., Biochem Biophys Res Commun 236 (1997), 522-526) (Barnes P and Adcock I M, Trends Pharmacol Sci 18 (1997), 46-50)).

It has been shown that glucocorticoids, which are by far the most effective treatment for asthma, inhibit airway inflammation by directly interacting with and inhibiting the activity of the transcription factors NF-κB and activator protein-1 (AP-1) ((Barnes P (1997) Pulmon Pharmacol Therapeut 10, 3-19) and (Dumont A et al. (1998) Trends Biochem Sci 23, 233-235)).

Several studies imply that NF-κB plays an essential role in neoplastic transformation. For example, NF-κB is associated with cell transformation in vitro and in vivo as a result of gene overexpression, amplification, rearrangement, or translocation (Mercurio, F., and Manning, A. M. (1999) Oncogene, 18:6163-6171). In certain human lymphoid tumor cells, the genes of NF-κB family members are rearranged or amplified. Its possible involvement in cancer pathology is also disclosed in Mayo, M. W., Baldwin A. S. (2000) Biochmica et Biophysica Acta 1470 M55-M62. Mayo M. W. et al., discloses the inhibition of NF-κB results in the blockage of the initiation and/or progression of certain cancers, particularly colorectal cancer.

Finally, NF-κB may also be involved in the regulation of neuronal cell death. It has been shown that NF-.kappa.B becomes activated and promotes cell death in focal cerebral ischemia Nature medicine Vol. 5 No. 5, May 1999).

Extensive research during the past years led to the identification of an I-κB kinase (IKK) complex as being responsible for the signal-induced I-κB phosphorylation ((Mercurio, F., and Manning, A. M. (1999) Current Opinion in Cell Biology, 11, 226-232), (Mercurio, F., and Manning, A. M. (1999) Oncogene, 18, 6163-6171), (Barnkett, M., and Gilmore T. D. (1999) Oneogene 18, 6910-6924), (Zandi, E., and Karin, M., (1999) 19, 4547-4551), (Israel, A., (2000) Trends in Cell Biology 10, 129-133), and (Hatada, E. N, et al. (2000) Current Opinion in Immunology, 12, 52-58)). This complex is most likely the site of integration of all of the different pro-inflammatory stimuli leading to NF-κB activation. The IKK-complex (molecular weight 700-900 kDa) is composed of various proteins including two homologous I.kappa.B Iinases, called IKKα and IKKβ, and a regulatory subunit IKKγ (NEMO), which preferentially interacts with IKKβ. Targeted gene disruption studies have demonstrated that IKKβ and IKKγ are necessary for activation of NF-κB by pro-inflammatory stimuli ((Li et al., (1999) Science 284, 321-325), (Tanaka et al., (1999) Immunity 10: 421-429), (Makris et al., (2000) Mol. Cell 5, 969-979), (Schmidt-Supprian et al., (2000) Mol. Cell 5, 981-992), Rudolph et al., (2000) Genes Dev. 14: 854-862)).

IKKβ is a 756 amino acid serine-threonine kinase showing 52% identity to the same domain structure as IKKα. ((Mercurio F et al (1997) Science 278, 860-866.), (Woronicz J D et al. (1997) Science 278, 866-869.), (Zandi E et al. (1997) Cell 91, 243-252.). IKKβ. forms homo-dimers and hetero-dimers with IKKα in vitro and in cells. Recombinant IKKβ phosphorylates. IκBα and IκBβ. at specific serine residues with equal efficacy (Li J et al. (1998) J Biol Chem 273, 30736-30741.), (Zandi E, Chen Y, Karin M (1998) Science 281, 1360-1363.). IKKβ shows a higher constitutive kinase activity as compared to IKKα. This is in agreement with data suggesting that over-expression of IKKβ activates the transcription of a NF-κB-dependent reporter gene with a higher efficacy as compared to IKKα. IKKβ has been shown to be activated in various cell lines or fresh human cells in response to various stimuli including TNFα, IL-1β, LPS, anti-CD3/anti-CD28 co-stimulation, protein kinase C and calcineurin, B-cell receptor/CD40 ligand stimulation and vanadate. IKKβ is activated in fibroblast-like synoviocytes (FLS) isolated from the synovium of patients suffering from rheumatoid arthritis or osteoarthritis (Zandi E et al. (1997) Cell 91, 243-252.), (O'Connell M A et al. (1998) J Biol Chem 273, 30410-30414.), Kempiak S J et al. (1999) J Immunol 162, 3176-3187.). Furthermore, IKKβ can be activated by the structurally related upstream kinases MEKK-1, MEKK-3 and TAK1, most likely through phosphorylation of specific serine residues within the T-loop (activation loop) and by certain protein kinase C isoforms ((Nakano H et al. (1998) Proc Natl Acad Sci USA 95, 3537-3542.), (Lee F S et al. (1998) Proc Natl Acad Sci USA 95, 9319-9324.), (Nemoto S et al (1998) Mol Cell Biol 18, 7336-7343.), (Lallena M J et al. (1999) Mol Cell Biol 19, 2180-2188.)). NIK has also been demonstrated to activate the IKK complex but appears to have a preference for IKKα over IKKβ (Senftleben et al., 2001). A catalytically inactive mutant of IKKβ has been shown to inhibit activation of NF-κB by TNFα, IL-1β, LPS, anti-CD3/anti-CD28 stimulation ((Mercurio F et al. (1997) Science 278, 860-866.), (Woronicz J D et al. (1997) Science 278, 866-869.)). The same effects are observed when MEKK1 or NIK are overexpressed. Furthermore, MEKK3-deficient cells and cells exhibiting reduced activity of TAK1 from knockdown with RNAi show significantly reduced IKKβ activation upon stimulation with TNFα. Additionally, IKKβ mutations in the activation loop inhibited IL-1β and TNFα-dependent signaling (Delhase M et al. (1999) Science 284, 309-313.). Based on the experimental results described above, there is clear-cut evidence for a pivotal involvement of IKKβ in various pathways leading to NF-κB activation.

Accordingly, another aspect of the invention provides a method of treating or preventing NF-κB-mediated disease comprising administering to a *mammalian* patient in need of such treatment a compound described in this invention in an amount which is effective for treating or preventing said NF-κB-mediated disease. Examples of diseases, and disorders where inhibition of NF-κB activation would be a valuable treatment method include but not limited to asthma, COPD, tuberculosis, chronic bronchitis, silicosis, rheumatoid arthritis, osteoarthritis, ankylosing spongylitis, inflammatory bowel disease, including Crohn's disease, systemic lupus erythematosus, Sjörgren's syndrome, dermatitis, psoriasis, psoriatic arthritis, atherosclerosis, hypertension, cardiac hypertrophy, myocardial infarction, unstable angina, congestive heart failure, diabetes, diabetic nephropathy, nephritis, osteoporosis, sepsis, reperfusion injury, stroke, Alzheimer's disease, multiple sclerosis, neuropathic pain, cancer, immune complex diseases, AIDS, cachexia, rhinitis, including allergic rhinitis, atopic dermatitis, hives, conjunctivitis, glaucoma, vernal catarrh, diabrotic colitis, systemic inflammatory response syndrome, polymyositis, dermatomyositis, Polyaritis nodoa; mixed connective tissue disease, bone resorption disease, Reiter's syndrome, toxic shock and gout.

The compounds of the present invention are also inhibitors of JAK2 and are therefore useful to treat or prevent myeloproliferative disorders or cancer in mammals, preferably humans.

An embodiment of the invention provides a method for inhibiting wild type or mutant JAK2 tyrosine kinase, comprising administering to the mammal a therapeutically effective amount of any of the compounds or any of the pharmaceutical compositions described above. Another embodiment of the invention provides a method for inhibiting JAK2V617F tyrosine kinase, comprising administering to the mammal a therapeutically effective amount of any of the compounds or any of the pharmaceutical compositions described above.

The compounds, compositions and methods provided herein are particularly deemed useful for the treatment of myeloproliferative disorder(s). Myeloproliferative disorders that may be treated include polycythemia vera (PV), essential thrombocythemia (ET), myeloid metaplasia with myelofibrosis (MMM), chronic myelogenous leukemia (CML), myelomonocytic leukemia (CMML), hypereosinophilic syndrome (HES), juvenile myelomonocytic leukemia (JMML), and systemic mast cell disease (SMCD).

It is known in the literature that inhibitors of JA2 are useful in the treatment and/or prevention of myeloproliferative disorders. See, e.g., Tefferi, A. and Gilliland, D. G. *Mayo Clin. Proc.* 80(7): 947-958 (2005); Fernandez-Luna, J. L. et al. *Haematologica* 83(2): 97-98 (1998); Harrison C. N. *Br. J. Haematol.* 130(2): 153-165 (2005); *Leukemia* (2005) 19, 1843-1844; and Tefferi, A. and Barbi, T. *Mayo Clin. Proc.* 80(9): 1220-1232 (2005).

The compounds, compositions and methods provided herein are also deemed useful for the treatment of cancer. Cancers that may be treated by the compounds, compositions and methods of the invention include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoima, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

Cancers that may be treated by the compounds, compositions and methods of the invention include, but are not limited to: breast, prostate, colon, colorectal, lung, brain, testicular, stomach, pancrease, skin, small intestine, large intestine, throat, head and neck, oral, bone, liver, bladder, kidney, thyroid and blood.

Cancers that may be treated by the compounds, compositions and methods of the invention include: breast, prostate, colon, ovarian, colorectal and lung.

Cancers that may be treated by the compounds, compositions and methods of the invention include: breast, colon, (colorectal) and lung.

Cancers that may be treated by the compounds, compositions and methods of the invention include: lymphoma and leukemia.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, including humans, either alone or, in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavouring agents, -preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the instant invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the instant invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When a composition according to this invention is administered into a human subject, the daily dosage will normally be determined by the prescribing physician with the dosage generally varying according to the age, weight, and response of the individual patient, as well as the severity of the patient's symptoms.

In an embodiment, a suitable amount of an inhibitor of JAK2 is administered to a mammal undergoing treatment for cancer. Administration occurs in an amount of inhibitor of between about 0.1 mg/kg of body weight to about 60 mg/kg of body weight per day, or between 0.5 mg/kg of body weight to about 40 mg/kg of body weight per day. Another therapeutic dosage that comprises the instant composition includes from about 0.01 mg to about 1000 mg of inhibitor of JAK2. In another embodiment, the dosage comprises from about 1 mg to about 1000 mg of inhibitor of JAK2.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy. The instant compounds are also useful in combination with other therapeutic ingredients or adjuvants that include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), ix) M2/M3 antagonists, x) PDE4 inhibitors, xi) P38MAPK inhibitors, and xii) EP4 receptor agonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylomithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, the epothilones (see for example U.S. Pat. Nos. 6,284,781 and 6,288,237) and BMS188797. In an embodiment the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-k1]acridine-2-(6H)propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino] ethyl]-5-[4-hydro0xy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]-phenanthridinium, 6,9-bis[(2-aminoethyl)amino] benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c]quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitors" refers to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911, 165, 4,929,437, 5,189,164, 5,118,853, 5,290,946 and 5,356, 896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. No. 5,420,245, U.S. Pat. No. 5,523,430, U.S. Pat. No. 5,532,359, U.S. Pat. No. 5,510,510, U.S. Pat. No. 5,589,485, U.S. Pat. No. 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer*, Vol. 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including non steroidal anti-inflammatories (NSSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop. Vol.* 313, p. 76 (1995); *J. Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature*, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refer to compounds that inhibit protein kinases that transduce cell cycle checkpoint signals, thereby sensitizing the cancer cell to DNA damaging agents. Such agents include inhibitors of ATR, ATM, the CHK11 and CHK12 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAID's are directed to the use of NSAID's which are potent COX-2 inhibiting agents. For purposes of this specification an NSAID is potent if it possesses an $IC_{50}$ for the inhibition of COX-2 of 1 μM or less as measured by cell or microsomal assays.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. No. 5,474,995, U.S. Pat. No. 5,861,419, U.S. Pat. No. 6,001,843, U.S. Pat. No. 6,020,343, U.S. Pat. No. 5,409,944, U.S. Pat. No. 5,436,265, U.S. Pat. No. 5,536,752, U.S. Pat. No. 5,550,142, U.S. Pat. No. 5,604,260, U.S. Pat. No. 5,698,584, U.S. Pat. No. 5,710,140, WO 94/15932, U.S. Pat. No. 5,344,991, U.S. Pat. No. 5,134,142, U.S. Pat. No. 5,380,738, U.S. Pat. No. 5,393,790, U.S. Pat. No. 5,466,823,U.S. Pat. No. 5,633,272 and U.S. Pat. No. 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: parecoxib, BEXTRA® and CELEBREX® or a pharmaceutically acceptable salt thereof.

Other examples of angiogenesis inhibitors include, but are not limited to, endostatin, ukrain, ranpimase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v \beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro4-fluorophenylamino)-7-methoxy-6-[3-(4-morpholinyl)propoxyl]quinazoline, N-(3-ethynylphenyl)-6,7-bis (2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-k1]pyrrolo [3,4-i][1,6]benzodiazocin-1-one, SH268, genistein, STI571, CEP2563, 4-(3-chloropbenylamino)-5,6-dimetbyl-7H-pyrrolo[2,3-d]pyrimidinemethane sultanate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malingnancies. PPAR-γ and PPAR-δ are the nuclear peroxisome proliferator-activated receptors γ and δ. The expression of PPAR-γ on endothelial cells and its involvement in angiogenesis has been reported in the literature (see *J. Cardiovasc. Pharmacol.* 1998; 31:909-913; *J. Biol. Chem.* 1999; 274: 9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy)phenoxy)propoxy)-2-ethylchromane-2-carboxylic acid (disclosed in U.S. Ser. No. 60/235,708 and 60/244,697).

Another embodiment of the instant invention is the use of the presently disclosed compounds in combination with gene therapy for the treatment of cancer. For an overview of genetic strategies to treating cancer see Hall et al (*Am. J. Hum. Genet.* 61:785-789, 1997) and Kufe et al (Cancer Medicine, 5th Ed, pp 876-889, B C Decker, Hamilton 2000). Gene therapy can be used to deliver any tumor suppressing gene. Examples of such genes include, but are not limited to, p 53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (*J. Immunol.* 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar).

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurolinin-1 receptor antagonist, a 5HT3 receptor antagonist and a corticosteroid is disclosed for the treatment or prevention of emesis that may result upon administration of the instant compounds.

Neurokinin-1 receptor antagonists of use in conjunction with the compounds of the present invention are fully described, for example, in U.S. Pat. Nos. 5,162,339, 5,232,929, 5,242,930, 5,373,003, 5,387,595, 5,459,270, 5,494,926, 5,496,833, 5,637,699, 5,719,147; European Patent Publication Nos. EP 0 360 390, 0 394 989, 0 428 434, 0 429 366, 0 430 771, 0 436 334, 0 443 132, 0 482 539, 0 498 069, 0 499 313, 0 512 901, 0 512 902, 0 514 273, 0 514 274, 0 514 275, 0 514 276, 0 515 681, 0 517 589, 0 520 555, 0 522 808, 0 528 495, 0 532 456, 0 533 280, 0 536 817, 0 545 478, 0 558 156, 0 577 394, 0 585 913, 0 590 152, 0 599 538, 0 610 793, 0 634 402, 0 686 629, 0 693 489, 0 694 535, 0 699 655, 0 699 674, 0 707 006, 0 708 101, 0 709 375, 0 709 376, 0 714 891, 0 723 959, 0 733 632 and 0 776 893; PCT International Patent Publication Nos. WO 90/05525, 90/05729, 91/09844, 91/18899, 92/01688, 92/06079, 92/12151, 92/15585, 92/17449, 92/20661, 92/20676, 92/21677, 92/22569, 93/00330, 93/00331, 93/01159, 93/01165, 93/01169, 93/01170, 93/06099, 93/09116, 93/10073, 93/14084, 93/14113, 93/18023, 93/19064, 93/21155, 93/21181, 93/23380, 93/24465, 94/00440, 94/01402, 94/02461, 94/02595, 94/03429, 94/03445, 94/04494, 94/04496, 94/05625, 94/07843, 94/08997, 94/10165, 94/10167, 94/10168, 94/10170, 94/11368, 94/13639, 94/13663, 94/14767, 94/15903, 94/19320, 94/19323, 94/20500, 94/26735, 94/26740, 94/29309, 95/02595, 95/04040, 95/04042, 95/06645, 95/07886, 95/07908, 95/08549, 95/11880, 95/14017, 95/15311, 95/16679, 95/17382, 95/18124, 95/18129, 95/19344, 95/20575, 95/21819, 95/22525, 95/23798, 95/26338, 95/28418, 95/30674, 95/30687, 95/33744, 96/05181, 96/05193, 96/05203, 96/06094, 96/07649, 96/10562, 96/16939, 96/18643, 96/20197, 96/21661, 96/29304, 96/29317, 96/29326, 96/29328, 96/31214, 96/32385, 96/37489, 97/01553, 97/01554, 97/03066, 97/08144, 97/14671, 97/17362, 97/18206, 97/19084, 97/19942 and 97/21702; and in British Patent Publication Nos. 2 266 529, 2 268 931, 2 269 170, 2 269 590, 2 271 774, 2 292 144, 2 293 168, 2 293 169, and 2 302 689. The preparation of such compounds is fully described in the aforementioned patents and publications, which are incorporated herein by reference.

In an embodiment, the neurokinin-1 receptor antagonist for use in conjunction with the compounds of the present invention is selected from: 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, or a pharmaceutically acceptable salt thereof, which is described in U.S. Pat. No. 5,719,147.

A compound of the instant invention may also be administered with an agent useful in the treatment of anemia. Such an anemia treatment agent is, for example, a continuous eythropoiesis receptor activator (such as epoetin alfa).

A compound of the instant invention may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention may also be administered with an immunologic-enhancing drug, such as levamisole, isoprinosine and Zadaxin.

A compound of the instant invention may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention may also be useful for treating or preventing breast cancer in combination with aromatase inhibitors. Examples of aromatase inhibitors include but are not limited to: anastrozole, letrozole and exemestane.

A compound of the instant invention may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139).

A compound of the instant invention may also be useful for treating or preventing cancer in combination with inhibitors of Akt. Such inhibitors include compounds described in, but not limited to, the following publications: WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734,188, 60/652,737, 60/670,469.

A compound of the instant invention may also be useful for treating or preventing cancer in combination with PARP inhibitors.

A compound of the instant invention may also be useful for treating cancer in combination with the following therapeutic agents: abarelix (Plenaxis Depot®); aldesleukin (Proline®); Aldesleukin (Proleuldin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®); BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®M); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®D); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); and zoledronate (Zometa®).

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

Also included in the scope of the claims is a method of treating cancer that comprises administering a therapeutically effective amount of a compound of the instant invention in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

The instant invention also includes a pharmaceutical composition useful for treating or preventing cancer that comprises a therapeutically effective amount of a compound of the instant invention and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase inhibitors, agents that interfere with receptor tyrosine kinases (RTKs), an agent that interferes with a cell cycle checkpoint and any of the therapeutic agents listed above.

All patents, publications and pending patent applications identified are hereby incorporated by reference.

Assays for the Evaluation of Biological Activity

The utility of the compounds of the instant invention can be demonstrated in a number of ways known to those skilled in the art, including using the following assays to establish their inhibitory activity in vitro.

Homogenous Time Resolved Fluorescence (HTRF) Assay for IKK Inhibitory Activity.

This enzyme assay monitors the inhibitory potency of the compounds of Formula I and II to block the catalytic activity of IKKα and IKKβ in vitro. The full-length coding sequences of IKKα and IKKβ are subcloned into the appropriate site of pVL1393 (Pharmingen) to construct a baculovirus transfer vector. Recombinant baculovirus was generated from vector-transfected SF9 cells (BaculoGold™, Invitrogen), cloned, amplified and used to infect SF9 cells for protein production. Recombinant His-tagged IKKα and IKKβ are isolated from the Baculovirus-infected SF9 cells expressing the fusion protein.

An HTRF assay in a 384-well format established on a Biomek FX is used to test the inhibitory activity of compounds of Formula I. The peptide substrate, biotin-DRHDS-GLDSMKDE (SEQ. ID.: 1) used to assay IKKβ activity spans residues 28 to 40 of IκBα and was custom synthesized (Synpep). A biotinylated peptide that spans residues 21 to 40 of Iκbα, KKKKERLLDDRHDSGLDSMKDEE (SEQ. ID.: 2), was used as substrate for IKKα. The assay conditions used to test inhibitory activity of compounds against IKKβ comprises 110 nM recombinant enzyme, 150 nM peptide substrate, 6 μM ATP, 10% (v/v) DMSO, 15 mM MgCl$_2$, 2 mM DTT, and 50 mM Tris/HCl at a pH of 7.5. For IKKα, the reaction mixture comprises 125 nM recombinant enzyme, 400 nM peptide substrate, 6 μM ATP, 10% (v/v) DMSO, 15 mM MgCl$_2$, 2 mM DTT, and 50 mM Tris/HCl at a pH of 7.5. The kinase reaction proceeds for 20 and 35 min for IKKα and IKKβ respectively and then it is quenched by the addition of EDTA to a final concentration of 20 mM. Following completion of the kinase assay, 5 μL of the reaction is quantified by HTRF with a 5 μL detection mix comprising 40 mM HEPES, 100 mM KF, 27.7 nM Streptavidin-tagged-XL665-XLent (CIS-Bio international), 0.3 nM anti-phospho-IκBα mAb (Cell signaling), 1 nM anti-phospho peptide antibody conjugated to Eu (CIS-Bio international). Following excitation at 330 nm, the 665 nm/615 nm emission ratio is measured after a 2-hour incubation at room temperature to quantify the FRET signal.

Whole Cell Assays to Determine IKK Inhibitors

I. Cytoplasmic to Nuclear Translocation Assay

This assay monitors a key regulatory step in NF-κB activation: IKK-dependent translocation of NF-κB from the cytoplasm to the nucleus. The assay measures the translocation of the p65 subunit of NF-κB from the cytoplasm to the nucleus following stimulation of human umbilical vein endothelial cells (HUVECs) with a pro-inflammatory cytokine, IL-1β. Briefly, HUVEC cells are plated in a 96-well plate and incubated for 18-24 hr in EGM-2 media (Clonetics). The cells are treated with the test compound for 60 min at 37° C. prior to stimulation with IL-1β for 30 min. Next, the culture media is aspirated, the cells are fixed and then permeabilized. A primary anti-p65 antibody is then added to detect the NF-κB subunit which is followed by staining with a secondary antibody conjugated with Alexa Fluor-488. The extent of p65 nuclear translocation is quantified by subtracting the amount of p65 fluorescent signal remaining in the cytoplasm from the nuclear signal on a Cellomics Arrayscan II instrument.

II. IL-1β-Induced IL-8 Release from A549 Cells

Inhibition of IKK activity in lung epithelial cells have been demonstrated to block NF-κB-dependent cytokine production and lung inflammation in rodent models. IL-8, an NF-κB-driven chemokine, is a chemotactic factor for neutrophil recruitment, a process observed during inflammatory and immune responses. This assay monitors the production of IL-8 from A549 lung epithelial cell line as a functional consequence of NF-κB activation. Briefly, A549 cells are plated in a 96-well plate and incubated for 18-24 hr in RPMI medium with 2% FBS. The cells are treated with the test compound for 15 min at 37° C. with 5% CO$_2$ prior to stimulation with IL-1β, for 18-24 hr. The supernatant is recovered following centrifugation of the cell culture at 1500×g for 10 min. The extent of IL-8 production is quantified by following the manufacturer's suggestions in an ELISA assay (Biosource). In this assay, the compounds of formula I demonstrate an IC50 for the inhibition of less than 1.0 μM. The following results have been obtained for compounds the compounds identified:

| Example # | IKKβIC$_{50}$ (μM) |
|---|---|
| 3 | ≦1.0 |
| 4 | ≦1.0 |
| 5 | ≦0.1 |
| 6 | ≦1.0 |
| 8 | ≦1.0 |
| 9 | ≦0.5 |
| 11 | ≦1.0 |
| 16 | ≦0.5 |
| 21 | ≦0.5 |
| 25 | ≦0.1 |

III. LPS-Induced TNFα Production in Monocytes

TNFα, an NF-κB-driven cytokine, is a key pro-inflammatory molecule that has been demonstrated to be involved in the pathogenesis of a number of inflammatory disorders. This assay monitors the production of TNFα following stimulation of human monocytes with LPS. Human monocytes are isolated from blood donated by healthy volunteers. The blood, collected into CPT vacutainers containing citrate, is centrifuged at 1600×g for 30 min at room temperature to isolate the mononuclear cell fraction. The isolated cells are washed in PBS followed by centrifugation (500×g for 10 min then twice at 200×g for 10 min). The isolated cells are suspended in serum-free RPMI and plated at $0.5 \times 10^6$ cells per well in a 96-well plate and incubated at 37° C. with 5% $CO_2$ for 60 min. Following incubation, the adhered cells are washed in PBS and cultured with 2% HIS-RPMI. The test compound is incubated with the cells at a final DMSO concentration of 0.5% (v/v) for 15 min prior to stimulation with LPS at a final concentration of 1 μg/μL. The reaction mixture is incubated for 20 hr at 37° C. with 5% $CO_2$. The supernatant of the reaction mixture is collected by centrifugation and the amount of TNFα produced is measured by ELISA; the manufacturer's instructions (Biosource) are followed.

Whole Blood Assays to Measure TNFα Production Following LPS Stimulation

I. Human Whole Blood Assay

TNFα, an NF-κB-driven cytokine, is a key pro-inflammatory molecule that has been demonstrated to be involved in the pathogenesis of a number of inflammatory disorders. This assay monitors the production of TNFα following stimulation of human blood with LPS. Blood collected from healthy volunteers (in heparinized vacutainer tubes) is plated into Tall Marsh mini-tubes and pre-incubated with varying concentrations of the test compound for 15 min at 37° C. with 5% $CO_2$. LPS is then added as a stimulus to a final concentration of 1 ng/μL. Following incubation at 37° C. with 5% $CO_2$ for 24 hr, the blood is centrifuged at 1500×g for 10 min at 4° C. to obtain the plasma. The TNFα concentration in the plasma sample is determined by ELISA (Biosource). The extent of inhibition of the test compounds is expressed as a percentage of the amount of TNFα released in control samples incubated with vehicle. Blood samples with vehicle but no LPS stimulation are also prepared to obtain background levels of TNFα.

II. Rat Whole Blood Assay

TNFα, an NF-κB-driven cytokine, is a key pro-inflammatory molecule that has been demonstrated to be involved in the pathogenesis of a number of inflammatory disorders. This assay monitors the production of TNFα following stimulation of rat blood with LPS. Blood is collected from rats into heparinized vacutainer tubes and subsequently plated into Gordon Tech plates and incubated with test compounds for 15 min at 37° C. with 5% $CO_2$. The blood is stimulated with LPS at a final concentration of 100 ng/μL and incubated at 37° C. for 4 hr. Plasma is obtained by centrifugation (1600×g for 10 min at 4° C.) and the amount of TNFα produced quantified by ELISA (Biosource); the manufacturer's instructions are followed. The extent of inhibition of the test compounds is expressed as a percentage of the amount of TNFα released in control samples incubated with vehicle. Blood samples with DMSO but no LPS stimulation are also prepared to obtain background levels of TNFα.

JAK1 Kinase Activity Inhibition Assay and Determination of $IC_{50}$

For the JAK1 enzyme assay, reactions (50 uL) contained 5×IVGN buffer (50 mM Hepes, pH 7.5, 10 mM MgCl2, 0.01% Brij-35, 1 mM EGTA, 0.1 mg/ml BSA), 2 mM DTT, 2.0 μM peptide substrate, 25 μM MgATP, 400 pM JAK1 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103). Peptide substrate is amino hexanoyl biotin-EQEDEPEGDYFEWLE-NH2 (SEQ. ID.: 3) in DMSO.

$IC_{50}$ was obtained by fitting the observed relationship between compound/inhibitor concentration and HTRF signal with a 4-parameter logistic equation.

Compounds of the instant invention are potent inhibitors of recombinant purified JAK1 kinase activity with an $IC_{50}$ of approximately 0.1 nM-20 μM.

JAK2 Kinase Activity Inhibition Assay and Determination of $IC_{50}$

The kinase activity was measured using a modified version of the homogeneous time-resolved tyrosine kinase assay described in Park et al. *Anal. Biochem.* 269, 94-104 (1999).

The procedure for determining the potency of a compound to inhibit JAK2 kinase comprises the following steps:

prepare 3-fold serial diluted compound/inhibitor solutions in 100% (DMSO) at 20× of the final desired concentrations in a 96 well plate;

prepare a master reaction mix containing 6.67 mM $MgCl_2$, 133.3 mM NaCl, 66.7 mM Tris-HCl (pH 7.4), 0.13 mg/ml BSA, 2.67 mM dithiothreitol, 0.27 recombinant JAK2 and 666.7 nM biotinylated synthetic peptide substrate (biotin-ahx-EQEDEPEGDYFEWLE-$CONH_2$) (SEQ. ID.: 3);

in a black assay plate, add 2.5 μl compound/inhibitor (or DMSO) and 37.5 μl master reaction mix per well;

initiate the kinase reaction by adding 10 μl of 75 μM MgATP per well, allow the reactions to proceed for 80 minutes at room temperate; (the final conditions for the reactions are: 50 nM JAK2 JH1 domain (Upstate), 2.0 μM substrate, 15 μM MgATP, 5 mM $MgCl_2$, 100 mM NaCl, 2 mM DTT, 0.1 mg/ml BSA, 50 mM Tris (pH 7.4) and 5% DMSO);

stop the kinase reaction with 50 μl of Stop/Detection buffer containing 10 mM EDTA, 25 mM HEPES, 0.1% TRITON X-100, 0.126 μg/ml Eu-chelate labeled anti-phosphotyrosine antibody PY20 (cat. #AD0067, PerkinElmer) and 45 μg/ml Streptavidin-allophycocyanin conjugate (cat. #PJ25S, Prozyme); and read HTRF signals on a Victor reader (PerkinElmer) in HTRF mode after 60 minutes.

$IC_{50}$ was obtained by fitting the observed relationship between compound/inhibitor concentration and HTRF signal with a 4-parameter logistic equation.

Compounds of the instant invention are potent inhibitors of recombinant purified JAK2 kinase activity with an $IC_{50}$ of approximately 0.1 nM-20 μM.

JAK3 Kinase Activity Inhibition Assay and Determination of $IC_{50}$

For the JAK1 enzyme assay, reactions (50 uL) contained 5×IVGN buffer (50 mM Hepes, pH 7.5, 10 mM MgCl2, 0.01% Brij-35, 1 mM EGTA, 0.1 mg/ml BSA), 2 mM DTT, 2.0 μM peptide substrate, 25 μM MgATP, 25 μM JAK3 enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103). Peptide substrate is amino hexanoyl biotin-EQEDEPEGDYFEWLE-NH2 (SEQ. ID.: 3) in DMSO. $IC_{50}$ was obtained by fitting the observed relationship between compound/inhibitor concentration and HTRF signal with a 4-parameter logistic equation.

Compounds of the instant invention are potent inhibitors of recombinant purified JAK3 kinase activity with an $IC_{50}$ of approximately 0.1 nM-20 μM.

TYK2 Enzyme Assay

For the TYK2 enzyme assay, reactions (50 uL) contained 5×IVGN buffer (50 mM Hepes, pH 7.5, 10 mM MgCl2, 0.01% Brij-35, 1 mM EGTA, 0.1 mg/ml BSA), 2 mM DTT, 2.0 μM peptide substrate, 15 μM MgATP, 125 pM enzyme and subject compound in 5% DMSO. Reactions were incubated for 60 min at RT and quenched with 50 uL 2× quench detect buffer (10 mM EDTA, 25 mM HEPES, 0.1% TRITON X-100, 4.7 uM-Europium-Py20 and 2.1 mg/mL streptavidin-APC). Incubate 1 hr at RT and read on a Victor V3 set to read Fluorescent Resonance Energy Transfer (Label 1: Lance 615, Label 2: Lance 665, For both: delay=50 us, window time=100 us, cycle=1000 us, flash energy level=103). Peptide substrate is amino hexanoyl biotin-EQEDEPEGDYFEWLE-NH2 (SEQ. ID.: 3) in DMSO. $IC_{50}$ was obtained by fitting the observed relationship between compound/inhibitor concentration and HTRF signal with a 4-parameter logistic equation.

Compounds of the instant invention are potent inhibitors of recombinant purified TYK2 kinase activity with an $IC_{50}$ of approximately 0.1 nM-20 μM.

While a number of embodiments of this invention have been described, it is apparent that the basic examples may be altered to provide other embodiments, encompassed by the present invention. Therefore, it will be appreciated that the scope of this invention is to be defined by the appended claims rather than by the specific embodiments, which have been represented by way of example.

The abbreviations used herein have the following tabulated meanings. Abbreviations not tabulated below have their meanings as commonly used unless specifically stated otherwise.

| | |
|---|---|
| Ac = | Acetyl |
| Bn = | Benzyl |
| CAMP | cyclic adenosine-3',5'-monophosphate |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| $Et_3N$ = | Triethylamine |
| GST | glutathione transferase |
| HMDS | Hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt $6H_2O$ |
| Ms = | methanesulfonyl = mesyl = $SO_2Me$ |
| Ms0 = | methanesulfonate = mesylate |
| NSAID = | non-steroidal anti-inflammatory drug |
| o-Tol = | ortho-tolyl |
| OXONE ® = | $2KHSO_5 \cdot KHSO_4 \cdot K_2SO_4$ |
| PCC = | pyridinium chlorochromate |
| PDC = | pyridinium dichromate |
| PDE | Phosphodiesterase |
| Ph = | Phenyl |
| Phe = | Benzenediyl |
| PMB = | para-methoxybenzyl |
| Pye = | Pyridinediyl |
| r.t. = | room temperature |
| Rac. = | Racemic |
| SAM = | aminosulfonyl or sulfonamide or $SO_2NH_2$ |
| SEM = | 2-(trimethylsilyl)ethoxymethoxy |

| | |
|---|---|
| SPA = | scintillation proximity assay |
| TBAF = | tetra-n-butylammonium fluoride |
| TEA = | triethylamine |
| Th = | 2- or 3-thienyl |
| TFA = | trifluoroacetic acid |
| TFAA = | trifluoroacetic acid anhydride |
| THF = | Tetrahydrofuran |
| Thi = | Thiophenediyl |
| TLC = | thin layer chromatography |
| TMS-CN = | trimethylsilyl cyanide |
| TMSI | trimethylsilyl iodide |
| Tz = | 1H (or 2H)-tetrazol-5-yl |
| CAN | ceric ammonium nitrate |
| $C_3H_5$ = | Allyl |

Alkyl Group Abbreviations

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyclohexyl |

The compounds of the present invention may be conveniently prepared as described below.

Methods of Synthesis

Method A

Benzenethiol 1 is reacted with bromoacetaldehyde diethylacetal in the presence of $K_2CO_3$ in DMF followed by treatment with PPA in toluene to provide thiophene 2 as described by Matsunaga in *Bioorg. Med. Chem.* 2004, 12, 2251. Thiophene 2 is then converted to 2-thiophenecarboxaldehyde 3 as described in the same paper. The 2-thiophenecarboxaldehyde is then treated with malonic acid in pyridine in the presence of piperidine at 110° C. to afford acid 4. The acid 4 is converted to the acyl azide 5 by treatment with isobutyl chloroformate and $NaN_3$. Thermolysis of acid 5 provides the tricyclic 6 which in turn is brominated to give 7. The alcohol 7 is then treated with $POCl_3$ in a microwave reactor to afford the chloro derivative 8. The chloro 8 is then converted to the amino derivative 9 by treatment with p-methoxybenzylamine in a microwave reactor. Derivative 9 is subjected to the zinc cyanide tetrakis(triphenylphosphine)palladium conditions in a microwave reactor to provide the cyano derivative 10. Deprotection and hydrolysis of the cyano 10 was achieved in a single operation by treating 10 with $PPA/CH_3SO_3H$ to give the desired product 11. Alternatively, compound 10 can be treated with $KOSiMe_3$ in a microwave reactor followed by TFA to give 11.

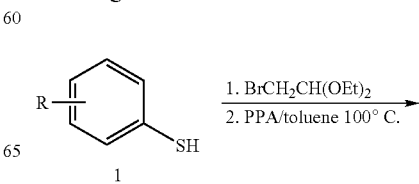

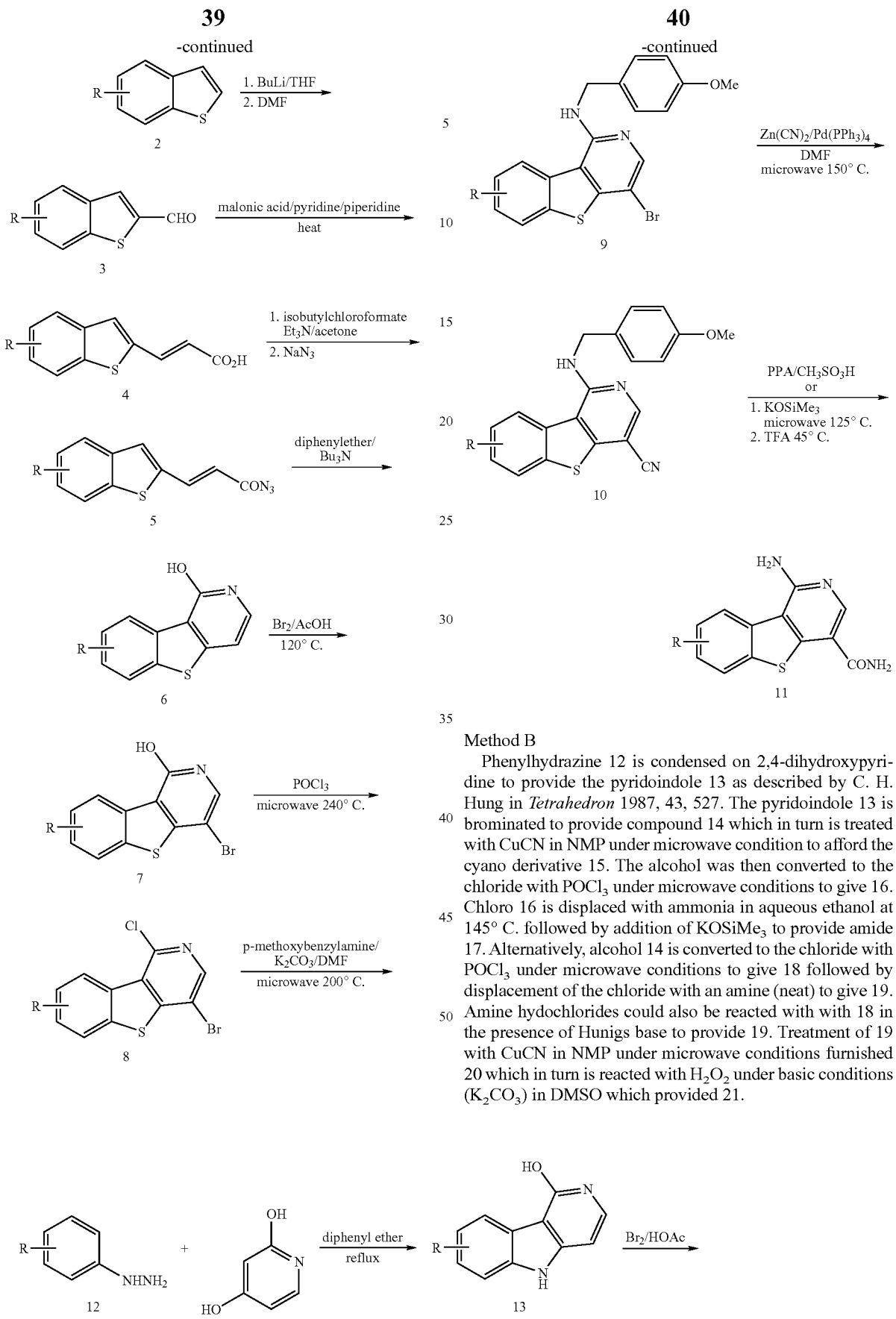

Method B

Phenylhydrazine 12 is condensed on 2,4-dihydroxypyridine to provide the pyridoindole 13 as described by C. H. Hung in *Tetrahedron* 1987, 43, 527. The pyridoindole 13 is brominated to provide compound 14 which in turn is treated with CuCN in NMP under microwave condition to afford the cyano derivative 15. The alcohol was then converted to the chloride with $POCl_3$ under microwave conditions to give 16. Chloro 16 is displaced with ammonia in aqueous ethanol at 145° C. followed by addition of $KOSiMe_3$ to provide amide 17. Alternatively, alcohol 14 is converted to the chloride with $POCl_3$ under microwave conditions to give 18 followed by displacement of the chloride with an amine (neat) to give 19. Amine hydochlorides could also be reacted with with 18 in the presence of Hunigs base to provide 19. Treatment of 19 with CuCN in NMP under microwave conditions furnished 20 which in turn is reacted with $H_2O_2$ under basic conditions ($K_2CO_3$) in DMSO which provided 21.

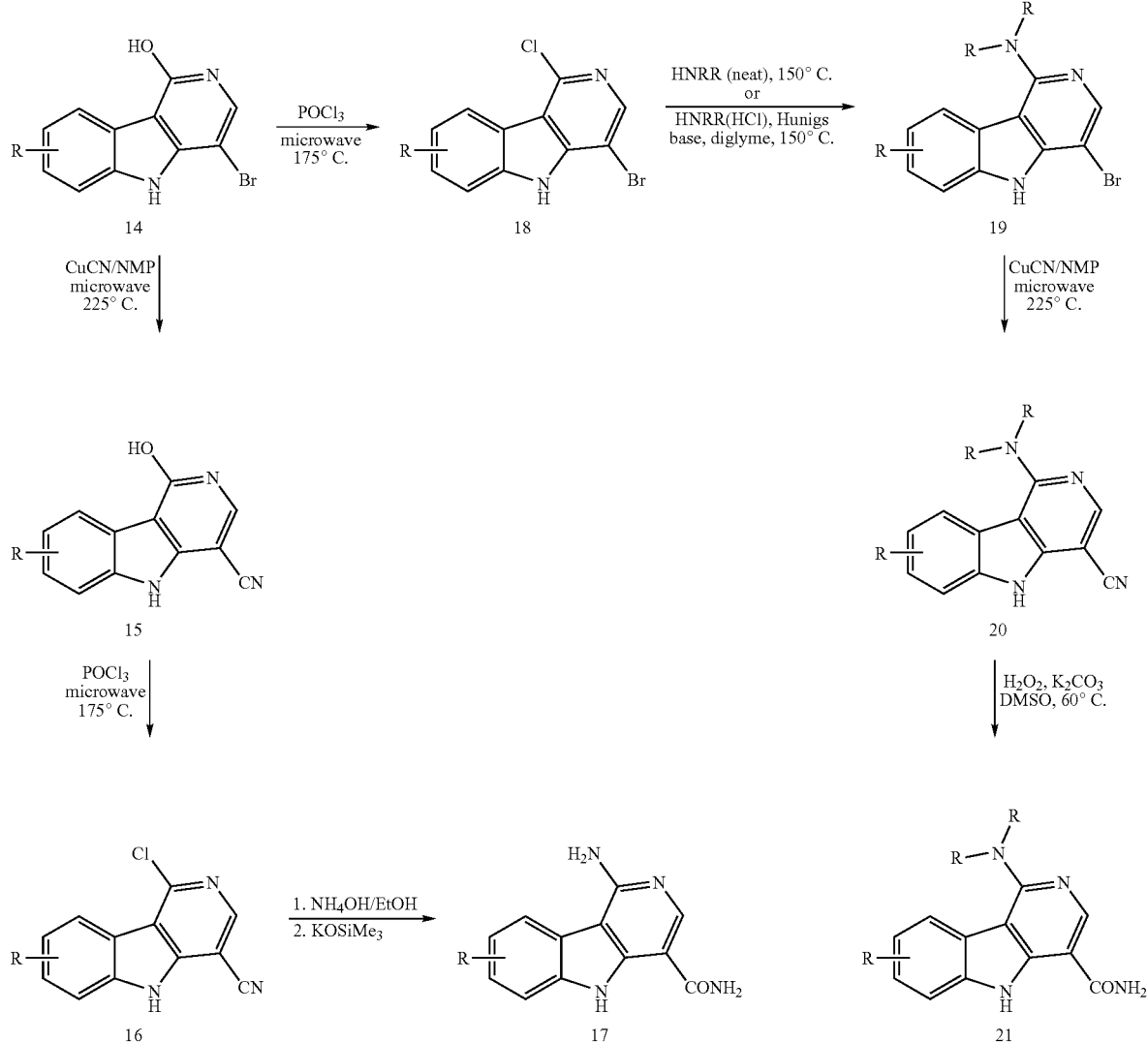

Method C

The alcohol 7, described in Method A, is treated with CuCN in NMP under reflux to afford cyanoderivative 22. The compound 22 is brominated with Br$_2$ in AcOH under reflux for 1 h to give 23. The alcohol 23 is then treated with POCl$_3$ under reflux for 8 h to afford the chloro derivative 24. The chloro 24 is then converted to the amino derivative 25 by treatment with p-methoxybenzylamine in DMF at 110° C. for 1 h. Deprotection and hydrolysis of the cyano 25 was achieved in a single operation by treating 25 with conc. H$_2$SO$_4$ at room temperature to give 26.

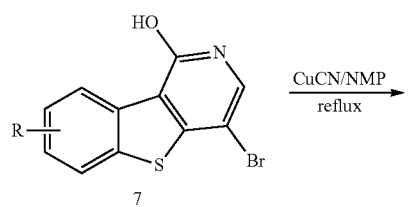

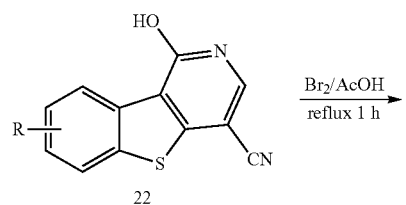

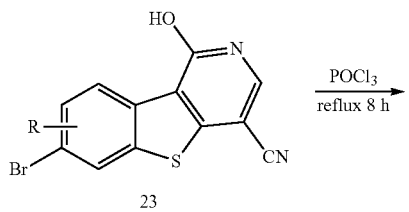

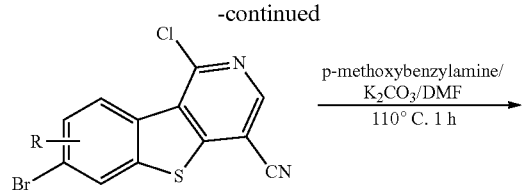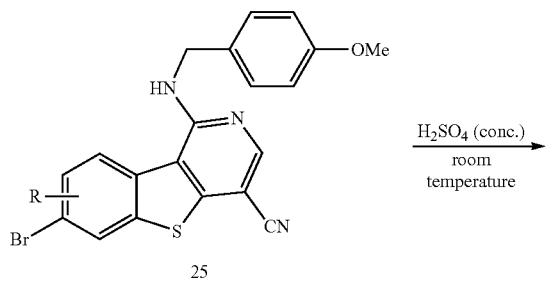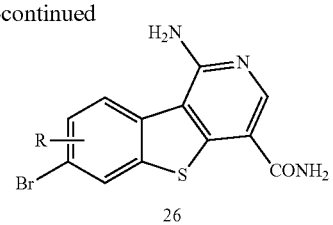

Method D

Benzotriazole 27 is heated neat with methyl 4,6-dichloronicotinate 28 to give benzotriazole derivative 29, which after heating with PPA provides the pyridoindole 30, as described by A. Molina in the *J. Org. Chem.* 1996, 61, 5587. The pyridoindole 30 is treated with LiNH$_2$ to afford the amide 31. The amide 31 can be directly treated with NH$_4$OH under microwave conditions to give 32. Also, amide 31 can be first brominated to provide 33 and finally converted to the amide 34.

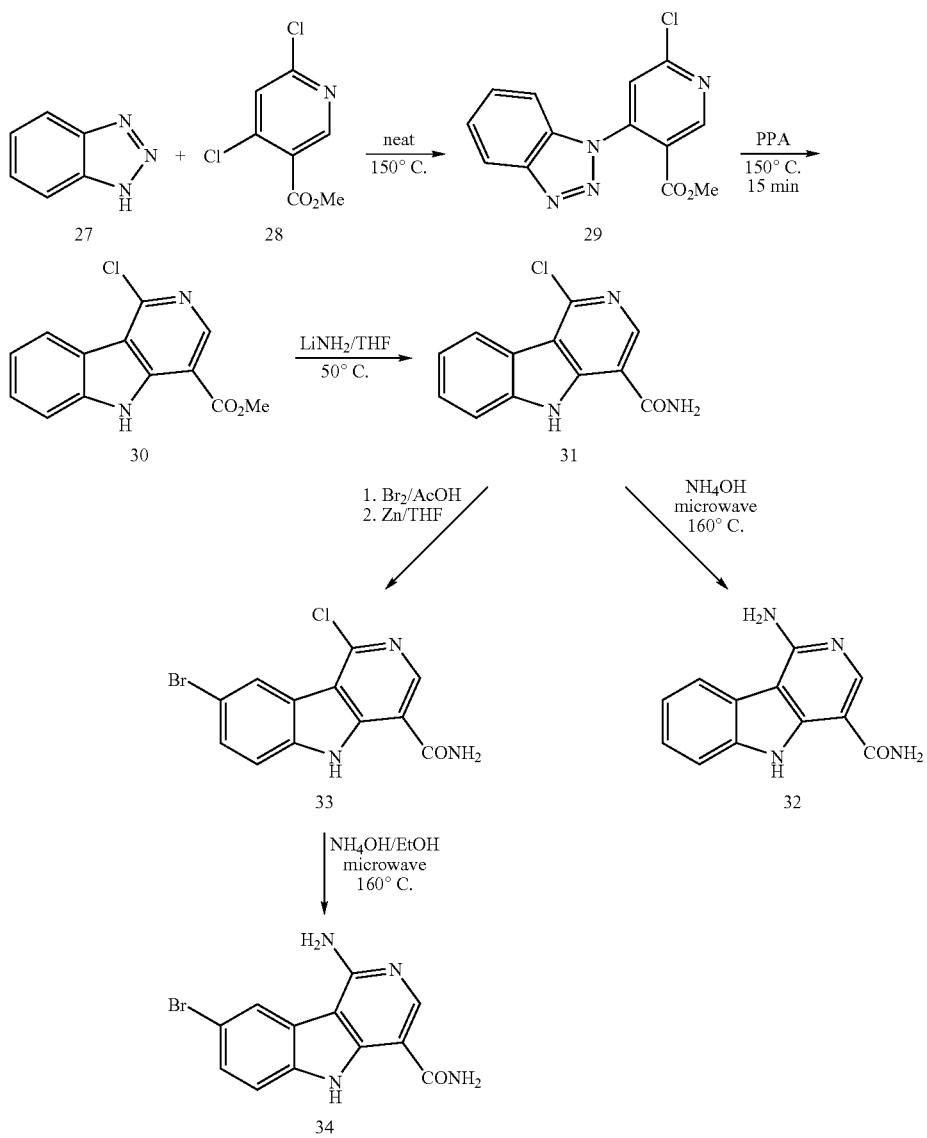

Method E

A useful alternative to access intermediate 3 is depicted in method E. An aldehyde of general structure 35 substituted in the ortho position with a leaving group such as a fluorine substituent can be reacted with a nucleophile like ethyl-2-mercaptoacetate in the presence of a strong base such as DBU (1,8-diazabicyclo[5.4.0]undec-7-ene) to give the benzothiophene ester 36. The ester 36 is hydrolyzed with LiOH to yield an acid, and the acid is coupled with methoxymethylamine to give the Weinreb amide 37. The amide is then reduced to the aldehyde of general structure 3.

Method F

The oxygen analogs in the benzofuran series can be prepared in a similar manner as described below. Benzofuran-carboxaldehyde 38 is homologated to the corresponding acrylic acid 39. The acid is activated to form the azide 40 that is cyclized at high temperature to the pyridone 41. The pyridone is brominated to give 42, followed by treatment with POCl₃ to give 43. The chlorine is selectively displaced with p-methoxybenzylamine to give protected aniline 44. Cyanation of 44 gives intermediate 45 that is hydrolyzed in either a one-step process or a two-step process to give the final active product of general structure 46.

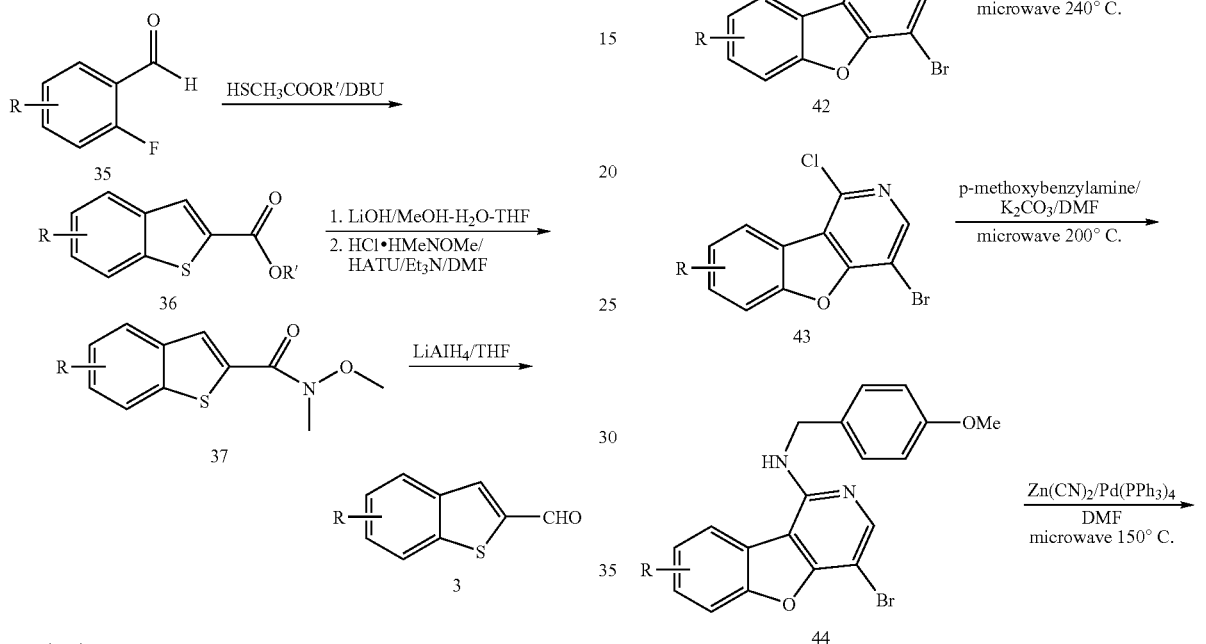

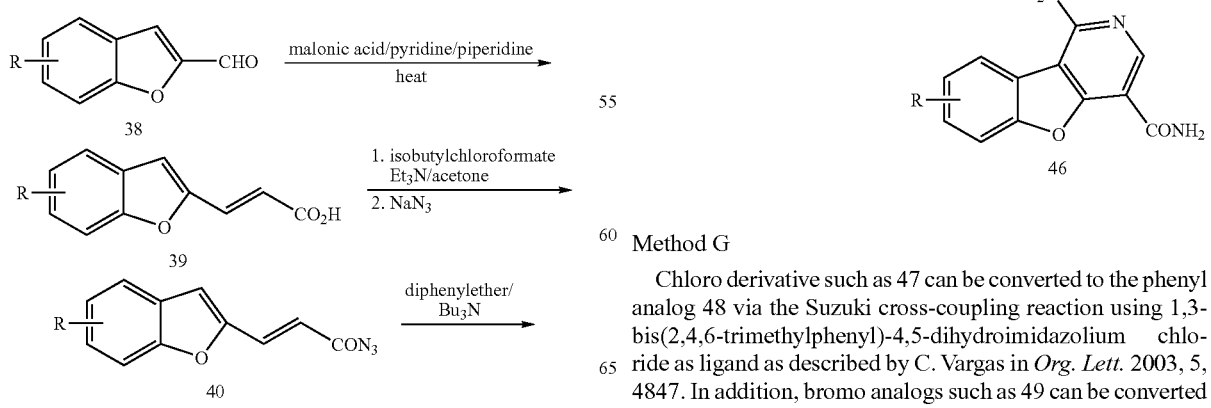

Method G

Chloro derivative such as 47 can be converted to the phenyl analog 48 via the Suzuki cross-coupling reaction using 1,3-bis(2,4,6-trimethylphenyl)-4,5-dihydroimidazolium chloride as ligand as described by C. Vargas in *Org. Lett.* 2003, 5, 4847. In addition, bromo analogs such as 49 can be converted to phenyl analogs 50 using palladium as catalyst.

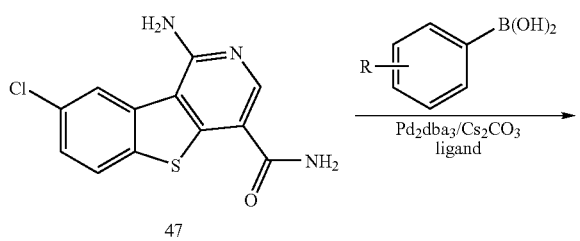
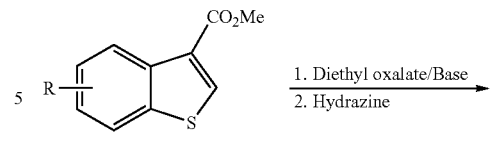
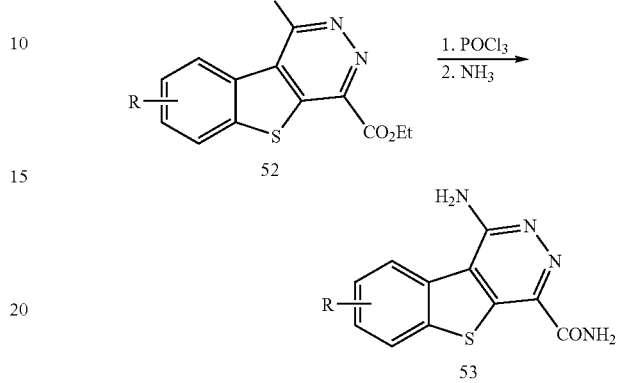
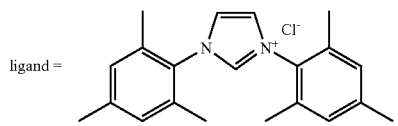
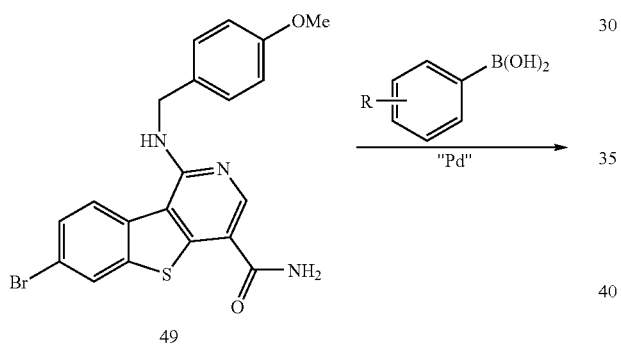

Method H

Methyl 1-benzothiophene-3-carboxylate methyl ester 51 is treated with diethyl oxalate and a base such as lithium diisopropylamide followed by treatment with hydrazine to provide 52. The compound 52 is then converted to the chloro analog with POCl₃ followed by treatment with ammonia to give 53.

The invention will now be illustrated in the following non-limiting Examples in which, unless otherwise stated:
1. All the end products of the formula I were analyzed by NMR, TLC.
2. Intermediates were analyzed by NMR and/or TLC.
3. Most compounds were purified by flash chromatography on silica gel, recrystallization and/or swish (suspension in a solvent followed by filtration of the solid).
4. The course of reactions was followed by thin layer chromatography (TLC) and reaction times are given for illustration only.

EXAMPLE 1

1-Amino-8-chloro[1]benzothieno[3,2-c]pyridine-4-carboxamide

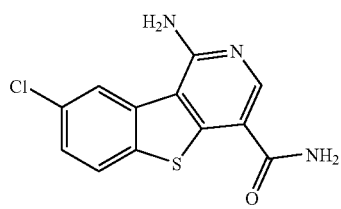 [SMILES: NC(=O)c1cnc(N)c2c1sc1ccc(Cl)cc12]

Step 1. (2E)-3-(5-Chloro-1-benzothien-2yl)acrylic acid

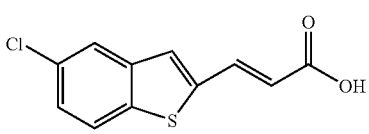 [SMILES: O=C(O)/C=C/c1cc2cc(Cl)ccc2s1]

A mixture containing 5-chlorobenzo[b]thiophene-2-carboxaldehyde (Matsunaga *Bioorg. Med. Chem.* 2004, 12, 2251), malonic acid (1.4 equiv), pyridine (2.5 equiv) and piperidine (0.1 equiv) was heated at 110° C. for a period of 4 h. The reaction mixture was cooled, poured into H₂O and filtered to provide the title compound.

Step 2. (2E)-3-(5-Chloro-1-benzothien-2-yl)acryloylazide

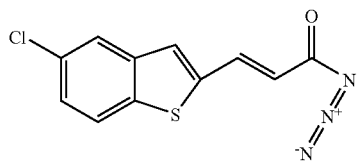

To a suspension of (2E)-3-(5-chloro-1-benzothien-2-yl) acrylic acid in acetone (0.2 M) at 0° C. were added Et₃N (1.3 equiv) followed by isobutyl chloroformate (1.3 equiv). After stirring for 1 h, H₂O solution (2 M) of NaN₃ (1.3 equiv) was then added. The resulting mixture was stirred for a period of 0.5 h at 0° C. and 30 min at room temperature. H₂O was then added followed by filtration and wash with H₂O to provide the title compound.

Step 3. 8-Chloro[1]benzothieno[3,2-c]pyridine-1-ol

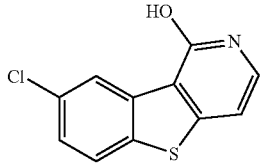 [SMILES: Oc1nccc2sc3ccc(Cl)cc3c12]

A suspension of (2E)-3-(5-chloro-1-benzothien-2-yl)acryloylazide in diphenyl ether and Bu₃N (4/1) (0.4 M) was heated at reflux for a period of 1 h. The mixture was cooled to room temperature followed by addition of hexanes. The solid was filtered to provide the title compound as a yellow solid.

Step 4.
4-Bromo-8-chloro[1]benzothieno[3,2-c]pyridine-1-ol

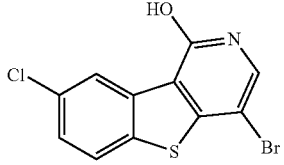 [SMILES: Oc1ncc(Br)c2sc3ccc(Cl)cc3c12]

To 8-chloro[1]benzothieno[3,2-c]pyridine-1-ol in AcOH (0.3 M) was added Br₂ (1.1 equiv). The resulting mixture was heated at 120° C. for 1 h, cooled to room temperature, poured into H₂O and filtered. The solid was suspended in acetone, sonicated and filtered to provide the title compound.

Step 5.
4-Bromo-1,8-dichloro[1]benzothieno[3,2-c]pyridine

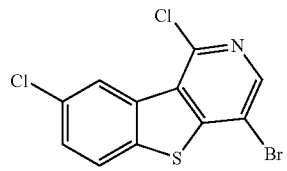 [SMILES: Clc1ccc2sc3c(Br)cnc(Cl)c3c2c1]

A suspension of 4-bromo-8-chloro[1]benzothieno[3,2-c]pyridine-1-ol in POCl₃ (1 M) was placed in a microwave reactor at 240° C. (normal absorption) for 10 min. The reaction mixture was carefully extracted with EtOAc/NaHCO₃, dried over Na₂SO₄, filtered and evaporated to provide the title compound.

Step 6. 4-Bromo-8-chloro-N-(4-methoxybenzyl)[1]benzothieno[3,2-c]pyridine-1-amine

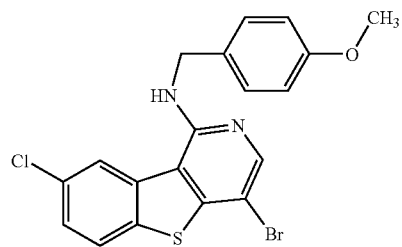 [SMILES: COc1ccc(CNc2ncc(Br)c3sc4ccc(Cl)cc4c23)cc1]

A mixture containing 4-bromo-1,8-dichloro[1]benzothieno[3,2-c]pyridine-4-methoxybenzylamine (5 equiv), K₂CO₃ (4.0 equiv) in DMF (0.2 M) was placed in a microwave reactor at 200° C. for 3.3 min. The reaction was diluted with EtOAc and ether and washed with H₂O. The organic solvents were separated and evaporated. The desired product was purified by flash chromatography (10% EtOAc in hexanes).

Step 7. 8-Chloro-1-[(4-methoxybenzyl)amino][1]benzothieno[3,2-c]pyridine-4-carbonitrile

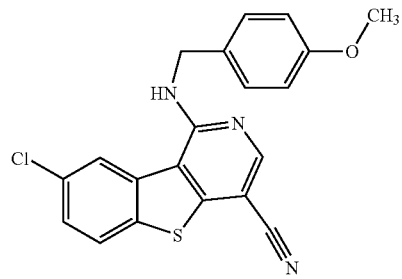 [SMILES: COc1ccc(CNc2ncc(C#N)c3sc4ccc(Cl)cc4c23)cc1]

A mixture containing 4-bromo-8-chloro-N-(4-methoxybenzyl)[1]benzothieno[3,2-c]pyridine-1-amine, Zn(CN)₂ (1.2 equiv) and Pd(Ph₃P)₄ (0.1 equiv) in DMF (0.1 M) was placed in microwave reactor at 150° C. for 10 min. The reaction was poured into H₂O, filtered and washed with MeOH.

Step 8. 1-Amino-8-chloro[1]benzothieno[3,2-c]pyridine-4-carboxamide

A suspension of 8-chloro-1-[(4-methoxybenzyl)amino][1]benzothieno[3,2-c]pyridine-4-carbonitrile in a 1:1 (mass/mass) mixture of PPA/CH₃SO₃H (0.8 M) was heated at 125° C. for 2 h. The reaction mixture was cooled to room temperature and partitioned between EtOAc and H₂O. The H₂O was neutralized with NaHCO₃ and NaOH followed by separation of the organic phase. The aqueous phase was extracted again with EtOAc and THF. The solvents were evaporated and the mixture purified by flash chromatography (EtOAc to 10% MeOH in EtOAc) to afford the title compound.

$^1$H NMR (DMSO-d$_6$) δ 8.75 (1H, s), 8.55 (1H, s), 8.10 (2H, d and br s), 7.55 (1H, d), 7.40 (1H, br s), 7.20 (2H, br s).

EXAMPLE 2

1-Amino-8-phenyl[1]benzothieno[3,2-c]pyridine-4-carboxamide

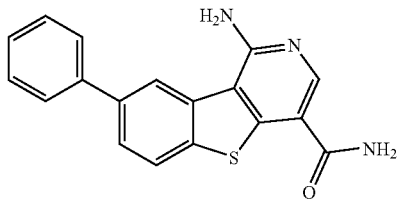 [SMILES: NC(=O)c1cnc(N)c2c1sc1ccc(-c3ccccc3)cc12]

A mixture containing 1-amino-8-chloro[1]benzothieno[3,2-c]pyridine-4-carboxamide (Example 1), phenylboronic acid (1.9 equiv), 1,3-bis(2,4,6-trimethylphenyl)-4,5-dihydroimidazolium chloride (0.2 equiv), cesium carbonate (2.4 equiv), tris(dibenzylideneacetone)dipalladium (0.1 equiv) in dioxane (0.3 M) was placed in a microwave reactor at 120° C. for 23 min. The resulting mixture was extracted with EtOAc-DMSO and H₂O. The organic phase was separated and purified by flash chromatography (EtOAc to 10% MeOH in EtOAc) to provide the title compound.

$^1$H NMR (DMSO-d$_6$) δ 8.75 (1H, s), 8.60 (1H, s), 8.15 (1H, d), 8.10 (1H, br s), 7.90 (2H, d), 7.80 (1H, d), 7.50 (2H, t), 7.35 (2H, t and br s), 7.20 (2H, br s).

EXAMPLE 3

1-Amino-6-chloro[1]benzothieno[3,2-c]pyridine-4-carboxamide

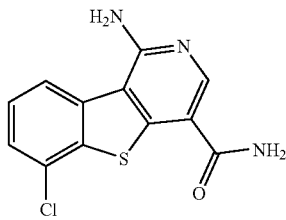 [SMILES: NC(=O)c1cnc(N)c2c1sc1c(Cl)cccc12]

Step 1. (2E)-3-(7-Chloro-1-benzothien-2yl)acrylic acid

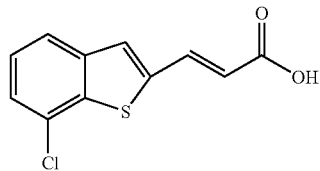 [SMILES: O=C(O)/C=C/c1cc2cccc(Cl)c2s1]

The title compound was prepared as described in Example 1, Step 1 using 7-chlorobenzo[b]thiophene-2-carboxaldehyde as starting material which in turn was prepared from 2-chlorothiophenol using the protocol for the 5-isomer in Matsunaga *Bioorg. Med. Chem.* 2004, 12, 2251.

Step 2. (2E)-3-(7-Chloro-1-benzothien-2-yl)acryloylazide

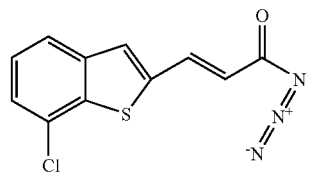

The title compound was prepared from (2E)-3-(7-chloro-1-benzothien-2-yl)acrylic acid as described in Example 1, Step 2.

Step 3. 6-Chloro[1]benzothieno[3,2-c]pyridine-1-ol

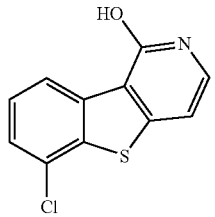 [SMILES: Oc1nccc2sc3c(Cl)cccc3c12]

The title compound was prepared from (2E)-3-(7-chloro-1-benzothien-2-yl)acryloylazide as described in Example 1, Step 3.

Step 4. 4-Bromo-6-chloro[1]benzothieno[3,2-c]pyridine-1-ol

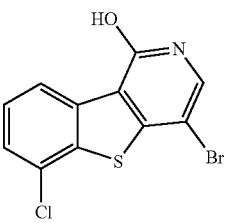 [SMILES: Clc1cccc2c1sc1c(Br)cnc(Cl)c12]

The title compound was prepared from 6-chloro[1]benzothieno[3,2-c]pyridine-1-ol as described in Example 1, Step 4.

Step 5.
4-Bromo-1,6-dichloro[1]benzothieno[3,2-c]pyridine

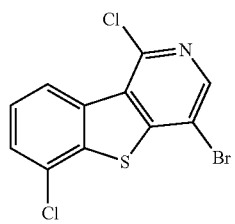

The title compound was prepared from 4-bromo-6-chloro[1]benzothieno[3,2-c]pyridine-1-ol as described in Example 1, Step 5.

Step 6. 4-Bromo-6-chloro-N-(4-methoxybenzyl)[1]benzothieno[3,2-c]pyridine-1-amine

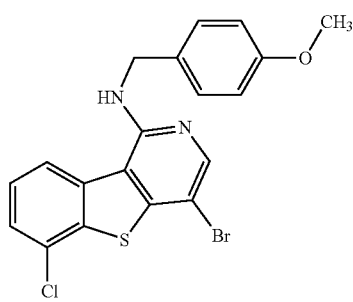 [SMILES: COc1ccc(CNc2ncc(Br)c3sc4c(Cl)cccc4c23)cc1]

The title compound was prepared from 4-bromo-1,6-dichloro[1]benzothieno[3,2-c]pyridine as described in Example 1, Step 6.

Step 7. 6-Chloro-1-[(4-methoxybenzyl)amino][1]benzothieno[3,2-c]pyridine-4-carbonitrile

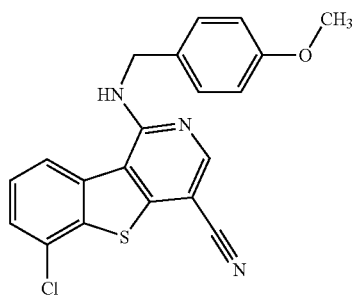 [SMILES: COc1ccc(CNc2ncc(C#N)c3sc4c(Cl)cccc4c23)cc1]

The title compound was prepared from 4-bromo-6-chloro-N-(4-methoxybenzyl)[1]benzothieno[3,2-c]pyridine-1-amine as described in Example 1, Step 7.

Step 8. 1-Amino-6-chloro[1]benzothieno[3,2-]pyridine-4-carboxamide

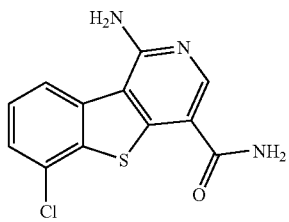 [SMILES: NC(=O)c1cnc(N)c2c1sc1c(Cl)cccc12]

To 6-chloro-1-[(4-methoxybenzyl)amino][1]benzothieno[3,2-c]pyridine-4-carbonitrile in THF (0.1 M) was added KOSiMe$_3$ (5 equiv). After a period of 1 h at 125° C. in the microwave reactor, the reaction mixture was dissolved in DMSO and partitioned between EtOAc and H$_2$O. The organic phase was separated, dried over Na$_2$SO$_4$ and evaporated. The crude product was dissolved in excess of TFA and heated at 45° C. After a period of 1 h, the solvent was evaporated and the crude product was partitioned between EtOAc and H$_2$O. After addition of THF and NaHCO$_3$, the organic phase was separated and evaporated to give a solid. The solid was suspended in EtOAc and filtered to provide the title compound.

$^1$H NMR (DMSO-d$_6$) δ 8.80 (1H, s), 8.45 (1H, d), 8.10 (1H, br s), 7.55 (2H, m), 7.45 (1H, br s), 7.20 (2H, br s).

EXAMPLE 4

1-Amino-6-phenyl[1]benzothieno[3,2-c]pyridine-4-carboxamide

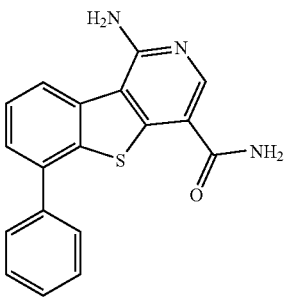 [SMILES: NC(=O)c1cnc(N)c2c1sc1c(-c3ccccc3)cccc12]

The title compound was prepared as described in Example 2 using 1-amino-6-chloro[1]benzothieno[3,2-c]pyridine-4-carboxamide of Example 3, Step 8 as starting material.

$^1$H NMR (DMSO-d$_6$) δ 8.70 (1H, s), 8.50 (1H, d), 8.05 (1H, br s), 7.75 (2H, m), 7.65 (3H, m), 7.45 (2H, m), 7.35 (1H, br s), 7.20 (2H, br s).

EXAMPLE 5

1-Amino-7-(trifluoromethyl)-5H-pyrido[4,3-b]indole-4-carboxamide

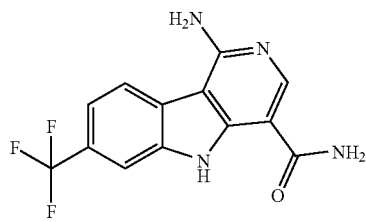 [SMILES: NC(=O)c1cnc(N)c2c1[nH]c1cc(C(F)(F)F)ccc12]

Step 1.
7-(Trifluoromethyl)-5H-pyrido[4,3-b]indol-1-ol

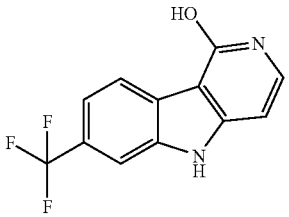 [SMILES: Oc1nccc2[nH]c3cc(C(F)(F)F)ccc3c12]

A mixture 2,4-dihydroxypyridine and 3-trifluoromethylphenylhydrazine (2.6 equiv) in diphenyl ether was heated at reflux with a Dean Stark apparatus for 2 h as described by C. H. Nguyen in *Tetrahedron* 1987, 43, 527. The reaction was cooled to room temperature followed by the addition of toluene. The solid was collected and washed with toluene. The solid was then dissolved in EtOAc and purified by flash chromatography (EtOAc to 5% MeOH in EtOAc) to provide the title compound.

Step 2. 4-Bromo-7-(trifluoromethyl)-5H-pyrido[4,3-b]indol-1-ol

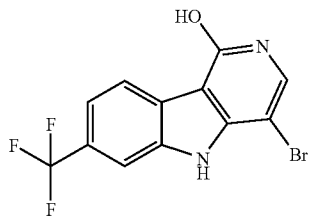 [SMILES: Oc1ncc(Br)c2[nH]c3cc(C(F)(F)F)ccc3c12]

To a suspension of 7-(trifluoromethyl)-5H-pyrido[4,3-b]indol-1-ol in AcOH (0.3 M) in a cold water bath was added a solution (0.3 M) of $Br_2$ (1 equiv) in dichloromethane to provide a homogeneous mixture. After standing at room temperature a precipitate formed, and Zn powder (excess) was added at 0° C. After a period of 10 min, the reaction mixture was poured over EtOAc and saturated $NaHCO_3$. The organic phase was separated, dried over $Na_2SO_4$ and evaporated. The resulting solid was suspended in ether and hexanes, and was then collected by filtration.

Step 3. 1-Hydroxy-7-(trifluoromethyl)-5H-pyrido[4,3-b]indole-4-carbonitrile

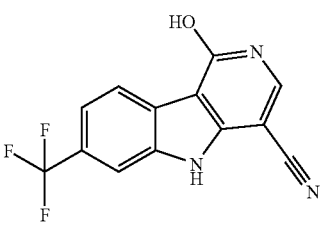 [SMILES: N#Cc1cnc(O)c2c1[nH]c1cc(C(F)(F)F)ccc12]

A mixture of 4-bromo-7-(trifluoromethyl)-5H-pyrido[4,3-b]indol-1-ol, CuCN (1.4 equiv) in NMP (0.2 M) was heated in the microwave reactor at 225° C. for 40 min. The reaction mixture was then poured into EtOAc/hexanes (10/1) which was passed through a plug of silica gel and eluted with EtOAc. The EtOAc was evaporated and the resulting mixture was partitioned between EtOAc and brine. The organic phase was separated, dried over $Na_2SO_4$ and evaporated. The residue was suspended in EtOAc and hexanes, and was then filtered to provide the title compound.

Step 4. 1-Chloro-7-(trifluoromethyl)-5H-pyrido[4,3-b]indole-4-carbonitrile

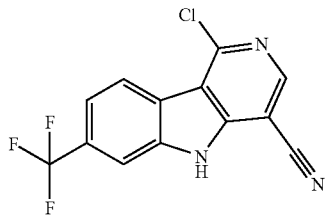 [SMILES: N#Cc1cnc(Cl)c2c1[nH]c1cc(C(F)(F)F)ccc12]

A mixture of 1-hydroxy-7-(trifluoromethyl)-5H-pyrido[4,3-b]indole-4-carbonitrile in an excess of $POCl_3$ was heated in a microwave apparatus at 175° C. for a period of 13 min. The reaction mixture was poured slowly into cold EtOAc and saturated $NaHCO_3$. The organic phase was separated, dried over $Na_2SO_4$, filtered and evaporated to give the title compound.

Step 5. 1-Amino-7-(trifluoromethyl)-5H-pyrido[4,3-b]indole-4-carboxamide

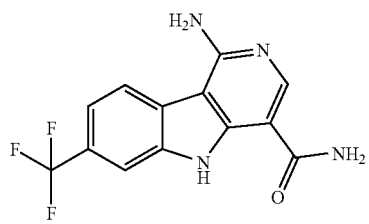 [SMILES: NC(=O)c1cnc(N)c2c1[nH]c1cc(C(F)(F)F)ccc12]

A mixture of 1-chloro-7-(trifluoromethyl)-5H-pyrido[4,3-b]indole-4-carbonitrile in a 3:2 (v/v) mixture of EtOH and conc. $NH_4OH$ (0.06 M) was heated at 150° C. for 2 h in a stainless steel pressure vessel. After cooling at room temperature, an excess of $KOSiMe_3$ was added and the mixture was heated at 150° C. for 18 h. The reaction mixture was extracted with EtOAc and $H_2O$. After evaporation of the organic solvent the residue was purified by flash chromatography (10% MeOH in EtOAc) to provide the title compound as a white solid.

$^1$H NMR (DMSO-$d_6$) δ 12.20 (1H, s), 8.85 (1H, s), 8.80 (1H, d), 8.35 (1H, s), 8.20 (1H, br s), 7.75 (1H, d), 7.45 (1H, br s), 7.25 (2H, br s).

EXAMPLE 6

1-Amino-8-fluoro-5H-pyrido[4,3-b]indole-4-carboxamide

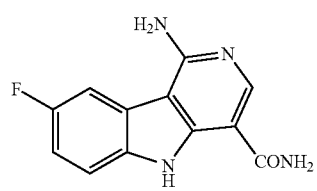 [SMILES: NC(=O)c1cnc(N)c2c1[nH]c1ccc(F)cc12]

Step 1. 1-Chloro-8-fluoro-5H-pyrido[4,3-b]indole-4-carbonitrile

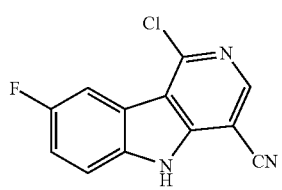 [SMILES: N#Cc1cnc(Cl)c2c1[nH]c1ccc(F)cc12]

The title compound was prepared as described in Example 5, Steps 1-4 using 4-fluorophenylhydrazine as starting material.

Step 2. 1-Amino-8-fluoro-5H-pyrido[4,3-b]indole-4-carboxamide

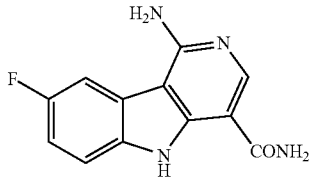 [SMILES: NC(=O)c1cnc(N)c2c1[nH]c1ccc(F)cc12]

A mixture of 1-chloro-8-fluoro-5H-pyrido[4,3-b]indole-4-carbonitrile in a 1:1 (v/v) mixture of EtOH and conc. NH₄OH (0.13 M) was heated in a microwave reactor at 150° C. for 1 h in a sealed tube. After cooling to room temperature, the suspension was diluted with H₂O and filtered. The crude material was placed in a flask cooled to 0° C. before conc. H2SO₄ (excess) was added dropwise under vigorous stirring. The final mixture was warmed to room temperature and, after 4 h, poured carefully into a diluted aqueous solution of NH₄OH cooled to 0° C. The precipitate was collected by filtration and was purified by flash chromatography (20-50% ethanol in CH₂Cl₂) to provide the title compound as an off-white solid.

¹H NMR (DMSO-d₆) δ 11.55 (1H, s), 8.50 (1H, s), 8.20 (1H, dd), 7.85 (1H, br s), 7.70 (1H, dd), 7.20 (1H, m), 7.10 (1H, br s), 6.90 (2H, br s).

EXAMPLE 7

8-Fluoro-1-(methylamino)-5H-pyrido[4,3-b]indole-4-carboxamide

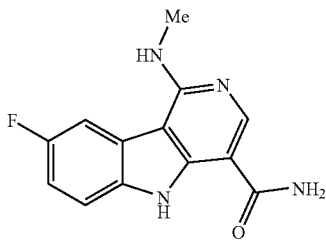 [SMILES: CNc1ncc(C(N)=O)c2[nH]c3ccc(F)cc3c12]

Step 1.
8-Fluoro-2,5-dihydro-1H-pyrido[4,3-b]indol-1-one

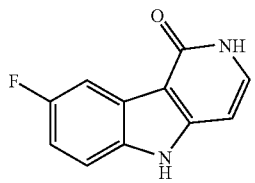 [SMILES: O=c1[nH]ccc2[nH]c3ccc(F)cc3c12]

8-fluoro-2,5-dihydro-1H-pyrido[4,3-b]indol-1-one was prepared according to the procedure described in example 5 step 1.

Step 2. 4-Bromo-8-fluoro-2,5-dihydro-1H-pyrido[4,3-b]indol-1-one

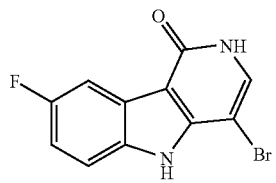 [SMILES: O=c1[nH]cc(Br)c2[nH]c3ccc(F)cc3c12]

8-Fluoro-2,5-dihydro-1H-pyrido[4,3-b]indol-1-one (10 g, 49 mmol) was dissolved in 400 mL DMF and covered with aluminum foil. NBS was added in a single portion and the solution was stirred for 1 hr at which time the reaction mixture was diluted with EtOAc, washed with water, brine, dried over MgSO4, filtered, concentrated. The crude residue purified on silica gel and eluted with EtOAc/hexanes (0 to 75% gradient elution).

Step 3.
4-Bromo-1-chloro-8-fluoro-5H-pyrido[4,3-b]indole

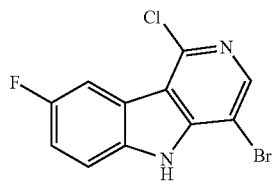 [SMILES: Fc1ccc2[nH]c3c(Br)cnc(Cl)c3c2c1]

4-Bromo-8-fluoro-2,5-dihydro-1H-pyrido[4,3-b]indol-1-one (1 gram) was suspended in 10 mL POCl₃ and heated to 175° C. for 15 minutes in a microwave. The crude reaction mixture was poured over ice, neutralized with 12 M NaOH, extracted with EtOAc, washed with brine, dried over MgSO4, filtered, concentrated to dryness. The title compound was used without further purification.

Step 4. 4-Bromo-8-fluoro-N-methyl-5H-pyrido[4,3-b]indol-1-amine

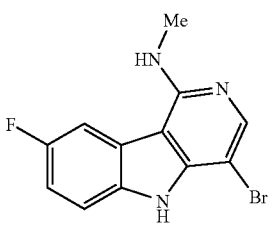 [SMILES: CNc1ncc(Br)c2[nH]c3ccc(F)cc3c12]

4-Bromo-1-chloro-8-fluoro-5H-pyrido[4,3-b]indole (150 mg, 0.501 mmol) was dissolved in methylamine in methanol (3 mL, 6.00 mmol) and heated to 140° C. in the microwave for six hours. The reaction mixture was concentrated in vacuo and purified on silica gel (0-20% ethyl acetate/hexanes gradient elution).

Step 5. 8-Fluoro-1-(methylamino)-5H-pyrido[4,3-b]indole-4-carbonitrile

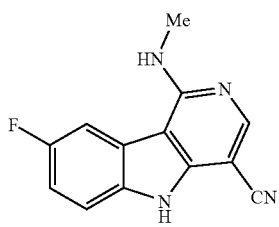 [SMILES: CNc1ncc(C#N)c2[nH]c3ccc(F)cc3c12]

4-Bromo-8-fluoro-N-methyl-5H-pyrido[4,3-b]indol-1-amine (150 mg, 0.501 mmol) was combined with copper(I) cyanide (114 mg, 1.275 mmol) and dissolved in NMP (2.55 mL). The reaction was heated to 225° C. in a microwave for one hr. The solution was cooled to ambient temperature, diluted with ethyl acetate, washed with water, dried over magnesium sulfate, filtered and concentrated. The crude residue was purified on silica gel (EtOAc/hexanes).

Step 6. 8-Fluoro-1-(methylamino)-5H-pyrido[4,3-b]indole-4-carboxamide

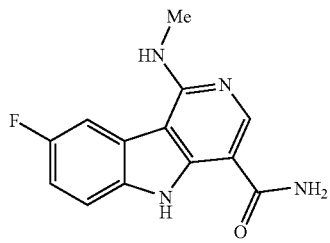 [SMILES: CNc1ncc(C(N)=O)c2[nH]c3ccc(F)cc3c12]

8-Fluoro-1-(methylamino)-5H-pyrido[4,3-b]indole-4-carbonitrile (36 mg, 0.150 mmol) was combined with $K_2CO_3$ (55.9 mg, 0.405 mmol) and dissolved in DMSO (3 ml) followed by the addition of hydrogen peroxide (0.066 ml, 0.749 mmol). The solution was heated at 50° C. for three hr. The solution was cooled to ambient temperature directly purified by HPLC (eluted with MeCN/$H_2O$ with 1% TFA).

EXAMPLE 8

1-(Butylamino)-8-fluoro-5H-pyrido[4,3-b]indole-4-carboxamide

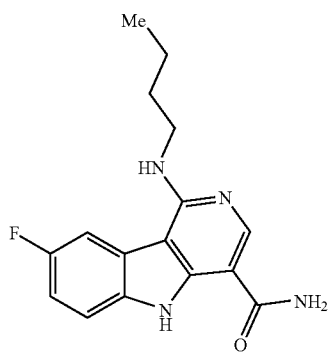 [SMILES: CCCCNc1ncc(C(N)=O)c2[nH]c3ccc(F)cc3c12]

Step 1. 4-Bromo-N-butyl-8-fluoro-5H-pyrido[4,3-b]indol-1-amine

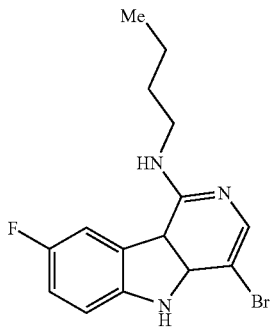 [SMILES: CCCCNC1=NC=C(Br)C2Nc3ccc(F)cc3C12]

4-Bromo-1-chloro-8-fluoro-5H-pyrido[4,3-b]indole (150 mg, 0.501 mmol) was suspended in n-butylamine (36.1 mg, 0.501 mmol) and heated to 100° C. for 48 hr. After cooling to ambient temperature, the crude reaction mixture was loaded directly onto silica gel for purification (EtOAc/hexanes). The intermediate was processed according to the general procedures outlined in Example 1 Steps E and F to provide the title compound.

Step 2. 1-(Butylamino)-8-fluoro-5H-pyrido[4,3-b]indole-4-carboxamide

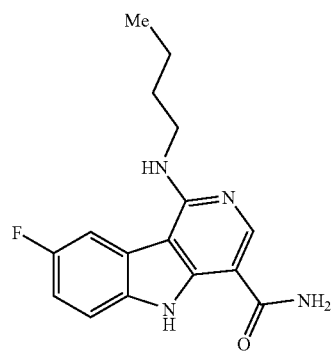 [SMILES: CCCCNc1ncc(C(N)=O)c2[nH]c3ccc(F)cc3c12]

The title compound was completed according the procedures described in Example 7 steps 5 and 6.

EXAMPLE 9

8-Fluoro-1-(1'H,3H-spiro[2-benzofuran-1,4'-piperidin]-1'-yl)-5H-pyrido[4,3-b]indole-4-carboxamide

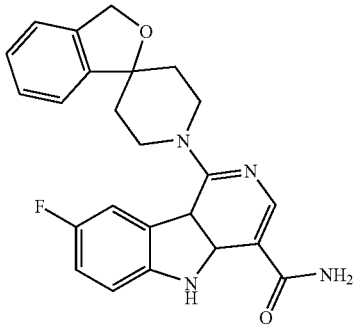 [SMILES: NC(=O)C1=CN=C(N2CCC3(CC2)OCc2ccccc23)C2c3cc(F)ccc3NC12]

Step 1. 1'-(4-Bromo-8-fluoro-5H-pyrido[4,3-b]indol-1-yl)-3H-spiro[2-benzofuran-1,4'-piperidine]

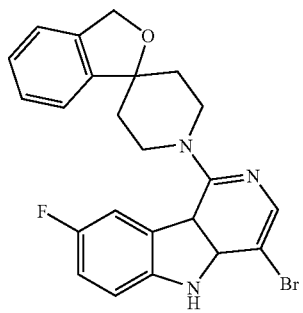 [SMILES: Fc1ccc2c(c1)C1C(N3CCC4(CC3)OCc3ccccc34)=NC=C(Br)C1N2]

4-Bromo-1-chloro-8-fluoro-5H-pyrido[4,3-b]indole (150 mg, 0.501 mmol) and 3H-spiro[2-benzofuran-1,4'-piperidinium]chloride (565 mg, 2.504 mmol) were placed in a vial and suspended in diglyme (3 mL) and Hunig's Base (0.875 mL, 5.01 mmol). The reaction mixture was heated to 150° C. for 4 days. The solution was cooled to ambient temperature, diluted with EtOAc and washed with water. The organic layer was separated, dried over magnesium sulfate, filtered and concentrated. The crude residue was purified on silica gel (EtOAc/hexanes gradient elution).

Step 2. 8-Fluoro-1-(1'H,3H-spiro[2-benzofuran-1,4'-piperidin]-1'-yl)-5H-pyrido[4,3-b]indole-4-carboxamide

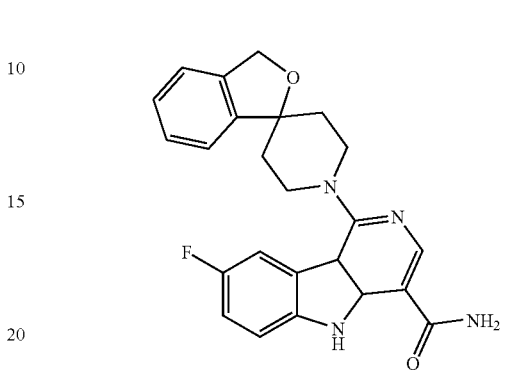

The title compound was completed according the procedures described in Example 7 steps 5 and 6.

According to the general procedures outlined in Examples 7-9, the following compounds were prepared:

| Compound Name | $R^1$ | Mass Spec (M + 1) |
|---|---|---|
| 8-fluoro-1-pyrrolidin-1-yl-5H-pyrido[4,3-b]indole-4-carboxamide | pyrrolidin-1-yl | 299 |
| 1-(ethylamino)-8-fluoro-5H-pyrido[4,3-b]indole-4-carboxamide | MeCH2NH- | 273 |
| 8-fluoro-1-(propylamino)-5H-pyrido[4,3-b]indole-4-carboxamide | MeCH2CH2NH- | 287 |
| 8-fluoro-1-piperidin-1-yl-5H-pyrido[4,3-b]indole-4-carboxamide | piperidin-1-yl | 313 |

-continued

| Compound Name | R¹ | Mass Spec (M + 1) |
|---|---|---|
| 8-fluoro-1-morpholin-4-yl-5H-pyrido[4,3-b]indole-4-carboxamide | morpholin-4-yl | 315 |
| 8-fluoro-1-(methylamino)-5H-pyrido[4,3-b]indole-4-carboxamide | HN-Me | 259 |
| 1-(cyclohexylamino)-8-fluoro-5H-pyrido[4,3-b]indole-4-carboxamide | HN-cyclohexyl | 327 |
| 1-(benzylamino)-8-fluoro-5H-pyrido[4,3-b]indole-4-carboxamide | HN-CH₂-Ph | 335 |
| 8-fluoro-1-(isobutylamino)-5H-pyrido[4,3-b]indole-4-carboxamide | HN-CH₂-CH(Me)₂ | 301 |
| 8-fluoro-1-(isopropylamino)-5H-pyrido[4,3-b]indole-4-carboxamide | HN-CH(Me)₂ | 287 |
| 1-[(cyclohexylmethyl)amino]-8-fluoro-5H-pyrido[4,3-b]indole-4-carboxamide | HN-CH₂-cyclohexyl | 341 |
| 1-(butylamino)-8-fluoro-5H-pyrido[4,3-b]indole-4-carboxamide | HN-(CH₂)₃-Me | 283 |

-continued

| Compound Name | R¹ | Mass Spec (M + 1) |
|---|---|---|
| 8-fluoro-1-(pentylamino)-5H-pyrido[4,3-b]indole-4-carboxamide | Me-(CH₂)₄-NH- | 315 |
| 1-(cyclobutylamino)-8-fluoro-5H-pyrido[4,3-b]indole-4-carboxamide | cyclobutyl-NH- | 299 |
| 1-(cyclopentylamino)-8-fluoro-5H-pyrido[4,3-b]indole-4-carboxamide | cyclopentyl-NH- | 313 |
| 1-(cycloheptylamino)-8-fluoro-5H-pyrido[4,3-b]indole-4-carboxamide | cycloheptyl-NH- | 341 |
| 1-(cyclooctylamino)-8-fluoro-5H-pyrido[4,3-b]indole-4-carboxamide | cyclooctyl-NH- | 355 |
| 8-fluoro-1-[(4-methylcyclohexyl)amino]-5H-pyrido[4,3-b]indole-4-carboxamide | 4-methylcyclohexyl-NH- | 341 |
| 8-fluoro-1-[(2-hydroxycyclohexyl)amino]-5H-pyrido[4,3-b]indole-4-carboxamide | 2-hydroxycyclohexyl-NH- | 343 |

-continued

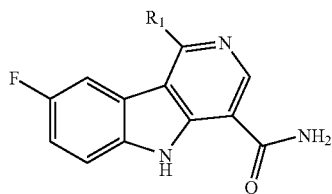

| Compound Name | R¹ | Mass Spec (M + 1) |
|---|---|---|
| 8-fluoro-1-[(2-methylcyclohexyl)amino]-5H-pyrido[4,3-b]indole-4-carboxamide | 2-methylcyclohexyl-NH- | 341 |
| 8-fluoro-1-[(trans-4-hydroxycyclohexyl)amino]-5H-pyrido[4,3-b]indole-4-carboxamide | trans-4-hydroxycyclohexyl-NH- | 343 |
| 8-fluoro-1-(tetrahydro-2H-pyran-4-ylamino)-5H-pyrido[4,3-b]indole-4-carboxamide | tetrahydro-2H-pyran-4-yl-NH- | 329 |
| 8-fluoro-1-(heptylamino)-5H-pyrido[4,3-b]indole-4-carboxamide | heptyl-NH- | 343 |
| 8-fluoro-1-[(1,2,2-trimethylpropyl)amino]-5H-pyrido[4,3-b]indole-4-carboxamide | 1,2,2-trimethylpropyl-NH- | 329 |
| 8-fluoro-1-(hexylamino)-5H-pyrido[4,3-b]indole-4-carboxamide | hexyl-NH- | 329 |

-continued

| Compound Name | R¹ | Mass Spec (M + 1) |
|---|---|---|
| 8-fluoro-1-(octylamino)-5H-pyrido[4,3-b]indole-4-carboxamide | 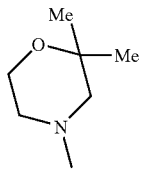 | 357 |
| 1-(2,2-dimethylmorpholin-4-yl)-8-fluoro-5H-pyrido[4,3-b]indole-4-carboxamide |  | 343 |
| 1-(3,3-difluoropyrrolidin-1-yl)-8-fluoro-5H-pyrido[4,3-b]indole-4-carboxamide | 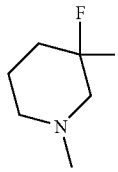 | 335 |
| 1-(3,3-difluoropiperidin-1-yl)-8-fluoro-5H-pyrido[4,3-b]indole-4-carboxamide | | 349 |
| 8-fluoro-1-(4-hydroxypiperidin-1-yl)-5H-pyrido[4,3-b]indole-4-carboxamide | 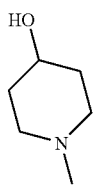 | 329 |
| ethyl 4-{[4-(aminocarbonyl)-8-fluoro-5H-pyrido[4,3-b]indol-1-yl]amino}piperidine-1-carboxylate | 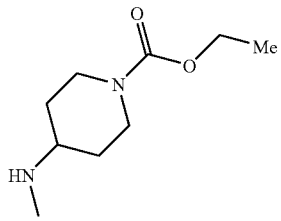 | 400 |

-continued

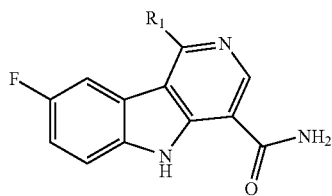

| Compound Name | R¹ | Mass Spec (M + 1) |
|---|---|---|
| 1-[(1-benzylpiperidin-4-yl)amino]-8-fluoro-5H-pyrido[4,3-b]indole-4-carboxamide | | |
| 8-fluoro-1-[3-(hydroxymethyl)piperidin-1-yl]-5H-pyrido[4,3-b]indole-4-carboxamide | | 343 |
| 8-fluoro-1-(4-phenyl-3,6-dihydropyridin-1(2H)-yl)-5H-pyrido[4,3-b]indole-4-carboxamide | | 387 |
| 1-(4-benzyl-4-hydroxypiperidin-1-yl)-8-fluoro-5H-pyrido[4,3-b]indole-4-carboxamide | | 419 |
| 1-(4-benzyl-3,6-dihydropyridin-1(2H)-yl)-8-fluoro-5H-pyrido[4,3-b]indole-4-carboxamide | | 401 |

-continued

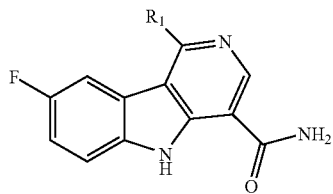

| Compound Name | R¹ | Mass Spec (M + 1) |
|---|---|---|
| 1-(4-benzylidenepiperidin-1-yl)-8-fluoro-5H-pyrido[4,3-b]indole-4-carboxamide | | 401 |
| 8-fluoro-1-(4-phenylpiperidin-1-yl)-5H-pyrido[4,3-b]indole-4-carboxamide | | 389 |
| 8-fluoro-1-(3-hydroxypiperidin-1-yl)-5H-pyrido[4,3-b]indole-4-carboxamide | | 329 |
| 8-fluoro-1-(2-phenylpiperidin-1-yl)-5H-pyrido[4,3-b]indole-4-carboxamide | | |
| 8-fluoro-1-{[(1S,2R)-2-(methoxymethyl)cyclopentyl]amino}-5H-pyrido[4,3-b]indole-4-carboxamide | | 357 |
| 8-fluoro-1-{[(1R)-1,2,2-trimethylpropyl]amino}-5H-pyrido[4,3-b]indole-4-carboxamide | | 329 |
| 8-fluoro-1-{[(1S)-1,2,2-trimethylpropyl]amino}-5H-pyrido[4,3-b]indole-4-carboxamide | | 329485 |

-continued

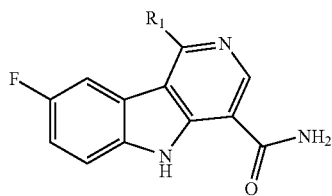

| Compound Name | R¹ | Mass Spec (M + 1) |
|---|---|---|
| N-[4-(aminocarbonyl)-8-fluoro-5H-pyrido[4,3-b]indol-1-yl]-3-methyl-D-valyl-N,3-dimethylvalinamide | | 485 |
| N-[4-(aminocarbonyl)-8-fluoro-5H-pyrido[4,3-b]indol-1-yl]-3-methyl-L-valyl-N,3-dimethylvalinamide | | 485 |
| 1-(bicyclo[2.2.1]hept-2-ylamino)-8-fluoro-5H-pyrido[4,3-b]indole-4-carboxamide | | 339 |
| 1-{[(1R)-1-cyclohexylethyl]amino}-8-fluoro-5H-pyrido[4,3-b]indole-4-carboxamide | | 355 |
| 8-fluoro-1-(3-phenylpiperidin-1-yl)-5H-pyrido[4,3-b]indole-4-carboxamide | | 389 |
| 8-fluoro-1-(3-phenylpiperidin-1-yl)-5H-pyrido[4,3-b]indole-4-carboxamide | | 403 |

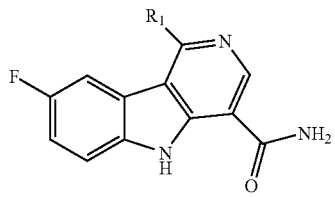

| Compound Name | R[1] | Mass Spec (M + 1) |
|---|---|---|
| 8-fluoro-1-[(1-hydroxypropyl)amino]-5H-pyrido[4,3-b]indole-4-carboxamide | Me, OH, HN | 303 |
| 8-fluoro-1-(1'H,3H-spiro[2-benzofuran-1,4'-piperidin]-1'-yl)-5H-pyrido[4,3-b]indole-4-carboxamide | | 417 |

EXAMPLE 10

1-Amino-5H-pyrido[4,3-b]indole-4-carboxamide

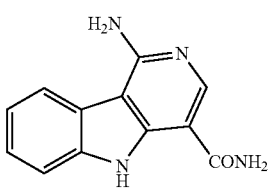

Step 1. Methyl 4-(1H-1,2,3-benzotriazol-1-yl)-6-chloronicotinate

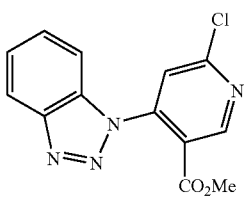 [SMILES: COC(=O)c1cnc(Cl)cc1-n1nnc2ccccc21]

A 1:1 mixture of benzotriazole and methyl 4,6-dichloronicotinate was heated neat in a preheated oil bath at 150° C. for a period of 10-15 min. The reaction mixture was cooled to room temperature, diluted with EtOAc and washed successively with saturated NaHCO₃ and brine. The organic phase was separated, dried over MgSO₄ and filtered. After evaporation of the organic solvent, the isomers in the residue were purified and separated by flash chromatography (10-70% EtOAc in hexanes) to provide the title compound as a white solid.

¹H NMR (Acetone-d₆) δ 9.05 (1H, s), 8.20 (1H, d), 8.05 (1H, s), 7.85 (1H, d), 7.75 (1H, t), 7.60 (1H, t), 3.65 (3H, s).

Step 2. Methyl 1-chloro-5H-pyrido[4,3-b]indole-4-carboxylate

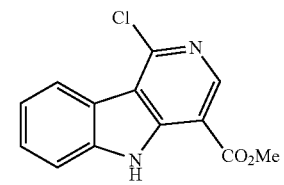 [SMILES: COC(=O)c1cnc(Cl)c2c1[nH]c1ccccc12]

A suspension of methyl 4-(1H-1,2,3-benzotriazol-1-yl)-6-chloronicotinate in PPA (1 M) was heated in a preheated oil bath at 150° C. for a period of 10-15 min. The reaction mixture was cooled to room temperature, poured slowly and carefully into an aqueous solution containing NaHCO₃ solid. The aqueous phase was extracted with EtOAc, washed with brine, and the organic phase was separated, dried over MgSO₄ and filtered. After evaporation of the organic solvent, the residue was purified by flash chromatography (10-70% EtOAc in hexanes) to provide the title compound as a pale yellow solid.

Step 3. 1-Chloro-5H-pyrido[4,3-b]indole-4-carboxamide

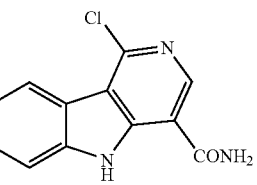

A mixture containing methyl 1-chloro-5H-pyrido[4,3-b]indole-4-carboxylate and LiNH₂ (prepared in situ from ammonia and n-BuLi; 1.0 M in THF; 3.5 equiv) in THF (0.09 M) was heated in a microwave reactor at 100° C. for 1 min in a sealed tube. The reaction mixture was cooled to room temperature and partitioned between EtOAc and saturated NaHCO₃. After separation of the organic phase, the aqueous phase was extracted again with EtOAc, and the combined organic phases were washed with brine, dried over MgSO₄ and filtered. After evaporation of the organic solvent, the residue was purified by flash chromatography (10-70% EtOAc in hexanes) to provide the title compound as a white solid.

Step 4.
1-Amino-5H-pyrido[4,3-b]indole-4-carboxamide

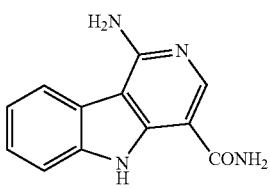 [SMILES: NC(=O)c1cnc(N)c2c1[nH]c1ccccc12]

A mixture of 1-chloro-5H-pyrido[4,3-b]indole-4-carboxamide in conc. NH₄OH (0.07 M) was heated in a microwave reactor at 160° C. for 1 h in a sealed tube. The reaction mixture was cooled to room temperature and partitioned between THF/EtOAc and saturated NaHCO₃. After separation of the organic phase, the aqueous phase was extracted again with THF/EtOAc, and the combined organic phases were washed with brine, dried over Na₂SO₄ and filtered. After evaporation of the organic solvents, the residue was purified by flash chromatography (0-10% MeOH in EtOAc) to provide the title compound as an off-white solid.

¹H NMR (DMSO-d₆) δ 11.50 (1H, s), 8.50 (1H, s), 8.30 (1H, d), 7.85 (1H, br s), 7.75 (1H, d), 7.35 (1H, t), 7.20 (1H, t), 7.15 (1H, br s), 6.80 (2H, br s).

EXAMPLE 11

1-Amino-8-bromo-5H-pyrido[4,3-b]indole-4-carboxamide

Step 1. 8-Bromo-1-chloro-5H-pyrido[4,3-b]indole-4-carboxamide

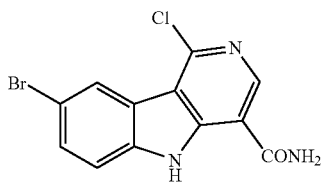 [SMILES: NC(=O)c1cnc(Cl)c2c1[nH]c1ccc(Br)cc12]

To a suspension of 1-chloro-5H-pyrido[4,3-b]indole-4-carboxamide (Example 10 Step 3) in AcOH (0.15 M) at room temperature was added Br₂ (10 equiv) to provide a homogeneous mixture. After standing at room temperature a precipitate formed, and after 1 h, a suspension of Zn powder (excess) in THF was added in a cold water bath. After a period of 10 min, the reaction mixture was poured over THF/EtOAc and saturated NaHCO₃. After separation of the organic phase, the aqueous phase was extracted again with THF/EtOAc, and the combined organic phases were washed with brine, dried over MgSO₄ and filtered. After evaporation of the organic solvents, the residue was purified by flash chromatography (10-70% EtOAc in hexanes) to provide the title compound as a yellow solid.

Step 2.
1-Amino-8-bromo-5H-pyrido[4,3-b]indole-carboxamide

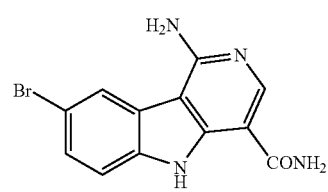

The title compound was prepared as described in Example 10, Step 4 using 8-bromo-1-chloro-5H-pyrido[4,3-b]indole-4-carboxamide as starting material and a 2:1 (v/v) mixture of EtOH and conc. NH₄OH (0.015 M).

¹H NMR (DMSO-d₆) δ 11.65 (1H, s), 8.55 (1H, d), 8.50 (1H, s), 7.85 (1H, br s), 7.70 (1H, d), 7.45 (1H, dd), 7.15 (1H, br s), 6.95 (2H, br s).

EXAMPLE 12

1-Amino-7-bromo[1]benzothieno[3,2-c]pyridine-4-carboxamide

Step 1. 1-Benzothiophene-2-carbaldehyde

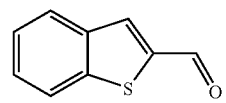

To a solution of benzothiophene in dry THF (0.6 M) was added at −78° C., BuLi (1.2 equiv) dropwise over 30 min. The mixture was stirred at −78° C. for 1 h, DMF (2 equiv) was added and the mixture was stirred for 1 h. Saturated NH₄Cl was added and the mixture was extracted with EtOAc. The combined organic extracts were washed with brine, dried over MgSO₄, filtered, and concentrated to give the title compound as an oil.

Step 2. (2E)-3-(1-Benzothien-2-yl)acrylic acid

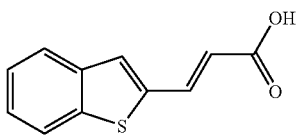 [SMILES: O=C(O)/C=C/c1cc2ccccc2s1]

To a mixture of 1-benzothiophene-2-carbaldehyde, malonic acid (1.5 equiv) and pyridine (2.5 equiv) was added piperidine (0.1 equiv). The mixture was heated to reflux for 6 h, cooled and poured into H$_2$O and filtered. Air drying over night gave the title compound.

Step 3. (2E)-3-(1-Benzothien-2-yl)acryloyl azide

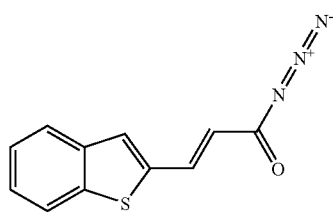 [SMILES: [N-]=[N+]=NC(=O)/C=C/c1cc2ccccc2s1]

To a stirring mixture of (2E)-3-(1-benzothien-2-yl)acrylic acid and Et$_3$N (1.3 equiv) in acetone (0.22 M) at 0° C. was added isobutyl chloroformate (1.3 equiv). The mixture was stirred at 0° C. for 1 h. A solution of NaN$_3$ (1.3 equiv) in H$_2$O was added, the mixture was stirred at 0° C. for 0.5 h and then at room temperature for 0.5 h. The mixture was poured into H$_2$O, stirred and filtered to give the title compound.

Step 4. [1]Benzothieno[3,2-c]pyridin-1(2H)-one

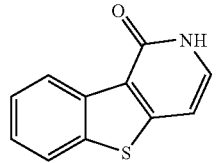 [SMILES: O=c1[nH]ccc2sc3ccccc3c12]

A suspension of (2E)-3-(1-benzothien-2-yl)acryloyl azide in diphenyl ether (9.2 equiv) and Bu$_3$N (1.1 equiv) was heated to reflux for 1 h. A solution resulted. The mixture was cooled to 40-50° C. Hexane was added; the mixture was stirred for 30 min, filtered, and washed with hexanes to give the title compound as a yellow solid.

Step 5. 4-Bromo[1]benzothieno[3,2-c]-pyridin-1(2H)-one

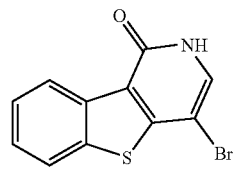 [SMILES: O=c1[nH]cc(Br)c2sc3ccccc3c12]

To a suspension of [1]benzothieno[3,2-c]pyridin-1(2H)-one in AcOH (0.52 M) was added Br$_2$ (1.1 equiv) at room temperature. The mixture was heated to reflux for 1.5 h, cooled to room temperature, poured into H$_2$O and stirred for 30 min. The mixture was filtered and washed with H$_2$O to give the title compound.

Step 6. 1-Oxo-1,2-dihydro[1]benzothieno[3,2-c]pyridine-4-carbonitrile

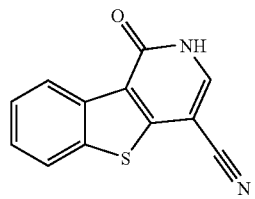 [SMILES: N#Cc1c[nH]c(=O)c2c1sc1ccccc12]

A suspension of 4-bromo[1]benzothieno[3,2-c]pyridin-1(2H)-one and CuCN (1.5 equiv) in NMP (0.41 M) was heated to reflux for 1.5 h. The mixture was cooled to room temperature and added to a stirring 2 N HCl solution. The mixture was stirred at room temperature for 1 h, filtered, washed with H$_2$O and dried to give a dark grey solid. The crude product was heated to reflux with activated charcoal in methyl ethyl ketone (MEK) for 0.5 h and filtered through a short pad of silica gel, eluted with more MEK to give after concentration the title compound as a light brown solid.

Step 7. 7-Bromo-1-oxo-1,2-dihydro[1]benzothieno[3,2-c]pyridine-4-carboxamide

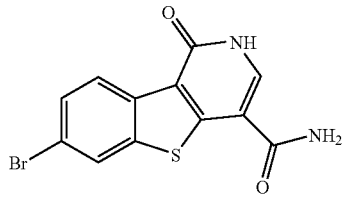 [SMILES: NC(=O)c1c[nH]c(=O)c2c1sc1cc(Br)ccc12]

To a suspension of 1-oxo-1,2-dihydro[1]benzothieno[3,2-c]pyridine-4-carbonitrile in AcOH (0.29 M) was added Br$_2$ (4.5 equiv), the mixture was heated to reflux for 1 h. The mixture was poured into an aqueous solution of Na$_2$S$_2$O$_5$ (0.1 M), filtered, washed with H$_2$O and dried to give the title compound.

Step 8. 7-Bromo-1-chloro[1]benzothieno[3,2-c]pyridine-4-carbonitrile

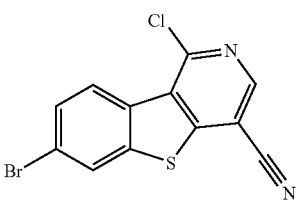 [SMILES: N#Cc1cnc(Cl)c2c1sc1cc(Br)ccc12]

A mixture of 7-bromo-1-oxo-1,2-dihydro[1]benzothieno[3,2-c]pyridine-4-carboxamide and POCl$_3$ (29 equiv) was heated to refluxed for 8 h. The mixture was poured onto ice, neutralized with NaHCO$_3$, filtered, washed with H$_2$O and

Step 9. 7-Bromo-1-[(4-methoxybenzyl)amino][1]benzothieno[3,2-c]pyridine-4-carbonitrile

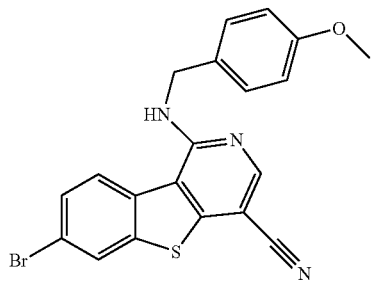 [SMILES: COc1ccc(CNc2ncc(C#N)c3sc4cc(Br)ccc4c23)cc1]

A mixture of 7-bromo-1-chloro[1]benzothieno[3,2-c]pyridine-4-carbonitrile, 4-methoxybenzyamine (1 equiv) and K$_2$CO$_3$ (1 equiv) in DMF (0.3 M) was heated to 100° C. for 1 h. The mixture was poured into H$_2$O, stirred for 15 min and filtered. The crude product was air dried over night and then heated to reflux in EtOH for 1 h, filtered and washed with EtOH to give the title compound.

Step 10. 1-Amino-7-bromo[1]benzothieno[3,2-c]pyridine-4-carboxamide

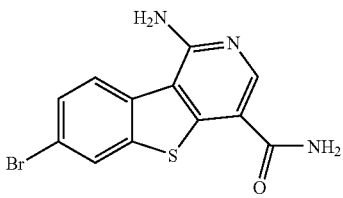 [SMILES: NC(=O)c1cnc(N)c2c1sc1cc(Br)ccc12]

A solution of 7-bromo-1-[(4-methoxybenzyl)amino][1]benzothieno[3,2-c]pyridine-4-carbonitrile in conc. H$_2$SO$_4$ (0.04 M) was stirred at room temperature for 2 h. The mixture was poured into H$_2$O, neutralized with K$_3$PO$_4$, filtered, washed with H$_2$O and dried. The crude product was swished with MeOH to give the title compound.

$^1$H NMR (DMSO-d$_6$) δ 8.70 (1H, s), 8.45 (1H, d), 8.40 (1H, s), 8.15 (1H, br s), 7.70 (1H, d), 7.50 (3H, br m).

EXAMPLE 13

1-Amino-7-[4-(methylsulfonyl)phenyl][1]benzothieno[3,2-c]pyridine-4-carboxamide

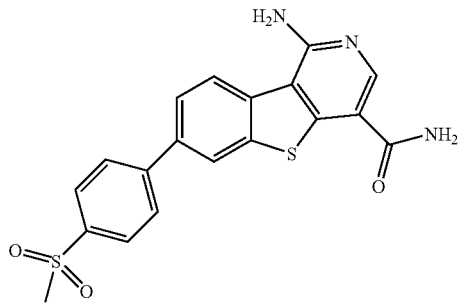 [SMILES: CS(=O)(=O)c1ccc(-c2ccc3c(c2)sc2c(C(N)=O)cnc(N)c23)cc1]

Step 1. 1-[(4-Methoxybenzyl)amino]-7-[4-(methylsulfonyl)phenyl][1]benzothieno[3,2-c]pyridine-4-carbonitrile

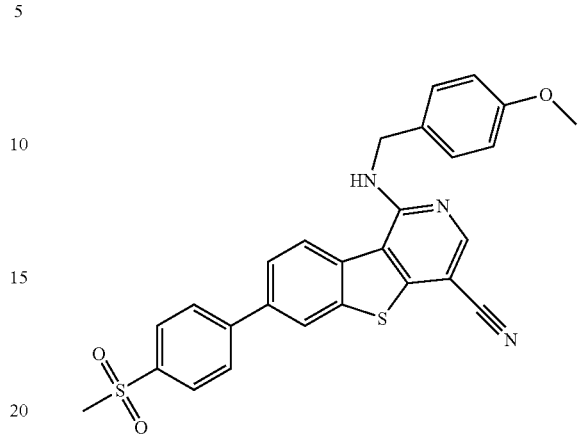

To a suspension of 7-bromo-1-[(4-methoxybenzyl)amino][1]benzothieno[3,2-c]pyridine-4-carbonitrile (Example 12, Step 9) and [4-(methylsulfonyl)phenyl]boronic acid (1.5 equiv) in 1-PrOH/H$_2$O (4.5/1) (0.11 M) was added Pd$_2$(dba)$_3$ (0.03 equiv), Ph$_3$P (0.06 equiv) and Et$_2$NH (1.2 equiv). The mixture was degassed and heated to 150° C. for 10 min in a microwave reactor. The mixture was diluted with H$_2$O and filtered. The crude product was swished with hot EtOH to give the title compound.

Step 2. 1-Amino-7-[4-(methylsulfonyl)phenyl][1]benzothieno[3,2-c]pyridine-4-carboxamide

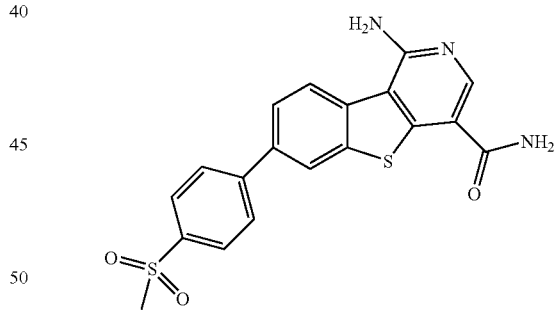

A solution of 1-[(4-methoxybenzyl)amino]-7-[4-(methylsulfonyl)phenyl][1]benzothieno[3,2-c]pyridine-4-carbonitrile in conc. H$_2$SO$_4$ (45 equiv) was stirred at room temperature for 2 h and then poured into H$_2$O. The mixture was neutralized with K$_3$PO$_4$, filtered, washed with H$_2$O and dried. The crude product was purified by flash chromatography on silica gel, eluted with 10% MeOH in EtOAc to provide the title compound.

$^1$H NMR (DMSO-d$_6$) δ 8.70 (1H, s), 8.60 (1H, d), 8.50 (1H, s), 8.10 (2H, d), 8.05 (2H, d), 7.90 (1H, d), 7.20 (2H, s), 3.30 (3H, s). 2H not observed.

MS (+ESI): m/z=397.9 [M+1].

EXAMPLE 14

1-Amino-7-[4-(trifluoromethyl)phenyl][1]benzothieno[3,2-c]pyridine-4-carboxamide

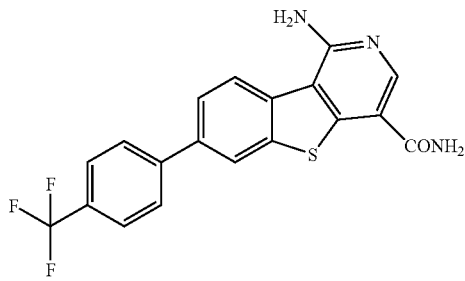 [SMILES: NC(=O)c1cnc(N)c2c1sc1cc(-c3ccc(C(F)(F)F)cc3)ccc12]

Step 1. 1-[(4-Methoxybenzyl)amino]-7-[4-(trifluoromethyl)phenyl][1]benzothieno[3,2-c]pyridine-4-carbonitrile

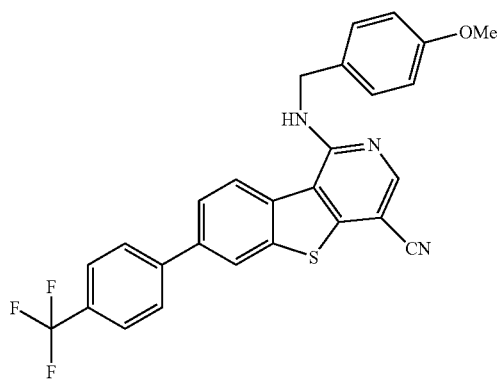 [SMILES: COc1ccc(CNc2ncc(C#N)c3sc4cc(-c5ccc(C(F)(F)F)cc5)ccc4c23)cc1]

A mixture containing 7-bromo-1-[(4-methoxybenzyl)amino][1]benzothieno[3,2-c]pyridine-4-carbonitrile (Example 12, Step 9), 4-trifluoromethylphenylboronic acid (1.7 equiv), Pd(OAc)$_2$ (0.14 equiv), Ph$_3$P (0.42 equiv), Na$_2$CO$_3$ 2 M (2.9 equiv) in 1-PrOH/DMF (3/1) (0.09 M) was degassed and heated at 100° C. for 3 h. The resulting mixture was concentrated to dryness, and the crude solid was washed successively with H$_2$O and MeOH to provide the title compound as a brown solid.

Step 2. 1-Amino-7-[4-(trifluoromethyl)phenyl][1]benzothieno[3,2-c]pyridine-4-carboxamide

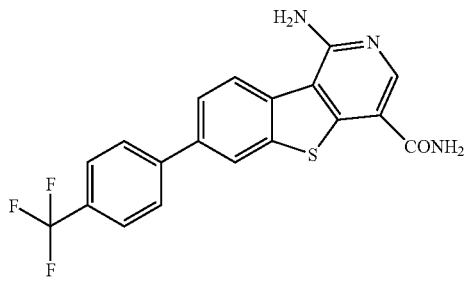 [SMILES: NC(=O)c1cnc(N)c2c1sc1cc(-c3ccc(C(F)(F)F)cc3)ccc12]

1-[(4-Methoxybenzyl)amino]-7-[4-(trifluoromethyl)phenyl][1]benzothieno[3,2-c]pyridine-4-carbonitrile was placed in a flask cooled to 0° C. before conc. H$_2$SO$_4$ (excess) was added dropwise under vigorous stirring. The final mixture was warmed to room temperature and, after 1 h, poured into THF/EtOAc and aqueous NaHCO$_3$ previously saturated with NaCl solid. After separation of the organic phase, the aqueous phase was extracted again with THF/EtOAc, and the combined organic phases were dried over MgSO$_4$ and filtered. After evaporation of the organic solvents, the crude material was purified by a wash with Et$_2$O to provide the title compound as a yellow solid.

$^1$H NMR (DMSO-d$_6$) δ 8.70 (1H, s), 8.60 (1H, d), 8.50 (1H, s), 8.10 (3H, m), 7.90 (3H, m), 7.40 (1H, br s), 7.20 (2H, br s).

EXAMPLE 15

1-Amino[1]benzothieno[3,2-c]pyridine-4,7-dicarboxamide

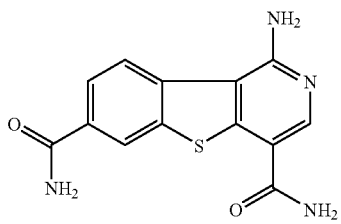 [SMILES: NC(=O)c1ccc2c(c1)sc1c(C(N)=O)cnc(N)c12]

Step 1. 1-Amino[1]benzothieno[3,2-c]pyridine-4,7-dicarbonitrile

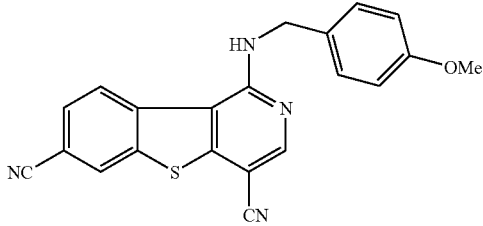

To a microwave reaction vessel was added 7-bromo-1-[(4-methoxybenzyl)amino][1]benzothieno[3,2-c]pyridine-4-carbonitrile (Example 12, Step 9), Zn(CN)$_2$ (1.3 equiv), Pd(Ph$_3$P)$_4$ (0.1 equiv), and DMF (0.06 M). After sealing, the tube was degassed via a needle through the septum, and the reaction was set up on the Smith Creator microwave machine for 5 min at 150° C. The mixture was then added to H$_2$O and the resulting solid was collected by filtration and dried under vacuum. The crude was then stirred with 1:10 EtOAc:hexanes containing a trace of acetone, to give after filtration, a pale brown solid which was used as such for the next step.

Step 2. 1-Amino[1]benzothieno[3,2-c]pyridine-4,7-dicarboxamide

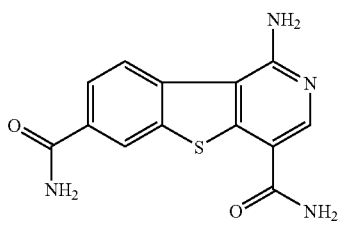 [SMILES: NC(=O)c1ccc2c(c1)sc1c(C(N)=O)cnc(N)c12]

The crude product of Step 1 was stirred in a 1:1 mixture (m/m) of PPA:CH$_3$SO$_3$H (0.03 M) for 1.5 h at 130° C. After cooling, the mixture was carefully added to a stirring mixture of saturated NaHCO$_3$. The product was then extracted with EtOAc/THF and the organic layer was washed with H$_2$O and brine. After drying (MgSO$_4$), filtering, and removal of solvent, the crude was purified by flash chromatography. Elution was effected with EtOAc and 1:10 MeOH:EtOAc to give a tan coloured solid.

$^1$H NMR (DMSO-d$_6$) δ 8.75 (1H, s), 8.55-8.50 (2H, m), 8.15 (1H, br s), 8.10 (1H, br s), 8.00 (1H, m), 7.50 (1H, br s), 7.40 (1H, br s), 7.25 (2H, br s).

MS (+APCI): m/z=287.0 [M+1].

EXAMPLE 16

1-Amino-7-[(E)-2-(4-fluorophenyl)vinyl][1]benzothieno[3,2-c]pyridine-4-carboxamide

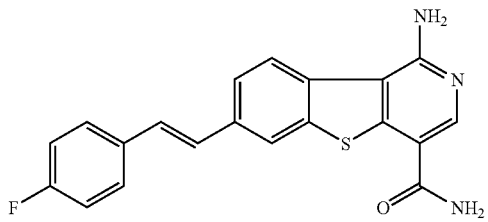 [SMILES: NC(=O)c1cnc(N)c2c1sc1cc(/C=C/c3ccc(F)cc3)ccc12]

Step 1. 7-[(E)-2-(4-fluorophenyl)vinyl]-1-[(4-methoxybenzyl)amino][1]benzothieno[3,2-c]pyridine-4-carbonitrile

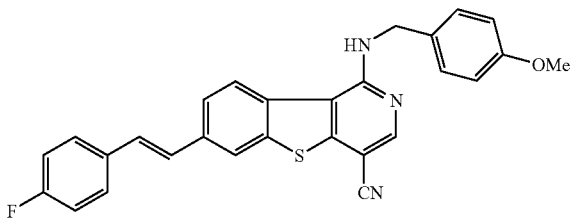 [SMILES: COc1ccc(CNc2ncc(C#N)c3sc4cc(/C=C/c5ccc(F)cc5)ccc4c23)cc1]

To a suspension of 7-bromo-1-[(4-methoxybenzyl)amino][1]benzothieno[3,2-c]pyridine-4-carbonitrile (Example 12, Step 9) in 1-propanol (0.1 M) was added [(E)-2-(4-fluorophenyl)vinyl]boronic acid (1.5 equiv), 2.0 M aqueous Na$_2$CO$_3$ solution (2.5 equiv), and a 3:1 mixture of Ph$_3$P:Pd(OAc)$_2$ (0.1 equiv). The mixture was degassed and then stirred at 100° C. for 2.5 h, and was then partitioned between EtOAc/THF and H$_2$O. The organic layer was washed with H$_2$O and brine, and was then dried (MgSO$_4$), filtered, and evaporated. The crude material was purified by flash chromatography, eluting with 1:1 Et$_2$O:hexanes. The product was stirred with 1:10 EtOAc:hexanes containing trace acetone to yield the title compound as a pale yellow solid after filtration.

Step 2. 1-Amino-7-[(E)-2-(4-fluorophenyl)vinyl][1]benzothieno[3,2-c]pyridine-4-carboxamide

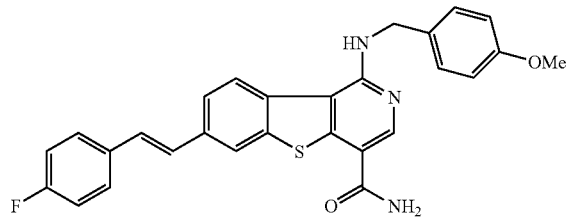 [SMILES: COc1ccc(CNc2ncc(C(N)=O)c3sc4cc(/C=C/c5ccc(F)cc5)ccc4c23)cc1]

To a suspension of the product of Step 1 in toluene (0.022 M) was added KOSiMe$_3$ (5 equiv). The mixture was brought to reflux for 30 min, and was then stirred at room temperature overnight. Following removal of solvent under vacuum, the residue was partitioned between EtOAc/THF and H$_2$O. The resulting emulsion was filtered, and the organic layer was dried (MgSO$_4$), filtered, and evaporated. The crude was dissolved in TFA (0.022 M), and the resulting solution was stirred at 45° C. for 1.5 h. After removal of the TFA under vacuum, the crude material was purified by flash chromatography, eluting 1:1 EtOAc:hexanes, EtOAc, and 1:30 MeOH:EtOAc. The product was stirred with 1:10 EtOAc:hexanes containing trace acetone to give the title compound, after filtration, as an off-white solid.

$^1$H NMR (acetone-d$_6$) δ 8.75 (1H, s), 8.40 (1H, m), 8.25 (1H, m), 7.80 (1H, m), 7.75 (2H, m), 7.45 (2H, m), 7.20 (2H, m), 6.55 (2H, br s). 2H not observed.

MS (+ESI): m/z=363.9 [M+1].

EXAMPLE 17

1-Amino-7-[3-(trifluoromethyl)phenyl][1]benzothieno[3,2-c]pyridine-4-carboxamide

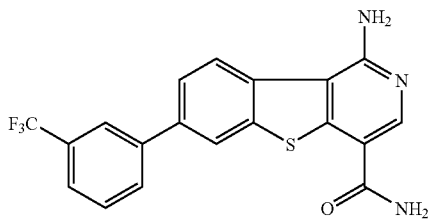 [SMILES: NC(=O)c1cnc(N)c2c1sc1cc(-c3cccc(C(F)(F)F)c3)ccc12]

A mixture of 1-amino7-bromo[1]benzothieno[3,2-c]pyridine-4-carboxamide (Example 12, Step 10), 3-trifluoromethylboronic acid (1.5 equiv), PdCl$_2$dppf (0.1 equiv), Na$_2$CO$_3$ 1 M (3.0 equiv) in DMF (0.15 M) was heated in the microwave reactor at 120° C. for 10 min. The reaction mixture was partitioned between EtOAc and H$_2$O with the addition of DMSO. The organic phase was separated, dried over Na$_2$SO$_4$, filtered, evaporated and purified by flash chromatography (10% MeOH in CH$_2$Cl$_2$) to provide the title compound.

$^1$H NMR (DMSO-d$_6$) δ 8.75 (1H, s), 8.60 (1H, d), 8.50 (1H, s), 8.15 (2H, m), 8.10 (1H, br s), 7.90 (1H, d), 7.75 (2H, m), 7.35 (1H, br s), 7.20 (2H, br s).

EXAMPLE 18

1-Amino-7-(3-isopropylphenyl)[1]benzothieno[3,2-c]pyridine-4-carboxamide

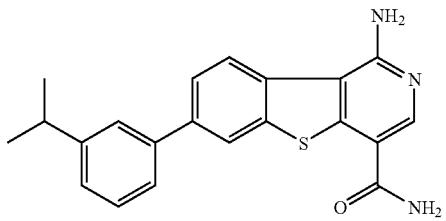 [SMILES: CC(C)c1cccc(-c2ccc3c(c2)sc2c(C(N)=O)cnc(N)c23)c1]

The title compound was prepared as described in Example 17 using 3-isopropylphenylboronic acid.

¹H NMR (DMSO-d₆) δ 8.75 (1H, s), 8.55 (1H, d), 8.35 (1H, s), 8.05 (1H, br s), 7.80 (1H, d), 7.70 (1H, s), 7.60 (1H, d), 7.45 (1H, t), 7.40 (1H, br s), 7.25 (1H, d), 7.15 (2H, br s), 3.05 (1H, m), 1.25 (6H, d).

EXAMPLE 19

1-Amino-7-pyridin-3-yl[1]benzothieno[3,2-c]pyridine-4-carboxamide

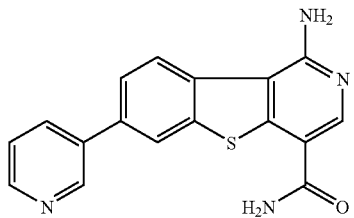

Step 1. 1-[(4-Methoxybenzyl)amino]-7-pyridin-3-yl[1]benzothieno[3,2-c]pyridine-4-carbonitrile

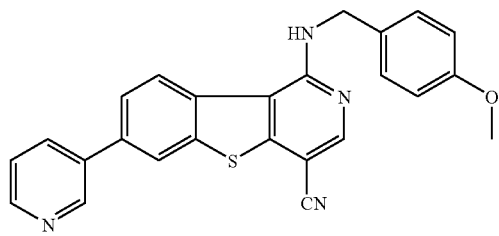 [SMILES: COc1ccc(CNc2ncc(C#N)c3sc4cc(-c5cccnc5)ccc4c23)cc1]

To a suspension of 7-bromo-1-[(4-methoxybenzyl)amino][1]benzothieno[3,2-c]pyridine-4-carbonitrile (Example 12, Step 9) in DMF (0.1 M) were added the pyridine-3-boronic acid 1,3-propanediol cyclic ester (1.5 equiv), 2 M Na₂CO₃ (3 equiv) and PdCl₂dppf (0.05 equiv). The mixture was heated in the microwave reactor at 110° C. for 10 min. The reaction mixture was partitioned between EtOAc and saturated NaHCO₃. The organic phase was separated, dried over MgSO₄, filtered, evaporated and purified by flash chromatography (70:30 hexanes/EtOAc to 100% EtOAc) to provide the title compound.

Step 2. 1-Amino-7-pyridin-3-yl[1]benzothieno[3,2-c]pyridine-4-carboxamide

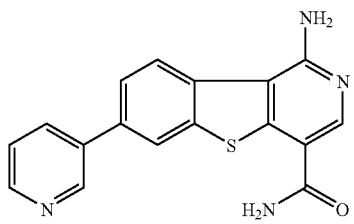

The title compound was prepared from 1-[(4-methoxybenzyl)amino]-7-pyridin-3-yl[1]benzothieno[3,2-c]pyridine-4-carbonitrile as described in Example 14, Step 2.

¹H NMR (DMSO-d₆) δ 8.75 (1H, s), 8.65 (1H, d), 8.55 (1H, d), 8.45 (1H, s), 8.25 (1H, d), 8.05 (1H, br s), 7.90 (1H, d), 7.55 (2H, m), 7.35 (1H, br s), 7.20 (2H, br s).

MS (+ESI): m/z=320.9 [M+1].

EXAMPLE 20

1-Amino-7-phenyl[1]benzothieno[3,2-c]pyridine-4-carboxamide

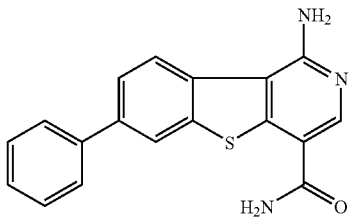 [SMILES: NC(=O)c1cnc(N)c2c1sc1cc(-c3ccccc3)ccc12]

To a suspension of 1-amino-7-bromo[1]benzothieno[3,2-c]pyridine-4-carboxamide (Example 12, Step 10) in DMF (0.1 M) was added phenylboronic acid (1.5 equiv). The mixture was degassed for 5 min, and 1 M Na₂CO₃ (3 equiv) and PdCl₂dppf (0.1 equiv) were added. It was heated is the microwave reactor at 120° C. for 10 min. The reaction mixture was partitioned between EtOAc and H₂O. The organic phase was separated, dried over MgSO₄, filtered, evaporated and purified by flash chromatography (EtOAc/MeOH) to provide the title compound.

¹H NMR (Acetone-d₆) δ 8.75 (1H, s), 8.50 (1H, d), 8.30 (1H, s), 7.80 (3H, m), 7.50 (2H, t), 7.40 (1H, m), 6.65 (2H, br s). 2H not observed.

MS (+ESI): m/z=319.9 [M+1].

EXAMPLE 21

1-Amino-7-{4-[(dimethylamino)methyl]phenyl}[1]benzothieno[3,2-c]pyridine-4-carboxamide

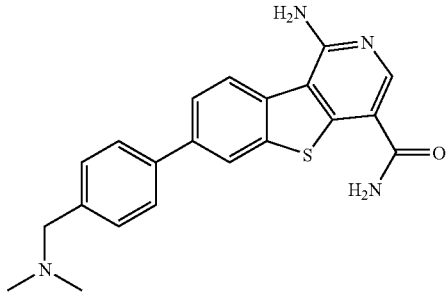 [SMILES: CN(C)Cc1ccc(-c2ccc3c(c2)sc2c(C(N)=O)cnc(N)c23)cc1]

Step 1. 7-{4-[(Dimethylamino)methyl]phenyl}-1-[(4-methoxybenzyl)amino][1]benzothieno[3,2-c]pyridine-4-carbonitrile

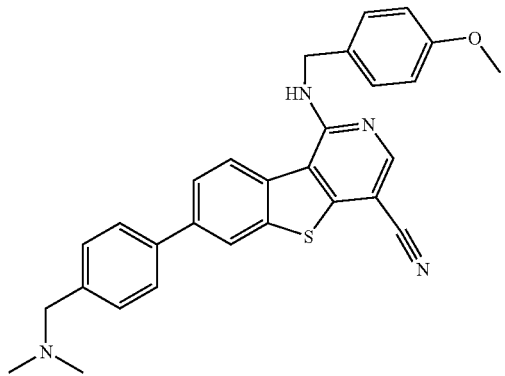

The title compound was prepared by the method described in Example 19, Step 1 using 7-bromo-1-[(4-methoxybenzyl)amino][1]benzothieno[3,2-c]pyridine-4-carbonitrile Example 12, Steep 9) and {4-[(dimethylamino)methyl]phenyl}boronic acid hydrochloride.

Step 2. 1-Amino-7-{4-[(dimethylamino)methyl]phenyl}[1]benzothieno[3,2-c]pyridine-4-carboxamide

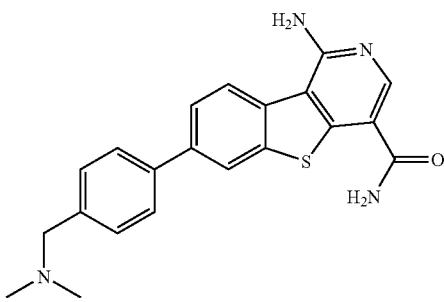 [SMILES: CN(C)Cc1ccc(-c2ccc3c(c2)sc2c(C(N)=O)cnc(N)c23)cc1]

The title compound was prepared from 7-{4-[(dimethylamino)methyl]phenyl}-1-[(4-methoxybenzyl)amino][1]benzothieno[3,2-c]pyridine-4-carbonitrile as described in Example 14, Step 2.

$^1$H NMR (DMSO-d$_6$) δ 8.70 (1H, s), 8.55 (1H, d), 8.35 (1H, s), 8.05 (1H, br s), 7.80 (3H, m), 7.45 (3H, m), 7.15 (2H, br s), 3.15 (2H, s), 2.20 (6H, s).

EXAMPLE 22

Methyl 1-amino-4-(aminocarbonyl)[1]benzothieno[3,2-c]pyridine-7-carboxylate

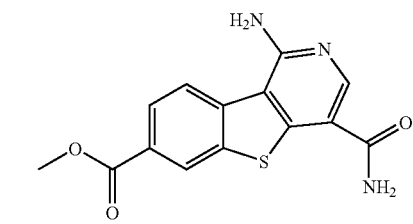 [SMILES: COC(=O)c1ccc2c(c1)sc1c(C(N)=O)cnc(N)c12]

Step 1. Methyl 4-cyano-1-[(4-methoxybenzyl)amino][1]benzothieno[3,2-c]pyridine-7-carboxylate

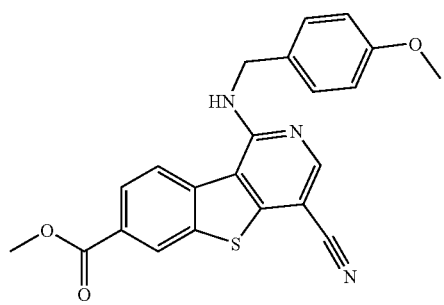

A suspension of Pd(OAc)$_2$ (0.26 equiv), Pd(Ph$_3$P)$_4$ (0.30 equiv), NaOAc (1.7 equiv) and 7-bromo-1-[(4-methoxybenzyl)amino][1]benzothieno[3,2-c]pyridine-4-carbonitrile (Example 12, Step 9) in a 1:1 (v/v) mixture of DMF and MeOH (1 M) was stirred at 110° C. under 160 psig of carbon monoxide in a sealed bomb for 18 h. The reaction media was poured in EtOAc and diluted with H$_2$O. The phases were separated and the organic layer washed with brine, dried over magnesium sulfate and concentrated under reduced pressure. The residue was purified by flash chromatography using EtOAc and hexanes gradient to yield the title compound.

Step 2. Methyl 1-amino-4-(aminocarbonyl)[1]benzothieno[3,2-c]pyridine-7-carboxylate

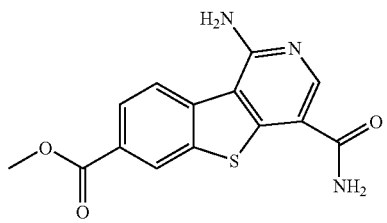 [SMILES: COC(=O)c1ccc2c(c1)sc1c(C(N)=O)cnc(N)c12]

The title compound was prepared from methyl 4-cyano-1-[(4-methoxybenzyl)amino][1]benzothieno[3,2-c]pyridine-7-carboxylate as described in Example 14, Step 2.

$^1$NMR (DMSO-d$_6$) δ 8.75 (1H, s), 8.65 (1H, s), 8.55 (1H, d), 8.10 (1H, br s), 8.05 (1H, d), 7.45 (1H, br s), 7.30 (2H, br s), 3.90 (3H, s).

EXAMPLE 23

1-Amino-4-(aminocarbonyl)[1]benzothieno[3,2-c]pyridine-7-carboxylic acid

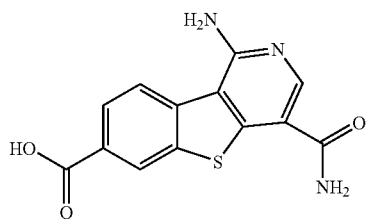 [SMILES: NC(=O)c1cnc(N)c2c1sc1cc(C(=O)O)ccc12]

A suspension of methyl methyl 1-amino-4-(aminocarbonyl)[1]benzothieno[3,2-c]pyridine-7-carboxylate (Example 22, Step 2) dissolved in THF and MeOH was treated with a solution of LiOH in H$_2$O (2.5 equiv). The reaction media became cloudy so H$_2$O, MeOH and THF were added until a clear solution ensued. After 18 h, analysis showed consumption of all the starting material. A large proportion of the volatiles were removed under reduced pressure. The remaining solution was treated with 1 N HCl. The precipitate was filtered off to obtain the title compound as a solid.

$^1$H NMR (DMSO-d$_6$) δ 13.5 (1H, br s), 8.75 (2H, br s), 8.65 (1H, d), 8.30 (1H, br s), 8.55 (1H, d), 8.10 (2H, m), 7.70 (1H, br s).

EXAMPLE 24

1-Amino-7-(trifluoromethyl)[1]benzothieno[3,2-c]pyridine-4-carboxamide

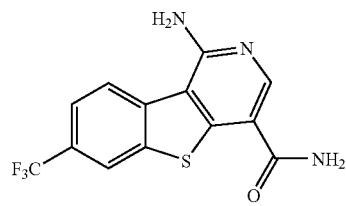 [SMILES: NC(=O)c1cnc(N)c2c1sc1cc(C(F)(F)F)ccc12]

Step 1. Ethyl 6-(trifluoromethyl)-1-benzothiophene-2-carboxylate

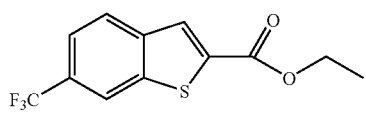

To a solution of DBU (1,8-diazabicyclo[5.4.0]undec-7-ene, 5 equiv) in THF (1 M) at 0° C. was added a solution of ethyl-2-mercaptoacetate (1.15 equiv) and the reaction stirred at 0° C. for 20 min. A solution of 2-fluoro4-(trifluoromethyl) benzaldehyde (1 equiv) in THF (2 M) was added and the reaction was stirred for an additional 2 h at 0° C. The reaction was diluted with half-saturated NH$_4$Cl and EtOAc. The organic layer was washed with brine and dried over magnesium sulfate. The volatiles were removed under reduced pressure to obtain the title compound as a viscous oil.

Step 2. 6-(Trifluoromethyl)-1-benzothiophene-2-carboxylic acid

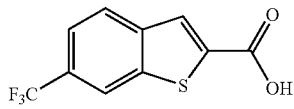

To ethyl 6-(trifluoromethyl)-1-benzothiophene-2-carboxylate dissolved in THF and MeOH was added a solution of LiOH in H$_2$O (1.5 equiv). The reaction media became cloudy so H$_2$O, MeOH and THF were added until a clear solution ensued (Final composition of media=2 THF:1 MeOH:1 H$_2$O) (0.2 M). After 1 h, analysis showed consumption of all the starting material. A large proportion of the volatiles were removed under reduced pressure. The remaining solution was treated with 1N HCl. The precipitate was filtered off and dissolved in a mixture of THF, MeOH and EtOAc. The organic solution was dried over magnesium sulfate and concentrated under reduced pressure to obtain the title compound as a solid. The latter was ground with a mortar and pestle and let dry overnight under high vacuum.

Step 3. N-Methoxy-N-methyl-6-(trifluoromethyl)-1-benzothiophene-2-carboxamide

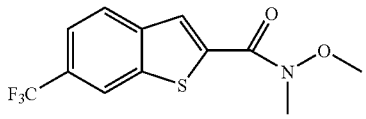 [SMILES: CON(C)C(=O)c1cc2ccc(C(F)(F)F)cc2s1]

To 6-(Trifluoromethyl)-1-benzothiophene-2-carboxylic acid dissolved in DMF (0.5 M) was added HATU (1.2 equiv) at 0° C. and the reaction was stirred for 2 min followed by addition of N,O-dimethylhydroxylamine hydrochloride (1.5 equiv). The reaction was stirred for 2 min prior to the addition of iPr$_2$NEt (5 equiv). The reaction was stirred for an additional 20 min at 0° C. The reaction was quenched with equivalent amounts of half-saturated aqueous NaHCO$_3$ and H$_2$O. The title compound was obtained as a solid and filtered on a Büchner funnel before being and air-dried.

Step 4. 6-(Trifluoromethyl)-1-benzothiophene-2-carbaldehyde

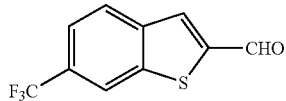

To N-methoxy-N-methyl-6-(trifluoromethyl)-1-benzothiophene-2-carboxamide as a solution in THF (0.2 M) at −15° C. was added a solution of LiAlH$_4$ in THF (0.5 M) dropwise via an addition funnel. After stirring at −15° C. for an additional 30 min, an aqueous 1 N KHSO$_4$ solution was added cautiously via an addition funnel. H$_2$O was added followed by EtOAc. The layers were separated and the aqueous layer was extracted once more with EtOAc. The combined organic layers were washed with 1 N HCl, then washed with brine and dried over magnesium sulfate. The volatiles were removed under reduced pressure to obtain the title compound as an oil that solidified under high vacuum.

Step 5. (2E)-3-[6-(Trifluoromethyl)-1-benzothien-2-yl]acrylic acid

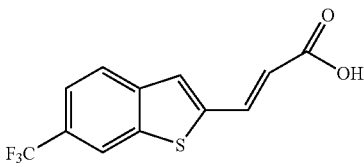 [SMILES: O=C(O)/C=C/c1cc2ccc(C(F)(F)F)cc2s1]

The title compound was prepared from 6-(trifluoromethyl)-1-benzothiophene-2-carbaldehyde as described in Example 12, Step 2.

Step 6. (2E)-3-[6-(Trifluoromethyl)-1-benzothien-2-yl]acryloyl azide

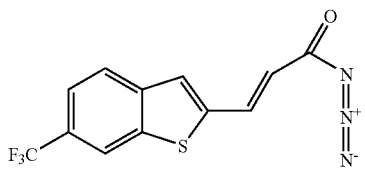 [SMILES: [N-]=[N+]=NC(=O)/C=C/c1cc2ccc(C(F)(F)F)cc2s1]

The title compound was prepared from (2E)-3-[6-(trifluoromethyl)-1-benzothien-2-yl]acrylic acid as described in Example 12, Step 3.

Step 7. 7-(Trifluoromethyl)[1]benzothieno[3,2-c]pyridin-1-ol

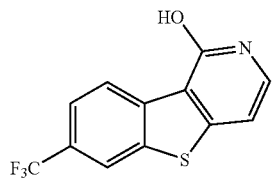 [SMILES: Oc1nccc2sc3cc(C(F)(F)F)ccc3c12]

The title compound was prepared from (2E)-3-[6-(trifluoromethyl)-1-benzothien-2-yl]acryloyl azide as described in Example 12, Step 4.

Step 8. 4-Bromo-7-(trifluoromethyl)[1]benzothieno[3.2-c]pyridin-1-ol

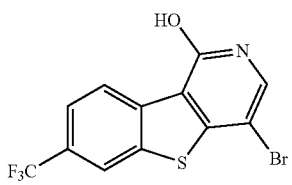 [SMILES: Oc1ncc(Br)c2sc3cc(C(F)(F)F)ccc3c12]

The title compound was prepared from 7-(trifluoromethyl)[1]benzothieno[3,2-c]pyridin-1-ol as described in Example 12, Step 5.

Step 9. 1-Hydroxy-7-(trifluoromethyl)[1]benzothieno[3,2-c]pyridine-4-carbonitrile

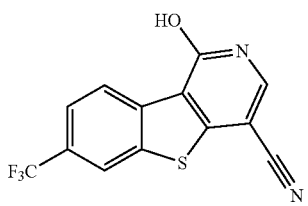 [SMILES: N#Cc1cnc(O)c2c1sc1cc(C(F)(F)F)ccc12]

A solution of 4-bromo-7-(trifluoromethyl)[1]benzothieno[3,2-c]pyridin-1-ol in a 4:1 mixture of DMF/NMP (0.9 M) in the presence of CuCN (2.5 equiv) was heated in a microwave reactor at 150° C. for 25 min. The reaction was poured into 0.1 N HCl and the title product filtered as a solid.

Step 10. 1-Chloro-7-(trifluoromethyl)[1]benzothieno[3,2-c]pyridine-4-carbonitrile

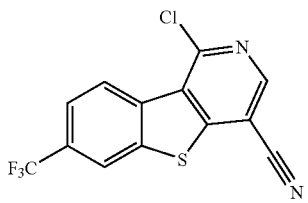

A suspension of 1-hydroxy-7-(trifluoromethyl)[1]benzothieno[3,2-c]pyridine-4-carbonitrile in POCl$_3$ (1 M) was placed in a microwave reactor at 210° C. (normal absorption) for 10 min. The reaction mixture was carefully poured onto ice, stirred for 10 min and the solid filtered off to provide the title compound.

Step 11. 1-[(4-Methoxybenzyl)amino]-7-(trifluoromethyl)[1]benzothieno[3,2-c]pyridine-4-carbonitrile

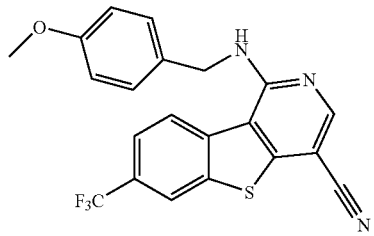 [SMILES: COc1ccc(CNc2ncc(C#N)c3sc4cc(C(F)(F)F)ccc4c23)cc1]

A mixture containing 1-chloro-7-(trifluoromethyl)[1]benzothieno[3,2-c]pyridine-4-carbonitrile, 4-methoxybenzylamine (2.2 equiv), K$_2$CO$_3$ (2.5 equiv) in DMF (0.15 M) was placed in a microwave reactor at 120° C. for 10 min. The reaction was diluted with H$_2$O, the pH adjusted to 4 with HCl and K$_2$HPO$_4$ solution, and the title product was isolated by filtration.

Step 12. 1-Amino-7-(trifluoromethyl)[1]benzothieno[3,2-c]pyridine-4-carboxamide

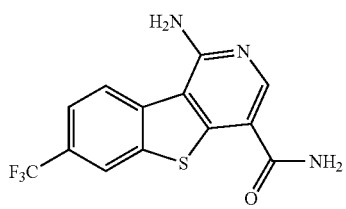 [SMILES: NC(=O)c1cnc(N)c2c1sc1cc(C(F)(F)F)ccc12]

A solution of 1-[(4-methoxybenzyl)amino]-7-(trifluoromethyl)[1]benzothieno[3,2-c]pyridine-4-carbonitrile in conc. H$_2$SO$_4$ (0.1 M) was stirred at room temperature for 2 h. The mixture was poured into H$_2$O, neutralized with KOH and K$_3$PO$_4$ solution to pH 9. The solid was filtered then swished with boiling H$_2$O to give the title compound.

$^1$H NMR (DMSO-d$_6$) δ 8.75 (1H, s), 8.65 (1H, d), 8.55 (1H, s), 8.10 (1H, br s), 7.80 (1H, d), 7.45 (1H, br s), 7.35 (2H, br s).

EXAMPLE 25

1-Amino-6-chloro-5H-pyrido[4,3-b]indole-4-carboxamide

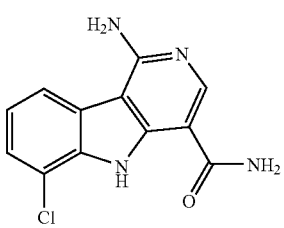 [SMILES: NC(=O)c1cnc(N)c2c1[nH]c1c(Cl)cccc12]

Step 1. 6-Chloro-5H-pyrido[4,3-b]indol-1-ol

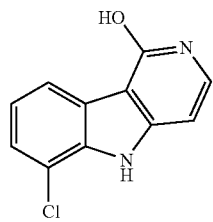 [SMILES: Oc1nccc2[nH]c3c(Cl)cccc3c12]

The title compound was prepared as described in Example 5, Step 1 using 2-chlorophenylhydrazine, except that the reaction mixture was maintained 30 min below the refluxing temperature and 30 min at the reflux. After 30 min at refluxing temperature, the mixture was decanted with caution. The cooled mixture was purified by flash chromatography (EtOAc to 5% MeOH in EtOAc) to provide the title compound.

Step 2.
4-Bromo-6-chloro-5H-pyrido[4.3-b]indol-1-ol

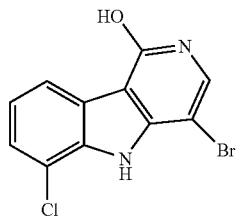 [SMILES: Oc1ncc(Br)c2[nH]c3c(Cl)cccc3c12]

The title compound was prepared from 6-chloro-5H-pyrido[4,3-b]indol-1-ol as described in Example 5, Step 2.

Step 3. 6-Chloro-1-hydroxy-5H-pyrido[4,3-b]indole-4-carbonitrile

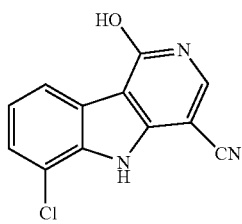 [SMILES: N#Cc1cnc(O)c2c1[nH]c1c(Cl)cccc12]

The title compound was prepared from 4-bromo-6-chloro-5H-pyrido[4,3-b]indol-1-ol as described in Example 5, Step 3.

Step 4.
1,6-Dichloro-5H-pyrido[4,3-b]indole-4-carbonitrile

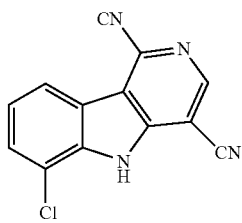 [SMILES: N#Cc1cnc(C#N)c2c1[nH]c1c(Cl)cccc12]

The title compound was prepared from 6-chloro-1-hydroxy-5H-pyrido[4,3-b]indole-4-carbonitrile as described in Example 5, Step 4.

Step 5. 1-Amino-6-chloro-5H-pyrido[4,3-b]indole-4-carboxamide

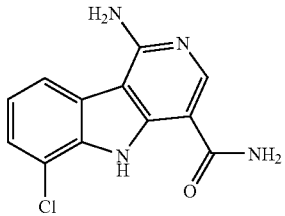 [SMILES: NC(=O)c1cnc(N)c2c1[nH]c1c(Cl)cccc12]

The title compound was prepared from 1,6-dichloro-5H-pyrido[4,3-b]indole-4-carbonitrile as described in Example 5, Step 5 except that the reaction was maintained 18 h at 150° C. and no KOSiMe$_3$ was used.

$^1$H NMR (acetone-d$_6$/DMSO-d$_6$) δ 10.95 (1H, br s), 8.75 (1H, s), 8.25 (1H, s), 8.10 (1H, d s), 7.80 (1H, br s), 7.50 (1H, d), 7.35 (1H, t), 6.90 (1H, br s), 6.50 (1H, br s).

EXAMPLE 26

1-Amino-5-methyl-7-(trifluoromethyl)-5H-pyrido[4,3-b]indole-4-carboxamide

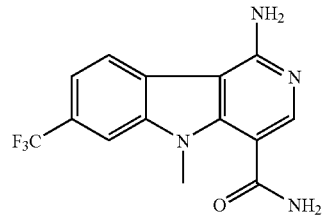

Step 1. 1-Methoxy-5-methyl-7-(trifluoromethyl)-5H-pyrido[4,3-b]indole-4-carbonitrile

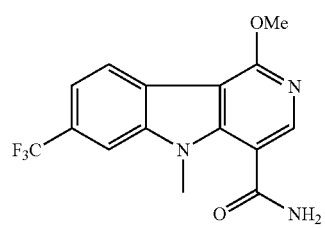

To a suspension of 1-hydroxy-7-(trifluoromethyl)-5H-pyrido[4,3-b]indole-4-carbonitrile (Example 5, Step 3) and K$_2$CO$_3$ (2.5 equiv) in DMF (0.09 M) at room temperature was added MeI (1.5 equiv). After stirring at room temperature for 30 min, saturated NH$_4$Cl solution was added along with H$_2$O, and EtOAc (same amount as DMF). The resulting suspension was stirred vigorously for 10 min, and the product was then collected by filtration to give the title compound as a beige solid.

Step 2. 1-Chloro-5-methyl-7-(trifluoromethyl)-5H-pyrido[4,3-b]indole-4-carbonitrile

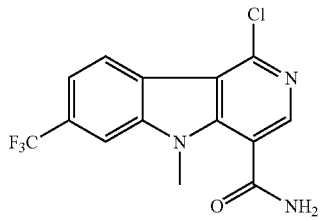 [SMILES: Cn1c2cc(C(F)(F)F)ccc2c2c(Cl)ncc(C(N)=O)c21]

A solution of the product from Step 1 in POCl₃ (0.057 M) was set up on the Smith Creator microwave reactor for 10 min at 175° C. The resulting solution was poured onto cold saturated NaHCO₃ solution and the suspension was stirred until all the reagent was consumed and the final pH was 7-8. The suspension was then filtered to give the title compound as an off-white solid.

Step 3. 1-Amino-5-methyl-7-(trifluoromethyl)-5H-pyrido[4,3-b]indole-4-carbonitrile

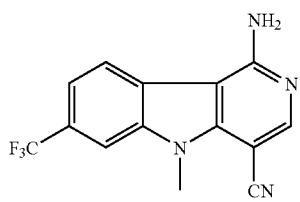 [SMILES: Cn1c2cc(C(F)(F)F)ccc2c2c(N)ncc(C#N)c21]

The product of Step 2 was dissolved in a 2:3 (v/v) mixture of EtOH and conc. NH₄OH (0.027 M) in a stainless steel Parr pressure vessel. The vessel was sealed and the reaction was heated for 16 h at 145° C. After cooling to 0° C., the mixture was concentrated to dryness under vacuum and the resulting solid was stirred with 1:10 EtOAc:hexanes containing 10% MeOH to give the title compound as an off-white solid.

Step 4. 1-Amino-5-methyl-7-(trifluoromethyl)-5H-pyrido[4,3-b]indole-4-carboxamide

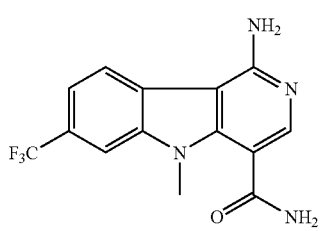

A suspension of the product of Step 3 in a 1:1 (mass/mass) mixture of PPA/CH₃SO₃H (0.034 M) was stirred for 90 min at 120° C. The resulting mixture was then added to ice-cold saturated NaHCO₃ solution, stirring until all the reagent was consumed and the pH was 7-8. The crude material was collected by filtration, and was purified by preparative TLC, eluting with 1:20 MeOH:EtOAc to give the title compound as a white solid.

¹H NMR (DMSO-d₆) δ 8.55 (1H, d), 8.15 (1H, s), 8.00 (2H, br s), 7.55 (1H, d), 7.45 (1H, br s), 6.85 (2H, br s), 3.95 (3H, s).

EXAMPLE 27

1-Amino-7-chloro-5H-pyrido[4,3-b]indole-4-carboxamide

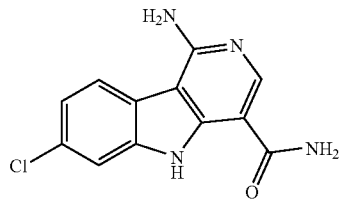 [SMILES: NC(=O)c1cnc(N)c2c1[nH]c1cc(Cl)ccc12]

Step 1. 7-Chloro-5H-pyrido[4,3-b]indol-1-ol

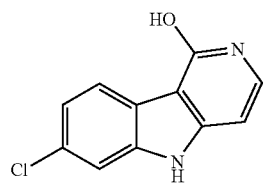 [SMILES: Oc1nccc2[nH]c3cc(Cl)ccc3c12]

The title compound was prepared from 4-chlorophenylhyrazine as described in example 5 step 1.

Step 2. 4-Bromo-7-chloro-5H-pyrido[4,3-b]indol-1-ol

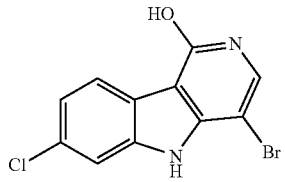 [SMILES: Oc1ncc(Br)c2[nH]c3cc(Cl)ccc3c12]

The title compound was prepared from 7-chloro-5H-pyrido[4,3-b]indol-1-ol as described in example 5 step 2.

Step 3. 1-Hydroxy-7-chloro-5H-pyrido[4,3-b]indole-4-carbonitrile

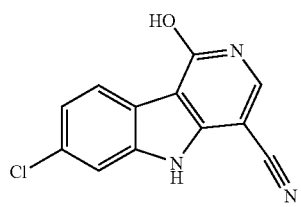 [SMILES: N#Cc1cnc(O)c2c1[nH]c1cc(Cl)ccc12]

The title compound was prepared from 4-bromo-7-chloro-5H-pyrido[4,3-b]indol-1-ol using the same procedure as described in example 5 step 3 except that the reaction was refluxing in NMP for 2 h.

Step 4.
1,7-Dichloro-5H-pyrido[4,3-b]indole-4-carbonitrile

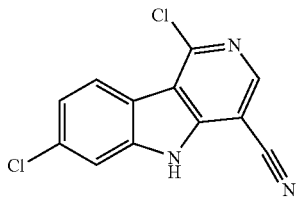 [SMILES: N#Cc1cnc(Cl)c2c1[nH]c1cc(Cl)ccc12]

The title compound was prepared from 1-hydroxy-7-chloro-5H-pyrido[4,3-b]indole-4-carbonitrile using the same procedure as described in example 5 step 4.

Step 5. 1-Amino-7-chloro-5H-pyrido[4,3-b]indole-4-carboxamide

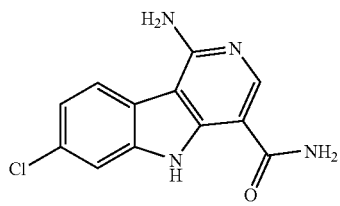 [SMILES: NC(=O)c1cnc(N)c2c1[nH]c1cc(Cl)ccc12]

The title compound was prepared from 1,7-dichloro-5H-pyrido[4,3-b]indole-4-carbonitrile as described in example 5 step 5 except that the reaction was performed without KOSiMe$_3$.

$^1$H NMR (DMSO-d$_6$) δ 11.70 (1H, s), 8.50 (1H, s), 8.30 (1H, d), 7.95 (1H, bs), 7.75 (1H, s), 7.25 (1H, d), 7.20 (1H, bs), 6.90 (2H, bs).

EXAMPLE 28

1-Amino-7-pyridin-3-yl-5-H-pyrido[4,3-b]indole-4-carboxamide

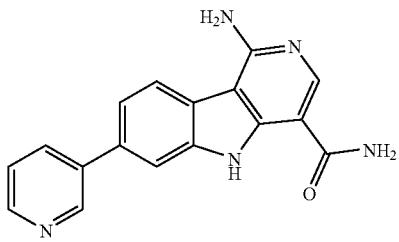 [SMILES: NC(=O)c1cnc(N)c2c1[nH]c1cc(-c3cccnc3)ccc12]

The title compound was prepared from 1-amino-7-chloro-5H-pyrido[4,3-b]indole-4-carboxamide (Example 27, step 5) and pyridine-3-boronic acid 1,3-propanediol cyclic ester using conditions described in example 2.

$^1$H NMR (DMSO-d$_6$) δ 11.65 (1H, s), 8.95 (1H, s), 8.60 (1H, m), 8.55 (1H, s), 8.45 (1H, d), 8.15 (1H, m), 8.10 (1H, s), 7.90 (1H, bs), 7.50 (2H, m), 7.15 (1H, bs), 6.90 (2H, bs)

Pharmaceutical Composition

As a specific embodiment of this invention, 100 mg of a compound of Example 1 is formulated with sufficient finely divided lactose to provide a total amount of 580 to 590 mg to fill a size 0, hard-gelatin capsule.

---

What is claimed is:

1. The compound of Formula II

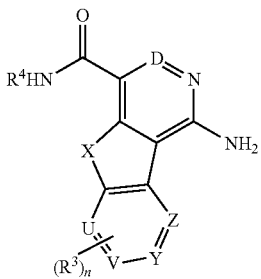

II wherein $R^3$ is:
(a) hydrogen,
(b) halo,
(c) $CF_3$,
(d) $C_{1-6}$alkyl, which is optionally substituted with one or more groups selected from $C_{1-6}$ alkyl, halo or $R^{10}$;
(e) $C_{3-6}$cycloalkyl, which is optionally substituted with one or more groups selected from $C_{1-6}$ alkyl, halo or $R^{10}$;
(f) Aryl, which is optionally substituted with one or more groups selected from $C_{1-6}$ alkyl, halo or $R^{10}$;
(g) $C_{4-10}$ heterocyclyl, which is optionally substituted on either the carbon or the heteroatom with $C_{1-6}$ alkyl, halo or $R^{10}$;
(h) L-A-$R^{10}$,
(i) —$OC_{1-6}$alkyl, which is optionally substituted with one or more groups selected from $C_{1-6}$ alkyl, halo or $R^{10}$;
(j) —OAryl, which is optionally substituted with one or more groups selected from $C_{1-6}$ alkyl, halo or $R^{10}$;

$R^4$ is:
(a) hydrogen,
(b) $C_{1-6}$alkyl, which is optionally substituted with aryl or heteroaryl,
(c) $C_{3-6}$cycloalkyl, which is optionally substituted with aryl or heteroaryl,
(d) Aryl, which is optionally substituted with one to five halo or $R^{10}$; or
(e) Heteroaryl (wherein the heteroaryl has 5 or 6 members in which 1, 2 3 or 4 of the atoms is a heteroatom selected from N, S and O), which is optionally substituted with one to five halo or $R^{10}$;

$R^{10}$ is hydrogen or is selected from the group consisting of:
(a) hydrogen;
(b) $CO_2R^{11}$;
(c) $C(O)R^{11}$;
(d) $NHR^{11}$;
(e) $NR^{11}R^{12}$;
(f) $NHS(O)_2R^{11}$;
(g) $NHC(O)R^{11}$;
(h) $NHC(O)OR^{11}$;
(i) NH—C=(NH)$NH_2$;
(j) $NHC(O)NH_2$;
(k) $NHC(O)NHR^{11}$;
(l) $NHC(O)NR^{11}R^{12}$;
(m) N $C_{3-6}$cycloalkyl;
(n) $C(O)NHR^{11}$;
(o) $C(O)NR^{11}R^{12}$;
(p) $SO_2NHR^{11}$;
(q) $SO_2NHC(O)R^{12}$;

$R^{11}$ is selected from the group consisting of:
(a) hydrogen;
(b) $C_{3-6}$cycloalkyl, which is optionally substituted with aryl, heteroaryl, or one to five halo;
(c) $C_{1-6}$alkyl, which is optionally substituted with aryl, heteroaryl, or one to five halo;
(d) Aryl, which is optionally substituted with one to five halo; or
(e) Heteroaryl (wherein the heteroaryl has 5 or 6 members in which 1, 2 3 or 4 of the atoms is a heteroatom selected from N, S and O), which is optionally substituted with one to five halo;

$R^{12}$ is selected from the group consisting of:
(a) hydrogen,
(b) $C_{1-6}$alkyl, which is optionally substituted with aryl, heteroaryl or one to five halo;
(c) $C_{3-6}$cycloalkyl, which is optionally substituted with aryl, heteroaryl or one to five halo;
(d) Aryl, which is optionally substituted with one to five halo;
(e) Heteroaryl (wherein the heteroaryl has 5 or 6 members in which 1, 2 3 or 4 of the atoms is a heteroatom selected from N, S and O), which is optionally substituted with one to five halo;

A is absent or is selected from the group consisting of: a aryl or Heteroaryl, wherein the heteroaryl is a ring of 5 or 6 atoms a monocyclic ring of 5 or 6 atoms or a bicyclic ring of 9 or 10 atoms in which 1, 2, 3 or 4 of the atoms is a heteroatom selected from N, S and O, wherein the aryl or heteroaryl is optionally substituted with one or more substituents selected from halo, $C_{1-3}$alkyl, —C(O)OH, $CF_3$, —$SO_2C_{1-3}$alkyl, $SO_2NC_{1-3}$alkyl, $SO_2NHC(O)$—$C_{1-3}$alkyl and $N(CH_3)_2$;

L is absent or is selected from the group consisting of: —$(CH_2)_k$—W—, —W—$(CH_2)_k$—, —C≡C—, —$C_{1-6}$ alkyl-, —$C_{3-6}$cycloalkyl-, —$C_{2-5}$alkene-, wherein the alkene is optionally substituted with one or more substituent group selected from $C_{1-6}$alkyl and $C_{1-6}$cycloalkyl;

X is selected from the group consisting of: NH and $NC_{1-6}$ alkyl;

D is selected from CH;

W is selected from the group consisting of: O, NH, $NC_{1-6}$alkyl and $S(O)_m$, with the proviso that when W is O, $S(O)_m$, NH or $NC_{1-6}$alkyl and simultaneously A is absent then $R^{10}$ is $CO_2R^{11}$, $COR^{11}$, $CONHR^{11}$ or $CONR^{11}R^{12}$;

U is CH;
V is CH;
Y is CH;
Z is CH;
k=0, 1, 2, 3, 4 or 5;
m=0, 1 or 2;
n=0, 1, 2 or 3;
or a pharmaceutically acceptable salt or stereoisomer thereof.

2. The compound selected from:
1-Amino-7-(trifluoromethyl)-5H-pyrido[4,3-b]indole-4-carboxamide;
1-Amino-8-fluoro-5H-pyrido[4,3-b]indole-4-carboxamide;
8-Fluoro-1-(methylamino)-5H-pyrido[4,3-b]indole-4-carboxamide;
1-(Butylamino)-8-fluoro-5H-pyrido[4,3-b]indole-4-carboxamide;
8-Fluoro-1-(1'H,3H-spiro[2-benzofuran-1,4'-piperidin]-1'-yl)-5H-pyrido[4,3-b]indole-4-carboxamide;
8-fluoro-1-pyrrolidin-1-yl-5H-pyrido[4,3-b]indole-4-carboxamide;
1-(ethylamino)-8-fluoro-5H-pyrido[4,3-b]indole-4-carboxamide;
8-fluoro-1-(propylamino)-5H-pyrido[4,3-b]indole-4-carboxamide;
8-fluoro-1-piperidin-1-yl-5H-pyrido[4,3-b]indole-4-carboxamide;
8-fluoro-1-morpholin-4-yl-5H-pyrido[4,3-b]indole-4-carboxamide;
8-fluoro-1-(methylamino)-5H-pyrido[4,3-b]indole-4-carboxamide;
1-(cyclohexylamino)-8-fluoro-5H-pyrido[4,3-b]indole-4-carboxamide;
1-(benzylamino)-8-fluoro-5H-pyrido[4,3-b]indole-4-carboxamide;
8-fluoro-1-(isobutylamino)-5H-pyrido[4,3-b]indole-4-carboxamide;
8-fluoro-1-(isopropylamino)-5H-pyrido[4,3-b]indole-4-carboxamide;
1-[(cyclohexylmethyl)amino]-8-fluoro-5H-pyrido[4,3-b]indole-4-carboxamide;
1-(butylamino)-8-fluoro-5H-pyrido[4,3-b]indole-4-carboxamide;
8-fluoro-1-(pentylamino)-5H-pyrido[4,3-b]indole-4-carboxamide;
1-(cyclobutylamino)-8-fluoro-5H-pyrido[4,3-b]indole-4-carboxamide;
1-(cyclopentylamino)-8-fluoro-5H-pyrido[4,3-b]indole-4-carboxamide;
1-(cycloheptylamino)-8-fluoro-5H-pyrido[4,3-b]indole-4-carboxamide;
1-(cyclooctylamino)-8-fluoro-5H-pyrido[4,3-b]indole-4-carboxamide;
8-fluoro-1-[(4-methylcyclohexyl)amino]-5H-pyrido[4,3-b]indole-4-carboxamide;
8-fluoro-1-[(2-hydroxycyclohexyl)amino]-5H-pyrido[4,3-b]indole-4-carboxamide;
8-fluoro-1-[(2-methylcyclohexyl)amino]-5H-pyrido[4,3-b]indole-4-carboxamide;
8-fluoro-1-[(trans-4-hydroxycyclohexyl)amino]-5H-pyrido[4,3-b]indole-4-carboxamide;
8-fluoro-1-(tetrahydro-2H-pyran-4-ylamino)-5H-pyrido[4,3-b]indole-4-carboxamide;
8-fluoro-1-(heptylamino)-5H-pyrido[4,3-b]indole-4-carboxamide;
8-fluoro-1-[(1,2,2-trimethylpropyl)amino]-5H-pyrido[4,3-b]indole-4-carboxamide;
8-fluoro-1-(hexylamino)-5H-pyrido[4,3-b]indole-4-carboxamide;
8-fluoro-1-(octylamino)-5H-pyrido[4,3-b]indole-4-carboxamide;
1-(2,2-dimethylmorpholin-4-yl)-8-fluoro-5H-pyrido[4,3-b]indole-4-carboxamide;
1-(3,3-difluoropyrrolidin-1-yl)-8-fluoro-5H-pyrido[4,3-b]indole-4-carboxamide;
1-(3,3-difluoropiperidin-1-yl)-8-fluoro-5H-pyrido[4,3-b]indole-4-carboxamide;
8-fluoro-1-(4-hydroxypiperidin-1-yl)-5H-pyrido[4,3-b]indole-4-carboxamide;
Ethyl-4-{[4-(aminocarbonyl)-8-fluoro-5H-pyrido[4,3-b]indol-1-yl]amino}piperidine-1-carboxylate;
1-[(1-benzylpiperidin-4-yl)amino]-8-fluoro-5H-pyrido[4,3-b]indole-4-carboxamide;
8-fluoro-1-[3-(hydroxymethyl)piperidin-1-yl]-5H-pyrido[4,3-b]indole-4-carboxamide;
8-fluoro-1-(4-phenyl-3,6-dihydropyridin-1(2H)-yl)-5H-pyrido[4,3-b]indole-4-carboxamide;
1-(4-benzyl-4-hydroxypiperidin-1-yl)-8-fluoro-5H-pyrido[4,3-b]indole-4-carboxamide;
1-(4-benzyl-3,6-dihydropyridin-1(2H)-yl)-8-fluoro-5H-pyrido[4,3-b]indole-4-carboxamide;
1-(4-benzylidenepiperidin-1-yl)-8-fluoro-5H-pyrido[4,3-b]indole-4-carboxamide;
8-fluoro-1-(4-phenylpiperidin-1-yl)-5H-pyrido[4,3-b]indole-4-carboxamide;
8-fluoro-1-(3-hydroxypiperidin-1-yl)-5H-pyrido[4,3-b]indole-4-carboxamide;
8-fluoro-1-(2-phenylpiperidin-1-yl)-5H-pyrido[4,3-b]indole-4-carboxamide;
8-fluoro-1-{[(1S,2R)-2-(methoxymethyl)cyclopentyl]amino}-5H-pyrido[4,3-b]indole-4-carboxamide;
8-fluoro-1-{[(1R)-1,2,2-trimethylpropyl]amino}-5H-pyrido[4,3-b]indole-4-carboxamide;
8-fluoro-1-{[(1S)-1,2,2-trimethylpropyl]amino}-5H-pyrido[4,3-b]indole-4-carboxamide;
N-[4-(aminocarbonyl)-8-fluoro-5H-pyrido[4,3-b]indol-1-yl]-3-methyl-D-valyl-N,3-dimethylvalinamide;
N-[4-(aminocarbonyl)-8-fluoro-5H-pyrido[4,3-b]indol-1-yl]-3-methyl-L-valyl-N,3-dimethylvalinamide;
1-(bicyclo[2.2.1]hept-2-ylamino)-8-fluoro-5H-pyrido[4,3-b]indole-4-carboxamide;
1-{[(1R)-1-cyclohexylethyl]amino}-8-fluoro-5H-pyrido[4,3-b]indole-4-carboxamide;
8-fluoro-1-(3-phenylpiperidin-1-yl)-5H-pyrido[4,3-b]indole-4-carboxamide;
8-fluoro-1-(3-phenylpiperidin-1-yl)-5H-pyrido[4,3-b]indole-4-carboxamide;
8-fluoro-1-[(1-hydroxypropyl)amino]-5H-pyrido[4,3-b]indole-4-carboxamide;
8-fluoro-1-(1'H,3H-spiro[2-benzofuran-1,4'-piperidin]-1'-yl)-5H-pyrido[4,3-b]indole-4-carboxamide;
1-Amino-5H-pyrido[4,3-b]indole-4-carboxamide;
1-Amino-8-bromo-5H-pyrido[4,3-b]indole-4-carboxamide;
1-Amino-6-chloro-5H-pyrido[4,3-b]indole-4-carboxamide;
1-Amino-5-methyl-7-(trifluoromethyl)-5H-pyrido[4,3-b]indole-4-carboxamide;

1-Amino-7-chloro-5H-pyrido[4,3-b]indole-4-carboxamide;

1-Amino-7-pyridin-3-yl-5-H-pyrido[4,3-b]indole-4-carboxamide;

or a pharmaceutically acceptable salt or stereoisomer thereof.

3. A pharmaceutical composition comprising a therapeutically effective amount of a compound according to claim 1 and a pharmaceutically acceptable carrier.

* * * * *